US010889806B2

(12) United States Patent
Borra-Garske et al.

(10) Patent No.: US 10,889,806 B2
(45) Date of Patent: Jan. 12, 2021

(54) ENGINEERED PANTOTHENATE KINASE VARIANT ENZYMES

(71) Applicant: Codexis, Inc., Redwood City, CA (US)

(72) Inventors: Margie Tabuga Borra-Garske, Palo Alto, CA (US); Oscar Alvizo, Fremont, CA (US); Lillian Jasmine Miller, Saratoga, CA (US); Jesse B. Slaton, Sacramento, CA (US); Aksiniya Lyubenova Petkova, Sunnyvale, CA (US); Nandhitha Subramanian, San Francisco, CA (US); Joshua Kolev, Rahway, NJ (US); Anna Fryszkowska, New York, NY (US); Agustina Rodriguez-Granillo, Rahway, NJ (US); Grant Murphy, Rahway, NJ (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 16/460,147

(22) Filed: Jul. 2, 2019

(65) Prior Publication Data

US 2020/0010815 A1 Jan. 9, 2020

Related U.S. Application Data

(60) Provisional application No. 62/695,587, filed on Jul. 9, 2018, provisional application No. 62/822,301, filed on Mar. 22, 2019.

(51) Int. Cl.
*C12N 9/12* (2006.01)

(52) U.S. Cl.
CPC .... *C12N 9/1205* (2013.01); *C12Y 207/01033* (2013.01)

(58) Field of Classification Search
CPC .................... C12N 9/12; C12N 9/1205; C12Y 207/01033; A61K 25/28
See application file for complete search history.

(56) References Cited

U.S. PATENT DOCUMENTS

| | | | |
|---|---|---|---|
| 5,605,793 | A | 2/1997 | Stemmer |
| 5,811,238 | A | 9/1998 | Stemmer et al. |
| 5,830,721 | A | 11/1998 | Stemmer et al. |
| 5,834,252 | A | 11/1998 | Stemmer et al. |
| 5,837,458 | A | 11/1998 | Minshull et al. |
| 5,928,905 | A | 7/1999 | Stemmer et al. |
| 6,096,548 | A | 8/2000 | Stemmer |
| 6,117,679 | A | 9/2000 | Stemmer |
| 6,132,970 | A | 10/2000 | Stemmer |
| 6,165,793 | A | 12/2000 | Stemmer |
| 6,180,406 | B1 | 1/2001 | Stemmer |
| 6,251,674 | B1 | 6/2001 | Tobin et al. |
| 6,265,201 | B1 | 7/2001 | Wackett et al. |
| 6,277,638 | B1 | 8/2001 | Stemmer |
| 6,287,861 | B1 | 9/2001 | Stemmer et al. |
| 6,287,862 | B1 | 9/2001 | delCardayre et al. |
| 6,291,242 | B1 | 9/2001 | Stemmer |
| 6,297,053 | B1 | 10/2001 | Stemmer |
| 6,303,344 | B1 | 10/2001 | Patten et al. |
| 6,309,883 | B1 | 10/2001 | Minshull et al. |
| 6,319,713 | B1 | 11/2001 | Patten et al. |
| 6,319,714 | B1 | 11/2001 | Crameri et al. |
| 6,323,030 | B1 | 11/2001 | Stemmer |
| 6,326,204 | B1 | 12/2001 | delCardayre et al. |
| 6,335,160 | B1 | 1/2002 | Patten et al. |
| 6,335,198 | B1 | 1/2002 | delCardayre et al. |
| 6,337,186 | B1 | 1/2002 | Krebber |
| 6,344,356 | B1 | 2/2002 | Stemmer |
| 6,352,859 | B1 | 3/2002 | delCardayre et al. |
| 6,355,484 | B1 | 3/2002 | Patten et al. |
| 6,358,740 | B1 | 3/2002 | Patten et al. |
| 6,358,742 | B1 | 3/2002 | Stemmer |
| 6,365,377 | B1 | 4/2002 | Patten et al. |
| 6,365,408 | B1 | 4/2002 | Stemmer |
| 6,368,861 | B1 | 4/2002 | Crameri et al. |
| 6,372,497 | B1 | 4/2002 | Stemmer |
| 6,376,246 | B1 | 4/2002 | Crameri et al. |
| 6,379,964 | B1 | 4/2002 | delCardayre et al. |
| 6,387,702 | B1 | 5/2002 | Stemmer |
| 6,391,552 | B2 | 5/2002 | Stemmer |
| 6,391,640 | B1 | 5/2002 | Minshull et al. |
| 6,395,547 | B1 | 5/2002 | Stemmer |
| 6,406,855 | B1 | 6/2002 | Patten et al. |
| 6,406,910 | B1 | 6/2002 | Patten et al. |
| 6,413,745 | B1 | 7/2002 | Patten et al. |
| 6,413,774 | B1 | 7/2002 | Stemmer |
| 6,420,175 | B1 | 7/2002 | Stemmer |
| 6,423,542 | B1 | 7/2002 | Crameri et al. |
| 6,426,224 | B1 | 7/2002 | Crameri et al. |
| 6,436,675 | B1 | 8/2002 | Welch et al. |

(Continued)

FOREIGN PATENT DOCUMENTS

| | | | |
|---|---|---|---|
| WO | 95/22625 | A1 | 8/1995 |
| WO | 95/33836 | A1 | 12/1995 |
| WO | 96/00787 | A1 | 1/1996 |
| WO | 97/0078 | A1 | 1/1997 |
| WO | 97/35966 | A1 | 10/1997 |

(Continued)

OTHER PUBLICATIONS

Chen et al.(2006; Analysis of the temperature-sensitive mutation of *Escherichia coli* pantothenate kinase reveals YbjN as a possible protein stabilizer. Biochem. Biophys. Res. Commun. 345: 834-842.*

(Continued)

*Primary Examiner* — Karen Cochrane Carlson
(74) *Attorney, Agent, or Firm* — Codexis, Inc.

(57) ABSTRACT

The present invention provides engineered pantothenate kinase (PanK) enzymes, polypeptides having PanK activity, and polynucleotides encoding these enzymes, as well as vectors and host cells comprising these polynucleotides and polypeptides. Methods for producing PanK enzymes are also provided. The present invention further provides compositions comprising the PanK enzymes and methods of using the engineered PanK enzymes. The present invention finds particular use in the production of pharmaceutical compounds.

29 Claims, No Drawings

Specification includes a Sequence Listing.

(56) References Cited

U.S. PATENT DOCUMENTS

| | | | |
|---|---|---|---|
| 6,444,468 | B1 | 9/2002 | Stemmer et al. |
| 6,455,253 | B1 | 9/2002 | Patten et al. |
| 6,479,652 | B1 | 11/2002 | Crameri et al. |
| 6,482,647 | B1 | 11/2002 | Stemmer |
| 6,483,011 | B1 | 11/2002 | Stemmer et al. |
| 6,484,105 | B2 | 11/2002 | Zhang |
| 6,489,146 | B2 | 12/2002 | Stemmer et al. |
| 6,500,617 | B1 | 12/2002 | Stemmer et al. |
| 6,500,639 | B2 | 12/2002 | Subramanian |
| 6,506,602 | B1 | 1/2003 | Stemmer |
| 6,506,603 | B1 | 1/2003 | Stemmer |
| 6,518,065 | B1 | 2/2003 | Stemmer |
| 6,519,065 | B1 | 2/2003 | Colbourne et al. |
| 6,521,453 | B1 | 2/2003 | Crameri et al. |
| 6,528,311 | B1 | 3/2003 | delCardayre et al. |
| 6,537,746 | B2 | 3/2003 | Arnold et al. |
| 6,573,098 | B1 | 6/2003 | Stemmer |
| 6,576,467 | B1 | 6/2003 | Stemmer |
| 6,579,678 | B1 | 6/2003 | Patten et al. |
| 6,586,182 | B1 | 7/2003 | Patten et al. |
| 6,605,430 | B1 | 7/2003 | Affholter et al. |
| 6,602,986 | B1 | 8/2003 | Stemmer et al. |
| 6,613,514 | B2 | 9/2003 | Patten et al. |
| 6,653,072 | B1 | 11/2003 | Patten et al. |
| 6,686,515 | B1 | 2/2004 | Lassner et al. |
| 6,703,240 | B1 | 3/2004 | Stemmer et al. |
| 6,716,631 | B1 | 4/2004 | delCardayre et al. |
| 6,825,001 | B2 | 11/2004 | Wackett et al. |
| 6,902,922 | B2 | 6/2005 | Ness et al. |
| 6,917,882 | B2 | 7/2005 | Selfinov et al. |
| 6,946,296 | B2 | 9/2005 | Patten et al. |
| 6,961,664 | B2 | 11/2005 | Selfinov et al. |
| 6,995,017 | B1 | 2/2006 | Stemmer |
| 7,024,312 | B1 | 4/2006 | Selfinov et al. |
| 7,058,515 | B1 | 6/2006 | Selfinov et al. |
| 7,105,297 | B2 | 9/2006 | Minshull et al. |
| 7,148,054 | B2 | 12/2006 | delCardayre et al. |
| 7,220,566 | B2 | 5/2007 | Ness et al. |
| 7,288,375 | B2 | 10/2007 | Stemmer et al. |
| 7,384,387 | B1 | 6/2008 | Raillard et al. |
| 7,421,347 | B2 | 9/2008 | Selfinov et al. |
| 7,430,477 | B2 | 9/2008 | Selfinov et al. |
| 7,462,469 | B2 | 12/2008 | Bass et al. |
| 7,534,564 | B2 | 5/2009 | Patten et al. |
| 7,620,500 | B2 | 11/2009 | Mundorff et al. |
| 7,620,502 | B2 | 11/2009 | Selfinov et al. |
| 7,629,170 | B2 | 12/2009 | delCardayre et al. |
| 7,702,464 | B1 | 4/2010 | Emig et al. |
| 7,747,391 | B2 | 6/2010 | Gustafsson et al. |
| 7,747,393 | B2 | 6/2010 | Fox |
| 7,751,986 | B2 | 7/2010 | Gustafsson et al. |
| 7,776,598 | B2 | 8/2010 | Patten et al. |
| 7,783,428 | B2 | 8/2010 | Gustafsson et al. |
| 7,795,030 | B2 | 9/2010 | Minshull et al. |
| 7,853,410 | B2 | 12/2010 | Selfinov et al. |
| 7,868,138 | B2 | 1/2011 | Stemmer et al. |
| 7,873,477 | B1 | 1/2011 | Gustafsson et al. |
| 7,873,499 | B2 | 1/2011 | Selfinov et al. |
| 7,904,249 | B2 | 3/2011 | Selfinov et al. |
| 7,957,912 | B2 | 6/2011 | Selfinov et al. |
| 7,981,614 | B2 | 7/2011 | Stemmer et al. |
| 8,014,961 | B2 | 9/2011 | Bass et al. |
| 8,029,988 | B2 | 10/2011 | Crameri et al. |
| 8,048,674 | B2 | 11/2011 | Minshull et al. |
| 8,058,001 | B2 | 11/2011 | Crameri et al. |
| 8,076,138 | B2 | 12/2011 | delCardayre et al. |
| 8,108,150 | B2 | 1/2012 | Mundorff et al. |
| 8,170,806 | B2 | 5/2012 | Selfinov et al. |
| 8,224,580 | B2 | 7/2012 | Mundorff et al. |
| 8,377,681 | B2 | 2/2013 | delCardayre et al. |
| 8,383,346 | B2 | 2/2013 | Colbeck et al. |
| 8,457,903 | B1 | 6/2013 | Emig et al. |
| 8,504,498 | B2 | 8/2013 | Fox |
| 8,589,085 | B2 | 11/2013 | Selfinov et al. |
| 8,762,066 | B2 | 6/2014 | Fox |
| 8,768,871 | B2 | 7/2014 | Fox |
| 9,593,326 | B2 | 3/2017 | Clark et al. |
| 9,714,437 | B2 | 7/2017 | Chan et al. |
| 2008/0220990 | A1 | 9/2008 | Fox |
| 2009/0312196 | A1 | 12/2009 | Colbeck et al. |

FOREIGN PATENT DOCUMENTS

| | | | |
|---|---|---|---|
| WO | 98/27230 | A1 | 6/1998 |
| WO | 00/42651 | A1 | 7/2000 |
| WO | 2001/21772 | A2 | 3/2001 |
| WO | 01/75767 | A2 | 10/2001 |
| WO | 2009/152336 | A1 | 12/2009 |
| WO | 2012/087039 | A2 | 6/2012 |

OTHER PUBLICATIONS

Rock et al. 2003; Role of feedback regulation of patnothenate kinase (CoaA) in control of coenzymes A levels in *Escherichia coli*. Journal of Bacteriology. 185(11): 3410-3415.*

Altschul, S., et al., "Basic local alignment search tool," J. Mol. Biol., 215: 403-410 (1990).

Altschul, S.F., et al., "Gapped BLAST and PSI-BLAST: a new generation of protein database search programs," Nucleic Acids Res., 25(17):3389-3402 (1997).

Baldino, Jr., F., et al., "High-Resolution in Situ Hybridization Histochemistry," Methods Enzymology, 168:761-777 (1989).

Batzer, M.A., "Erratum: Structure and variability of recently inserted Alu family members", Nucleic Acids Res 19:698-699 [1991].

Bolton, E.T., et al., "A General Method for the Iisolation of RNA Complementary to DNA," Proc. Natl. Acad. Sci. USA 48:1390 ( 1962).

Botstein, D., et al., "Strategies and applications of in vitro mutagenesis," Science, 229(4719):1193-1201, 1985.

Breslauer, K.J., et al., "Predicting DNA duplex stability from the base sequence," Proc. Natl. Acad. Sci. USA, 83:3746-3750 (1986).

Carter, P., "Site-directed mutagenesis," Biochem. J., 237:1-7 (1986).

Chaveroche, M., et al., "A rapid method for efficient gene replacement in the filamentous fungus *Aspergillus nidulans*," Nucl. Acids Res., 28:22 e97 [2000].

Cho, Y., et al., "A high throughput targeted gene disruption method for Alternaria brassicicola functional genomics using linear minimal element (LME) constructs," Mol Plant Microbe Interact,19(1):7-15 [2006].

Christians, F.C., et al., "Directed evolution of thymidine kinase for AZT phosphorylation using DNA family shuffling," Nat. Biotechnol., 17:259-264 (1999).

Combier, J.-P., et al., "Agrobacterium tumefaciens-mediated transformation as a tool for insertional mutagenesis in the symbiotic ectomycorrhizal fungus *Hebeloma cylindrosporum*," FEMS Microbiol Lett., 220:141-8 [2003].

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15(5):436-438 (1997).

Dale, S.J., et al. "Oligonucleotide-directed random mutagenesis using the phosphorothioate method," Methods Mol. Biol., 57:369-74 (1996).

De Boer, H.A., et al., "The tac promoter: A functional hybrid derived from the trp and lac promoters," Proc. Natl Acad. Sci. USA, 80: 21-25 (1983).

Ehrlich, S.D.,"DNA cloning in Bacillus subtilis," Proc. Natl. Acad. Sci. USA, 75(3):1433-1436 [1978].

Eisenberg, D., et al., "Analysis of Membrane and Surface Protein Sequences with the Hydrophobic Moment Plot," J. Mol. Biol., 179:125-142 [1984].

Firon, A., et al., "Identification of Essential Genes in the Human Fungal Pathogen Aspergillus fumigatus by Transposon Mutagenesis," Eukaryot. Cell, 2(2):247-55 [2003].

(56) References Cited

OTHER PUBLICATIONS

Freier, S.M., et al., "Improved free-energy parameters for predictions of RNA duplex stability," Proc. Natl. Acad. Sci USA, 83:9373-9377 (1986).
Guo, Z., et al., "3'-End-Forming Signals of Yeast mRNA," Mol. Cell. Biol., 15(11):5983-5990 [1995].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S., et al., "Amino acid substitution matrices from protein blocks," Proc. Natl. Acad. Sci. USA, 89:10915-10919 [1992].
Hong, J., et al., "Cloning and functional expression of thermostable beta-glucosidase gene from Themioascus aurantiacus," Appl. Microbiol. Biotechnol, 73:1331-1339 [2007].
Kierzek, R., et al., "Polymer-Supported RNA Synthesis and Its Application to Test the Nearest-Neighbor Model for Duplex Stability," Biochemistry, 25:7840-7846 (1986).
Kramer, B., et al., "Different base/base mismatches are corrected with different efficiencies by the methyl-directed DNA mismatch-repair system of *E. coli*," Cell, 38(3):879-887 [1984].
Lathe, R., et al., "Plasmid and bacteriolphage vecotrs for excision of intact inserts," Gene, 57:193-201 [1987].
Ling, M.M., et al., "Approaches to DNA Mutagenesis: An Overview," Anal. Biochem., 254(2):157-78 [1997].
Maruyama, J., "Multiple gene disruptions by marker recycling with highly efficient gene-targeting background (delta-igD) in Aspergillus oryzae," Biotechnol Lett., 30:1811-1817 [2008].
McInerney, J.O., "GCUA: general codon usage analysis," Bioinformatics, 14(4):372-73 [1998].
Minshull, J., et al., "Protein evolution by molecular breeding," Curr. Op. Chem. Biol., 3(3):284-290 (1999).
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
Parry, N.J., et al., "Biochemical characterization and mechanism of action of a thermostablebeta-glucosidase purified from Thermoascus aurantiacus," Biochem. J., 353:117-127 [2001].
Pearson, W.R., "Improved tools for biological sequence comparison," Proc. Nat'l. Acad. Sci. USA, 85:2444-2448 (1988).
Jorath, J., "Immobilized metal ion affinity chromatography," Protein Expression and Purification, 3:263-281 (1992).
Romanos, M.A., et al., "Foreign gene expression in yeast: a review," Yeast 8:423-488 [1992].
Rychlik, W., et al., "Optimization of the annealing temperature for DNA amplification in vitro," Nucleic Acids Res, 18(21):6409-6412 (1990).
Simonen, M., et al., "Protein Secretion in Bacillus Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Stenico, M., et al., "Codon usage in Caenorhabditis elegans: delineation of translational selection and mutational biases," Nucl. Acids Res. 22(13):2437-46 [1994].
Suggs, S.V., et al., "Use of synthetic oligodeoxyribonucleotides for the isolation of specific cloned DNA sequences," in Developmental Biology Using Purified Genes (Brown et al., eds.), pp. 683-693, Academic Press (1981).
Takahashi, T., et al., "Efficient gene disruption in the koji -mold Aspergillus sojae using a novel variation of the positive-negative method," Mol. Gen. Genom., 272: 344-352 [2004].
Tiwari, S., et al., "Prediction of probable genes by Fourier analysis of genomic sequences," Comput. Appl. Biosci. 13(3):263-270 [1997].
Uberbacher, E.C., et al., "Discovering and Understanding Genes in Human DNA Sequence Using Grail," Methods Enzymol., 266:259-281 [1996].
Villa-Komaroff, L., et al., "A bacterial clone synthesizing proinsulin," Proc. Natl Acad. Sci. USA, 75:3727-3731 (1978).
Awuah, E., et al., "Exploring structural motifs necessary for substrate binding in the active site of *Escherichia coli* pantothenate kinase," Bioorganic & Medicinal Chemistry, 22:3083-3090 [2014].
Li, B., "Structural Studies of the Klebsiella pneumoniae Pantothenate Kinsase in Complex with Pantothenamide Substrate Analogues," Master of Science Thesis [2012].
Uchiyama, S., et al., "Derivatization of carbonyl compounds with 2,4-dinitrphenylhydrazine and their subsequent determination by high-performance liquid chromatography," Journal of Chromatography B, 879(17-18):1282-1289 [2011].
NCBI Submission PDB: 4NE2_A Chain A, Pantothenate Kinase dated Jun. 26, 2014.
Wada, K., et al., "Codon usage tabulated from the GenBank genetic sequence data," Nucl. Acids Res., 20:2111-2118 [1992].
Wells, J.A., et al., "Cassette mutagenesis: an efficient method for generation of multiple mutations at defined sites," Gene, 34:315-323 (1985).
Wetmur, J. G., "DNA Probes: Applications of the Principles of Nucleic Acid Hybridization," Crit Rev Biochem Mol Biol, 26(3/4):227-259 (1991).
Wilson, I.A., et al., "The structure of antigenic determinant in a protein," Cell, 37:767-778 [1984].
Wright, F., "The 'effective number of codons' used in a gene," Gene 87:23-29 [1990].
You, B., et al., "Gene-specifc disruption in the fillamentous fungus Cercospora nicotianae using a split-marker approach," Arch Micriobiol., 191:615-622 [2009].
Zhang, J-H., et al., "Directed evolution of a fucosidase from a galactosidase by DNA shuffling and screening," Proc. Nat. Acad. Sci., U.S.A., 94:4504-4509 (1997).

* cited by examiner

ENGINEERED PANTOTHENATE KINASE VARIANT ENZYMES

The present application claims priority to U.S. Prov. Pat. Appln. Ser. No. 62/695,587, filed Jul. 9, 2018 and U.S. Prov. Pat. Appln. Ser. No. 62/822,301, filed Mar. 22, 2019, both of which are incorporated by reference in its entirety, for all purposes.

FIELD OF THE INVENTION

The present invention provides engineered pantothenate kinase (PanK) enzymes, polypeptides having PanK activity, and polynucleotides encoding these enzymes, as well as vectors and host cells comprising these polynucleotides and polypeptides. Methods for producing PanK enzymes are also provided. The present invention further provides compositions comprising the PanK enzymes and methods of using the engineered PanK enzymes. The present invention finds particular use in the production of pharmaceutical compounds.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-177WO2_ST25.txt", a creation date of Jun. 26, 2019 and a size of 553 kilobytes. The Sequence Listing filed via EFS-Web is part of the specification and incorporated in its entirety by reference herein.

BACKGROUND OF THE INVENTION

The retrovirus designated as human immunodeficiency virus (HIV) is the etiological agent of acquired immune deficiency syndrome (AIDS), a complex disease that involves progressive destruction of affected individuals' immune systems and degeneration of the central and peripheral nervous systems. A common feature of retrovirus replication is reverse transcription of the viral RNA genome by a virally-encoded reverse transcriptase to generate DNA copies of HIV sequences, required for viral replication. Some compounds, such as MK-8591 are known reverse transcriptase inhibitors and have found use in the treatment of AIDS and similar diseases. While there are some compounds known to inhibit HIV reverse transcriptase, there remains a need in the art for additional compounds that are more effective in inhibiting this enzyme and thereby ameliorating the effects of AIDS.

Nucleoside analogues such as MK-8591 (Merck) are effective inhibitors of HIV's reverse transcriptase due their similarity to natural nucleosides used in the synthesis of DNA. The binding of these analogues by the reverse transcriptase stalls the synthesis of DNA by inhibiting the progressive nature of the reverse transcriptase. The stalling of the enzyme results in the premature termination of the DNA molecule making it ineffective. However, production of nucleoside analogues by standard chemical synthetic techniques can pose a challenge due to their chemical complexity.

SUMMARY OF THE INVENTION

The present invention provides engineered pantothenate kinase (PanK) enzymes, polypeptides having PanK activity, and polynucleotides encoding these enzymes, as well as vectors and host cells comprising these polynucleotides and polypeptides. Methods for producing PanK enzymes are also provided. The present invention further provides compositions comprising the PanK enzymes and methods of using the engineered PanK enzymes. The present invention finds particular use in the production of pharmaceutical compounds.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 2, SEQ ID NO: 30, SEQ ID NO: 60, SEQ ID NO: 132, SEQ ID NO: 222, SEQ ID NO: 230, SEQ ID NO: 240 and/or SEQ ID NO: 276, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 2, SEQ ID NO: 30, SEQ ID NO: 60, SEQ ID NO: 132, SEQ ID NO: 222, SEQ ID NO: 230, SEQ ID NO: 240 and/or SEQ ID NO: 276.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 2, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 2. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 2, or a functional fragment thereof, and wherein the engineered pantothenate kinase comprises at least one substitution or substitution set at one or more positions selected from 54/240/277/281, 240, 240/277, 240/277/281, 240/277/281/282, 240/281, 240/281/282, 277, and 277/281, and wherein the amino acid positions of the polypeptide sequence are numbered with reference to SEQ ID NO: 2. In some additional embodiments, the engineered pantothenate kinase comprises at least one substitution or substitution set selected from 54S/240W/277M/281M, 240F, 240F/277I, 240F/277I/281L, 240F/277M, 240F/277M/281M, 240F/277M/281M/282M, 240F/281M, 240F/281M/282M, 240W/277I/281M, 240W/281M, 277I/281L, 277I/281M, 277M, and 277M/281M, wherein the amino acid positions of the polypeptide sequence are numbered with reference to SEQ ID NO: 2. In some additional embodiments, the engineered pantothenate kinase comprises at least one substitution or substitution set selected from I54S/Y240W/L277M/I281M, Y240F, Y240F/L277I, Y240F/L277I/I281L, Y240F/L277M, Y240F/L277M/I281M, Y240F/L277M/I281M/N282M, Y240F/I281M, Y240F/I281M/N282M, Y240W/L277I/I281M, Y240W/I281M, L277I/I281L, L277I/I281M, L277M, and L277M/I281M, wherein the amino acid positions of the polypeptide sequence are numbered with reference to SEQ ID NO: 2. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 2-1.

In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 2. In some additional embodiments, the engineered pantothenate kinase is a variant engineered polypeptide set forth in SEQ ID NO: 2.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 30, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 30. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 30, or a functional fragment thereof, and wherein the engineered pantothenate kinase comprises at least one substitution or substitution set at one or more positions selected from 13, 13/14/19/22, 13/14/22, 13/14/22/37, 13/14/22/106/247, 13/14/218/247/305, 13/19, 13/22, 15/26/283, 15/27, 15/27/283, 15/27/283/305, 15/27/305, 15/283, 19/22/26/69, 19/29, 20, 20/24, 20/24/25/69/75, 20/24/30/75, 20/70/75, 22/218, 22/218/271, 24, 24/30, 24/30/75, 24/75/86/134, 26, 26/29, 27, 27/78, 27/78/123/283, 27/283, 29, and 75, wherein the amino acid positions of the polypeptide sequences are numbered with reference to SEQ ID NO: 30. In some additional embodiments, the engineered pantothenate kinase comprises at least one substitution or substitution set selected from 13D, 13D/14E/19T/22G, 13D/14E/22G, 13D/14E/22G/37L, 13D/14E/22T/106A/247M, 13D/14E/218E/247M/305T, 13D/19T, 13D/22T, 15L/26L/283H, 15L/27N, 15L/27N/283H, 15L/27N/283L, 15L/27N/283L/305I, 15L/27N/305I, 15L/283L, 19R/22D/26P/69Y, 19R/29S, 20M, 20M/24A, 20M/24A/30R/75E, 20M/24S/25T/69T/75E, 20M/70D/75E, 22G/218E, 22G/218E/271S, 24A, 24A/30R, 24S/30R/75E, 24S/75E/86H/134L, 26L, 26P, 26P/29S, 27N, 27N/78A, 27N/78A/123W/283H, 27N/283H, 27N/283L, 29S, and 75E, wherein the amino acid positions of the polypeptide sequences are numbered with reference to SEQ ID NO: 30. In some additional embodiments, the engineered pantothenate kinase comprises at least one substitution or substitution set selected from L13D, L13D/Q14E/Q19T/A22G, L13D/Q14E/A22G, L13D/Q14E/A22G/A37L, L13D/Q14E/A22T/R106A/F247M, L13D/Q14E/F218E/F247M/A305T, L13D/Q19T, L13D/A22T, F15L/S26L/W283H, F15L/V27N, F15L/V27N/W283H, F15L/V27N/W283L, F15L/V27N/W283L/A305I, F15L/V27N/A305I, F15L/W283L, Q19R/A22D/S26P/N69Y, Q19R/M29S, W20M, W20M/R24A, W20M/R24A/T30R/V75E, W20M/R24S/D25T/N69T/V75E, W20M/L70D/V75E, A22G/F218E, A22G/F218E/I271S, R24A, R24A/T30R, R24S/T30R/V75E, R24S/V75E/R86H/Q134L, S26L, S26P, S26P/M29S, V27N, V27N/Q78A, V27N/Q78A/L123W/W283H, V27N/W283H, V27N/W283L, M29S, and V75E, wherein the amino acid positions of the polypeptide sequences are numbered with reference to SEQ ID NO: 30. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 4-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 30. In some additional embodiments, the engineered pantothenate kinase is a variant engineered polypeptide set forth in SEQ ID NO: 30.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 60, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 60. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 60, or a functional fragment thereof, and wherein the engineered pantothenate kinase comprises at least one substitution or substitution set at one or more positions selected from 14/19/41/157/161/261, 19/22/41/44/54/119/157/261/298/308, 19/22/54/157/169, 22/106/218, 41, 41/44/54/119/120/157/169/261, 41/44/54/119/120/157/261/298/308, 41/44/54/119/120/161/169/261/298, 41/44/54/119/298/305, 41/44/161/169/261, 41/44/169/261/298/308, 41/44/169/261/308, 41/54/119/157/169/261, 41/119/161/169/261/308, 41/119/161/308, 44/54/119/120/157/161/169, 44/54/119/120/157/161/261, 44/54/119/120/169/261, 44/54/119/157/161/261/298, 44/54/119/169, 44/76/119/157/161, 44/119/120/261, 44/119/157/161, 44/119/161/261/298, 44/157/161/169, 44/157/298, 44/261/298/308, 44/261/308, 54/119/157/161/169, 54/157/161/261/308, 119/157/161, 119/157/161/169/261, 119/169/261, 119/261/298/308, 120/157/261, 157, 157/161/169/261, 157/161/308, 157/169/261/298/308, 157/308, 250, 302, and 310, wherein the amino acid positions of the polypeptide sequences are numbered with reference to SEQ ID NO: 60. In some additional embodiments, the engineered pantothenate kinase comprises at least one substitution or substitution set selected from 14E/19T/41C/157M/161K/261P, 19A/22G/54V/157M/169Q, 19T/22G/41C/44P/54V/119A/157M/261G/298R/308I, 22G/106A/218E, 41C/44P/54W/119P/298R/305T, 41C/44P/161R/169Q/261G, 41C/44Q/54V/119A/1201K/157M/169Q/261P, 41C/44Q/54V/119P/120K/157M/261G/298R/308V, 41C/44Q/54V/119P/120K/161K/169Q/261G/298R, 41C/44Q/169Q/261P/298R/308V, 41C/44Q/169Q/261P/308V, 41C/54W/119P/157M/169Q/261G, 41C/119P/161R/169Q/261G/308V, 41C/119P/161R/308V, 41R, 44P/54V/119P/157M/161R/261P/298R, 44P/54W/119A/120K/169Q/261G, 44P/76Q/119P/157M/161K, 44P/119K/157M/161K, 44P/119P/120K/261P, 44P/157M/298R, 44Q/54V/119A/120K/157M/161R/169Q, 44Q/54V/119K/120K/157M/161R/261G, 44Q/54W/119P/169Q, 44Q/119P/161R/261P/298R, 44Q/157M/161K/169Q, 44Q/261G/298R/308V, 44Q/261P/308V, 54V/157M/161K/261G/308I, 54W/119A/157M/161K/169Q, 119K/157M/161R/169Q/261P, 119P/157M/161K, 119P/261G/298R/308I, 119Q/169Q/261G, 120K/157M/261P, 157M, 157M/161R/169Q/261G, 157M/161R/308V, 157M/169Q/261P/298R/308I, 157M/308V, 250R, 302A, and 310S, wherein the amino acid positions of the polypeptide sequences are numbered with reference to SEQ ID NO: 60. In some additional embodiments, the engineered pantothenate kinase comprises at least one substitution or substitution set selected from Q14E/Q19T/G41C/V157M/S161K/N261P, Q19A/A22G/I54V/V157M/N169Q, Q19T/A22G/G41C/E44P/I54V/R119A/V157M/N261G/S298R/A308I, A22G/R106A/F218E, G41C/E44P/I54W/R119P/S298R/A305T, G41C/E44P/S161R/N169Q/N261G, G41C/E44Q/I54V/R119A/R120K/V157M/N169Q/N261P, G41C/E44Q/I54V/R119P/R120K/V157M/N261G/5298R/A308V, G41C/E44Q/I54V/R119P/R120K/S161K/N169Q/N261G/S298R, G41C/E44Q/N169Q/N261P/S298R/A308V, G41C/E44Q/N169Q/N261P/A308V, G41C/I54W/R119P/V157M/N169Q/N261G, G41C/R119P/S161R/N169Q/N261G/A308V, G41C/R119P/S161R/A308V, G41R, E44P/I54V/R119P/V157M/S161R/N261P/S298R, E44P/I54W/R119A/R120K/N169Q/N261G, E44P/L76Q/R119P/V157M/S161K, E44P/R119K/V157M/S161K, E44P/R119P/R120K/N261P, E44P/V157M/S298R, E44Q/I54V/R119A/R120K/V157M/S161R/N169Q, E44Q/I54V/R119K/R120K/V157M/S161R/N261G, E44Q/I54W/R119P/N169Q, E44Q/R119P/S161R/N261P/S298R, E44Q/V157M/S161K/N169Q, E44Q/N261G/S298R/A308V, E44Q/N261P/A308V, I54V/V157M/S161K/N261G/A308I, I54W/R119A/V157M/S161K/N169Q, R119K/V157M/S161R/N169Q/N261P, R119P/V157M/S161K, R119P/N261G/5298R/A308I, R119Q/N169Q/N261G, R120K/V157M/N261P, V157M, V157M/S161R/N169Q/N261G, V157M/S161R/A308V, V157M/N169Q/N261P/S298R/A308I, V157M/A308V, G250R, T302A, and E310S, wherein the amino acid positions of the polypeptide sequences are numbered with reference to SEQ ID NO: 60. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 5-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 60. In some additional embodiments, the engineered pantothenate kinase is a variant engineered polypeptide set forth in SEQ ID NO: 60.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 132, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 132. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 132, or a functional fragment thereof, and wherein the engineered pantothenate kinase comprises at least one substitution or substitution set at one or more positions selected from 24/48, 64, 71, 123, 125, 134, and 180, wherein the amino acid positions of the polypeptide sequences are numbered with reference to SEQ ID NO: 132. In some additional embodiments, the engineered pantothenate kinase comprises at least one substitution or substitution set selected from 24A/48M, 64L, 71Q, 123H, 123W, 125G, 125S, 134R, and 180E, wherein the amino acid positions of the polypeptide sequences are numbered with reference to SEQ ID NO: 132. In some additional embodiments, the engineered pantothenate kinase comprises at least one substitution or substitution set selected from R24A/L48M, F64L, R71Q, L123H, L123W, T125G, T125S, Q134R, and Y180E, wherein the amino acid positions of the polypeptide sequences are numbered with reference to SEQ ID NO: 132. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 6-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 132. In some additional embodiments, the engineered pantothenate kinase is a variant engineered polypeptide set forth in SEQ ID NO: 132.

In some additional embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 132, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 132. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 132, or a functional fragment thereof, and wherein the engineered pantothenate kinase comprises at least one substitution or substitution set at one or more positions selected from 92/301, 125, and 180, wherein the amino acid positions of the polypeptide sequences are numbered with reference to SEQ ID NO: 132. In some additional embodiments, the engineered pantothenate kinase comprises at least one substitution or substitution set selected from 92G/301M, 125G, 125S, and 180E, wherein the amino acid positions of the polypeptide sequences are numbered with reference to SEQ ID NO: 132. In some additional embodiments, the engineered pantothenate kinase comprises at least one substitution or substitution set selected from S92G/L301M, T125G, T125S, and Y180E, wherein the amino acid positions of the polypeptide sequences are numbered with reference to SEQ ID NO: 132. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 6-2. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 132. In some additional embodiments, the engineered pantothenate kinase is a variant engineered polypeptide set forth in SEQ ID NO: 132.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 222, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 222. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 222, or a functional fragment thereof, and wherein the engineered pantothenate kinase comprises at least one substitution or substitution set at one or more positions selected from 83/84/305, 143, and 154, wherein the amino acid positions of the polypeptide sequences are numbered with reference to SEQ ID NO: 222. In some additional embodiments, the engineered pantothenate kinase comprises at least one substitution or substitution set selected from 83P/84H/305T, 143G, and 154P, wherein the amino acid positions of the polypeptide sequences are numbered with reference to SEQ ID NO: 222. In some additional embodiments, the engineered pantothenate kinase comprises at least one substitution or substitution set selected from N83P/G84H/A305T, K143G, and H154P, wherein the amino acid positions of the polypeptide sequences are numbered with reference to SEQ ID NO: 222. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 7-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 222. In some additional embodiments, the engineered pantothenate kinase is a variant engineered polypeptide set forth in SEQ ID NO: 222.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 230, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 230. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 230, or a functional fragment thereof, and wherein the engineered pantothenate kinase comprises at least one substitution or substitution set at one or more positions selected from 13/169/213/247/283/288, 16/247, 49/247, 64/104/154/284, 75/104/284, 169/247, and 247, wherein the amino acid positions of the polypeptide sequences are numbered with reference to SEQ ID NO: 230. In some additional embodiments, the engineered pantothenate kinase comprises at least one substitution or substitution set selected from 13H/169S/213E/247L/283S/288T, 16E/247L, 49D/247L, 64I/104F/154P/284V, 75Q/104F/284V, 169S/247L, and 247L, wherein the amino acid positions of the polypeptide sequences are numbered with reference to SEQ ID NO: 230. In some additional embodiments, the engineered pantothenate kinase comprises at least one substitution or substitution set selected from L13H/N169S/D213E/F247L/H283S/Q288T, D16E/F247L, E49D/F247L, F64I/T104F/H154P/L284V, V75Q/T104F/L284V, N169S/F247L, and F247L, wherein the amino acid positions of the polypeptide sequences are numbered with reference to SEQ ID NO: 230. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 8-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 230. In some additional embodiments, the engineered pantothenate kinase is a variant engineered polypeptide set forth in SEQ ID NO: 230.

In some additional embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 240, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 240. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 240, or a functional fragment thereof, and wherein the engineered pantothenate kinase comprises at least one substitution or substitution set at one or more positions selected from 8, 8/13/14/83/247, 8/64/213/247, 8/64/247, 8/247/283, 10, and 264/276, wherein the amino acid positions of the polypeptide sequences are numbered with reference to SEQ ID NO: 240. In some additional embodiments, the engineered pantothenate kinase comprises at least one substitution or substitution set selected from 8E/13H/14A/83P/247L, 8E/64I/213E/247L, 8E/64I/247L, 8E/247L/283S, 8W, 10S, and 264R/276S, wherein the amino acid positions of the polypeptide sequences are numbered with reference to SEQ ID NO: 240. In some additional embodiments, the engineered pantothenate kinase comprises at least one substitution or substitution set selected from L8E/L13H/Q14A/N83P/F247L, L8E/F64I/D213E/F247L, L8E/F64I/F247L, L8E/F247L/H283S, L8W, T10S, and K264R/T276S, wherein the amino acid positions of the polypeptide sequences are numbered with reference to SEQ ID NO: 240. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 9-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 240. In some additional embodiments, the engineered pantothenate kinase is a variant engineered polypeptide set forth in SEQ ID NO: 240.

In some embodiments, the present invention provides engineered pantothenate kinases comprising polypeptide sequences having at least 85%, 86%, 87%, 88%, 89%, 90%, 91%, 92%, 93%, 94%, 95%, 96%, 97%, 98%, 99%, or more sequence identity to SEQ ID NO: 276, or a functional fragment thereof, wherein the engineered pantothenate kinases comprise at least one substitution or substitution set in the polypeptide sequences, and wherein the amino acid positions of the polypeptide sequences are numbered with reference to SEQ ID NO: 276. In some embodiments, the engineered pantothenate kinase comprises a polypeptide sequence having at least 85%, 86%, 87%, 88%, 89%, 90%, 91%, 92%, 93%, 94%, 95%, 96%, 97%, 98%, 99%, or more sequence identity to SEQ ID NO: 276, or a functional fragment thereof, and wherein the engineered pantothenate kinase comprises at least one substitution or substitution set at one or more positions selected from 11/13/23/61/85/304, 13/19/61, 23/61, and 23/61/304, wherein the amino acid positions of the polypeptide sequences are numbered with reference to SEQ ID NO: 276. In some additional embodiments, the engineered pantothenate kinase comprises at least one substitution or substitution set selected from 11Q/13R/23V/61V/85V/304G, 13R/19T/61I, 23V/61I/304G, and 23V/61V, wherein the amino acid positions of the polypeptide sequences are numbered with reference to SEQ ID NO: 276. In some additional embodiments, the engineered pantothenate kinase comprises at least one substitution or substitution set selected from P11Q/L13R/L23V/L61V/Q85V/S304G, L13R/Q19T/L61I, L23V/L61I/S304G, and L23V/L61V, wherein the amino acid positions of the polypeptide sequences are numbered with reference to SEQ ID NO: 276. In some embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in Table 10-1. In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to SEQ ID NO: 276. In some additional embodiments, the engineered pantothenate kinase is a variant engineered polypeptide set forth in SEQ ID NO: 276.

In some further embodiments, the engineered pantothenate kinase comprises a polypeptide sequence that is at least 85%, 86%, 87%, 88%, 89%, 90%, 91%, 92%, 93%, 94%, 95%, 96%, 97%, 98%, 99% or more identical to the sequence of at least one engineered pantothenate kinase variant set forth in the even numbered sequences of SEQ ID NOS: 2-270. In some additional embodiments, the engineered pantothenate kinase comprises a polypeptide sequence forth in the even numbered sequences of SEQ ID NOS: 2-270. In some further embodiments, the engineered pantothenate kinase comprises at least one improved property compared to wild-type *E. coli* pantothenate kinase. In still some additional embodiments, the improved property comprises improved activity on a substrate, as compared to a wild-type pantothenate kinase. In some further embodiments, the substrate comprises 2,4-dinitrophenylhydrazine and at least one aldehyde. In some additional embodiments, the improved property comprises improved production of phospho-ethynyl glyceraldehyde, as compared to a wild-type pantothenate kinase. In some further embodiments, the engineered pantothenate kinase is purified. The present invention also provides compositions comprising at least one engineered pantothenate kinase provided herein. In some embodiments, the present invention provides compositions comprising one engineered pantothenate kinase provided herein.

The present invention also provides polynucleotide sequences encoding at least one engineered pantothenate kinase provided herein. In some embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 1, SEQ ID NO: 29, SEQ ID NO: 59, SEQ ID NO: 131, SEQ ID NO: 221, SEQ ID NO: 229, SEQ ID NO: 239, and/or SEQ ID NO: 275. In some embodiments, the polynucleotide sequence of the engineered pantothenate kinase comprises at least one substitution at one or more positions. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 1, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 29, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 59, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 131, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 221, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 229, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 239, or a functional fragment thereof. In some further embodiments, the polynucleotide sequence encoding at least one engineered pantothenate kinase comprises at least 85%, 86%, 87%, 88%, 89%, 90%, 91%, 92%, 93%, 94%, 95%, 96%, 97%, 98%, 99%, or more sequence identity to SEQ ID NO: 275, or a functional fragment thereof. In some additional embodiments, the polynucleotide sequence is operably linked to a control sequence. In some embodiments, the polynucleotide sequence is codon optimized. In some further embodiments, the polynucleotide comprises an odd-numbered sequence of SEQ ID NOS: 1-269. The present invention also provides expression vectors comprising at least one polynucleotide sequence encoding a pantothenate kinase provided herein. In some embodiments, the expression vectors comprise one polynucleotide sequence encoding a pantothenate kinase provided herein. The present invention also provides host cells comprising at least one expression vector provided herein. The present invention also provides host cells comprising at least one polynucleotide sequence encoding a pantothenate kinase provided herein.

The present invention also provides methods of producing an engineered pantothenate kinase in a host cell, comprising culturing the host cell provided herein, under suitable conditions, such that at least one engineered pantothenate kinase is produced. In some embodiments, the methods further comprise recovering at least one engineered pantothenate kinase from the culture and/or host cell. In some additional embodiments, the methods further comprise the step of purifying the at least one engineered pantothenate kinase.

DESCRIPTION OF THE INVENTION

The present invention provides engineered pantothenate kinase (PanK) enzymes, polypeptides having PanK activity, and polynucleotides encoding these enzymes, as well as vectors and host cells comprising these polynucleotides and polypeptides. Methods for producing PanK enzymes are also provided. The present invention further provides compositions comprising the PanK enzymes and methods of using the engineered PanK enzymes. The present invention finds particular use in the production of pharmaceutical compounds.

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the invention as a whole.

It is to be understood that both the foregoing general description and the following detailed description are exemplary and explanatory only and are not restrictive of the present invention. The section headings used herein are for organizational purposes only and not to be construed as limiting the subject matter described. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Abbreviations

The abbreviations used for the genetically encoded amino acids are conventional and are as follows: alanine (Ala or A), arginine (Arg or R), asparagine (Asn or N), aspartate (Asp or D), cysteine (Cys or C), glutamate (Glu or E), glutamine (Gln or Q), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleosides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

Definitions

In reference to the present invention, the technical and scientific terms used in the descriptions herein will have the meanings commonly understood by one of ordinary skill in the art, unless specifically defined otherwise. Accordingly, the following terms are intended to have the following meanings.

As used herein, the singular forms "a", "an" and "the" include plural referents unless the context clearly indicates otherwise. Thus, for example, reference to "a polypeptide" includes more than one polypeptide.

Similarly, "comprise," "comprises," "comprising" "include," "includes," and "including" are interchangeable and not intended to be limiting. Thus, as used herein, the term "comprising" and its cognates are used in their inclusive sense (i.e., equivalent to the term "including" and its corresponding cognates).

It is to be further understood that where descriptions of various embodiments use the term "comprising," those skilled in the art would understand that in some specific instances, an embodiment can be alternatively described using language "consisting essentially of" or "consisting of."

As used herein, the term "about" means an acceptable error for a particular value. In some instances "about" means within 0.05%, 0.5%, 1.0%, or 2.0%, of a given value range. In some instances, "about" means within 1, 2, 3, or 4 standard deviations of a given value.

As used herein, "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

As used herein, "ATCC" refers to the American Type Culture Collection whose biorepository collection includes genes and strains.

As used herein, "NCBI" refers to National Center for Biological Information and the sequence databases provided therein.

As used herein, "pantothenate kinase," "PanK," refer to enzymes (EC 2.7.1.33), that phosphorylate pantothenate to form 4'-phosphopantothenate or variant enzymes derived from such PanK enzymes, whether or not such variant enzymes retain the same functionality as the source (i.e., "parent") enzyme.

"Protein," "polypeptide," and "peptide" are used interchangeably herein to denote a polymer of at least two amino acids covalently linked by an amide bond, regardless of length or post-translational modification (e.g., glycosylation or phosphorylation). Included within this definition are D- and L-amino acids, and mixtures of D- and L-amino acids, as well as polymers comprising D- and L-amino acids, and mixtures of D- and L-amino acids.

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

As used herein, "hydrophilic amino acid or residue" refers to an amino acid or residue having a side chain exhibiting a hydrophobicity of less than zero according to the normalized consensus hydrophobicity scale of Eisenberg et al., (Eisenberg et al., J. Mol. Biol., 179:125-142 [1984]). Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

As used herein, "acidic amino acid or residue" refers to a hydrophilic amino acid or residue having a side chain exhibiting a pKa value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

As used herein, "basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

As used herein, "polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

As used herein, "hydrophobic amino acid or residue" refers to an amino acid or residue having a side chain exhibiting a hydrophobicity of greater than zero according to the normalized consensus hydrophobicity scale of Eisenberg et al., (Eisenberg et al., J. Mol. Biol., 179:125-142 [1984]). Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

As used herein, "aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

As used herein, "constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five membered ring.

As used herein, "non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

As used herein, "aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I). It is noted that cysteine (or "L-Cys" or "[C]") is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure, L-Cys (C) is categorized into its own unique group.

As used herein, "small amino acid or residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

As used herein, "hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

As used herein, "polynucleotide" and "nucleic acid' refer to two or more nucleotides that are covalently linked together. The polynucleotide may be wholly comprised of ribonucleotides (i.e., RNA), wholly comprised of 2' deoxyribonucleotides (i.e., DNA), or comprised of mixtures of ribo- and 2' deoxyribonucleotides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. In some embodiments, such modified or synthetic nucleobases are nucleobases encoding amino acid sequences.

As used herein, “nucleoside” refers to glycosylamines comprising a nucleobase (i.e., a nitrogenous base), and a 5-carbon sugar (e.g., ribose or deoxyribose). Non-limiting examples of nucleosides include cytidine, uridine, adenosine, guanosine, thymidine, and inosine. In contrast, the term “nucleotide” refers to the glycosylamines comprising a nucleobase, a 5-carbon sugar, and one or more phosphate groups. In some embodiments, nucleosides can be phosphorylated by kinases to produce nucleotides.

As used herein, “nucleoside diphosphate” refers to glycosylamines comprising a nucleobase (i.e., a nitrogenous base), a 5-carbon sugar (e.g., ribose or deoxyribose), and a diphosphate (i.e., pyrophosphate) moiety. In some embodiments herein, “nucleoside diphosphate” is abbreviated as “NDP.” Non-limiting examples of nucleoside diphosphates include cytidine diphosphate (CDP), uridine diphosphate (UDP), adenosine diphosphate (ADP), guanosine diphosphate (GDP), thymidine diphosphate (TDP), and inosine diphosphate (IDP). The terms “nucleoside” and “nucleotide” may be used interchangeably in some contexts.

As used herein, “coding sequence” refers to that portion of a nucleic acid (e.g., a gene) that encodes an amino acid sequence of a protein.

As used herein, the terms “biocatalysis,” “biocatalytic,” “biotransformation,” and “biosynthesis” refer to the use of enzymes to perform chemical reactions on organic compounds.

As used herein, “wild-type” and “naturally-occurring” refer to the form found in nature. For example a wild-type polypeptide or polynucleotide sequence is a sequence present in an organism that can be isolated from a source in nature and which has not been intentionally modified by human manipulation.

As used herein, “recombinant,” “engineered,” “variant,” and “non-naturally occurring” when used with reference to a cell, nucleic acid, or polypeptide, refers to a material, or a material corresponding to the natural or native form of the material, that has been modified in a manner that would not otherwise exist in nature. In some embodiments, the cell, nucleic acid or polypeptide is identical a naturally occurring cell, nucleic acid or polypeptide, but is produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

The term “percent (%) sequence identity” is used herein to refer to comparisons among polynucleotides or polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted by any suitable method, including, but not limited to the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See Altschul et al., J. Mol. Biol., 215: 403-410 [1990]; and Altschul et al., Nucl. Acids Res., 3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always $>0$) and N (penalty score for mismatching residues; always $<0$). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

As used herein, “reference sequence” refers to a defined sequence used as a basis for a sequence and/or activity comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence.

As used herein, "comparison window" refers to a conceptual segment of at least about 20 contiguous nucleotide positions or amino acid residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "corresponding to," "reference to," and "relative to" when used in the context of the numbering of a given amino acid or polynucleotide sequence refer to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered pantothenate kinase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

As used herein, "substantial identity" refers to a polynucleotide or polypeptide sequence that has at least 80 percent sequence identity, at least 85 percent identity, at least between 89 to 95 percent sequence identity, or more usually, at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In some specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). In some embodiments, residue positions that are not identical in sequences being compared differ by conservative amino acid substitutions.

As used herein, "amino acid difference" and "residue difference" refer to a difference in the amino acid residue at a position of a polypeptide sequence relative to the amino acid residue at a corresponding position in a reference sequence. In some cases, the reference sequence has a histidine tag, but the numbering is maintained relative to the equivalent reference sequence without the histidine tag. The positions of amino acid differences generally are referred to herein as "Xn," where n refers to the corresponding position in the reference sequence upon which the residue difference is based. For example, a "residue difference at position X93 as compared to SEQ ID NO: 4" refers to a difference of the amino acid residue at the polypeptide position corresponding to position 93 of SEQ ID NO: 4. Thus, if the reference polypeptide of SEQ ID NO: 4 has a serine at position 93, then a "residue difference at position X93 as compared to SEQ ID NO: 4" an amino acid substitution of any residue other than serine at the position of the polypeptide corresponding to position 93 of SEQ ID NO: 4. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in the Table presented in the Examples), the present invention also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present invention can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "I" (e.g., X307H/X307P or X307H/P). The slash may also be used to indicate multiple substitutions within a given variant (i.e., there is more than one substitution present in a given sequence, such as in a combinatorial variant). In some embodiments, the present invention includes engineered polypeptide sequences comprising one or more amino acid differences comprising conservative or non-conservative amino acid substitutions. In some additional embodiments, the present invention provides engineered polypeptide sequences comprising both conservative and non-conservative amino acid substitutions.

As used herein, "conservative amino acid substitution" refers to a substitution of a residue with a different residue having a similar side chain, and thus typically involves substitution of the amino acid in the polypeptide with amino acids within the same or similar defined class of amino acids. By way of example and not limitation, in some embodiments, an amino acid with an aliphatic side chain is substituted with another aliphatic amino acid (e.g., alanine, valine, leucine, and isoleucine); an amino acid with an hydroxyl side chain is substituted with another amino acid with an hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively.

As used herein, "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered pantothenate kinase enzyme. Deletions can be directed to the internal portions and/or terminal portions of the polypeptide. In various embodiments, the deletion can comprise a continuous segment or can be discontinuous. Deletions are typically indicated by "–" in amino acid sequences.

As used herein, "insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant pantothenate kinases listed in the Tables provided in the Examples A "functional fragment" and "biologically active fragment" are used interchangeably herein to refer to a polypeptide that has an amino-terminal and/or carboxy-terminal deletion(s) and/or internal deletions, but where the remaining amino acid sequence is identical to the corresponding positions in the sequence to which it is being compared (e.g., a full-length engineered pantothenate kinase of the present invention) and that retains substantially all of the activity of the full-length polypeptide.

As used herein, "isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., within a host cell or via in vitro synthesis). The recombinant pantothenate kinase polypeptides may be present within a cell, present in the cellular medium, or prepared in various forms, such as lysates or isolated preparations. As such, in some embodiments, the recombinant pantothenate kinase polypeptides can be an isolated polypeptide.

As used herein, "substantially pure polypeptide" or "purified protein" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. However, in some embodiments, the composition comprising pantothenate kinase comprises pantothenate kinase that is less than 50% pure (e.g., about 10%, about 20%, about 30%, about 40%, or about 50%) Generally, a substantially pure pantothenate kinase composition comprises about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant pantothenate kinase polypeptides are substantially pure polypeptide compositions.

As used herein, "improved enzyme property" refers to at least one improved property of an enzyme. In some embodiments, the present invention provides engineered pantothenate kinase polypeptides that exhibit an improvement in any enzyme property as compared to a reference pantothenate kinase polypeptide and/or a wild-type pantothenate kinase polypeptide, and/or another engineered pantothenate kinase polypeptide. Thus, the level of "improvement" can be determined and compared between various pantothenate kinase polypeptides, including wild-type, as well as engineered pantothenate kinases. Improved properties include, but are not limited, to such properties as increased protein expression, increased thermoactivity, increased thermostability, increased pH activity, increased stability, increased enzymatic activity, increased substrate specificity or affinity, increased specific activity, increased resistance to substrate or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, and altered temperature profile. In additional embodiments, the term is used in reference to the at least one improved property of pantothenate kinase enzymes. In some embodiments, the present invention provides engineered pantothenate kinase polypeptides that exhibit an improvement in any enzyme property as compared to a reference pantothenate kinase polypeptide and/or a wild-type pantothenate kinase polypeptide, and/or another engineered pantothenate kinase polypeptide. Thus, the level of "improvement" can be determined and compared between various pantothenate kinase polypeptides, including wild-type, as well as engineered pantothenate kinases.

As used herein, "increased enzymatic activity" and "enhanced catalytic activity" refer to an improved property of the engineered polypeptides, which can be represented by an increase in specific activity (e.g., product produced/time/weight protein) or an increase in percent conversion of the substrate to the product (e.g., percent conversion of starting amount of substrate to product in a specified time period using a specified amount of enzyme) as compared to the reference enzyme. In some embodiments, the terms refer to an improved property of engineered pantothenate kinase polypeptides provided herein, which can be represented by an increase in specific activity (e.g., product produced/time/weight protein) or an increase in percent conversion of the substrate to the product (e.g., percent conversion of starting amount of substrate to product in a specified time period using a specified amount of pantothenate kinase) as compared to the reference pantothenate kinase enzyme. In some embodiments, the terms are used in reference to improved pantothenate kinase enzymes provided herein. Exemplary methods to determine enzyme activity of the engineered pantothenate kinases of the present invention are provided in the Examples. Any property relating to enzyme activity may be affected, including the classical enzyme properties of Km, Vmax or kcat, changes of which can lead to increased enzymatic activity. For example, improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring pantothenate kinase or another engineered pantothenate kinase from which the pantothenate kinase polypeptides were derived.

As used herein, "conversion" refers to the enzymatic conversion (or biotransformation) of a substrate(s) to the corresponding product(s). "Percent conversion" refers to the percent of the substrate that is converted to the product within a period of time under specified conditions. Thus, the "enzymatic activity" or "activity" of a pantothenate kinase polypeptide can be expressed as "percent conversion" of the substrate to the product in a specific period of time.

Enzymes with "generalist properties" (or "generalist enzymes") refer to enzymes that exhibit improved activity for a wide range of substrates, as compared to a parental sequence. Generalist enzymes do not necessarily demonstrate improved activity for every possible substrate. In some embodiments, the present invention provides pantothenate kinase variants with generalist properties, in that they demonstrate similar or improved activity relative to the parental gene for a wide range of sterically and electronically diverse substrates. In addition, the generalist enzymes provided herein were engineered to be improved across a wide range of diverse molecules to increase the production of metabolites/products.

The term "stringent hybridization conditions" is used herein to refer to conditions under which nucleic acid hybrids are stable. As known to those of skill in the art, the stability of hybrids is reflected in the melting temperature (Tm) of the hybrids. In general, the stability of a hybrid is a function of ion strength, temperature, G/C content, and the presence of chaotropic agents. The Tm values for polynucleotides can be calculated using known methods for predicting melting temperatures (See e.g., Baldino et al., Meth. Enzymol., 168:761-777 [1989]; Bolton et al., Proc. Natl. Acad. Sci. USA 48:1390 [1962]; Bresslauer et al., Proc. Natl. Acad. Sci. USA 83:8893-8897 [1986]; Freier et al., Proc. Natl. Acad. Sci. USA 83:9373-9377 [1986]; Kierzek et al., Biochem., 25:7840-7846 [1986]; Rychlik et al., Nucl. Acids Res., 18:6409-6412 [1990] (erratum, Nucl. Acids Res., 19:698 [1991]); Sambrook et al., supra); Suggs et al., 1981, in Developmental Biology Using Purified Genes, Brown et al. [eds.], pp. 683-693, Academic Press, Cambridge, Mass. [1981]; and Wetmur, Crit. Rev. Biochem. Mol. Biol. 26:227-259 [1991]). In some embodiments, the polynucleotide encodes the polypeptide disclosed herein and hybridizes under defined conditions, such as moderately stringent or highly stringent conditions, to the complement of a sequence encoding an engineered pantothenate kinase enzyme of the present invention.

As used herein, "hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature Tm as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w/v) SDS at 65° C. and washing in 0.1×SSC containing 0.1% SDS at 65° C. Other high stringency hybridization conditions, as well as moderately stringent conditions, are described in the references cited above.

As used herein, "codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the pantothenate kinase enzymes may be codon optimized for optimal production in the host organism selected for expression.

As used herein, "preferred," "optimal," and "high codon usage bias" codons when used alone or in combination refer(s) interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See e.g., GCG CodonPreference, Genetics Computer Group Wisconsin Package; CodonW, Peden, University of Nottingham; McInerney, Bioinform., 14:372-73 [1998]; Stenico et al., Nucl. Acids Res., 222437-46 [1994]; and Wright, Gene 87:23-29 [1990]). Codon usage tables are available for many different organisms (See e.g., Wada et al., Nucl. Acids Res., 20:2111-2118 [1992]; Nakamura et al., Nucl. Acids Res., 28:292 [2000]; Duret, et al., supra; Henaut and Danchin, in *Escherichia coli* and *Salmonella*, Neidhardt, et al. (eds.), ASM Press, Washington D.C., p. 2047-2066 [1996]). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (See e.g., Mount, Bioinformatics: Sequence and Genome Analysis, Chapter 8, Cold Spring Harbor Laboratory Press, Cold Spring Harbor, N.Y. [2001]; Uberbacher, Meth. Enzymol., 266:259-281 [1996]; and Tiwari et al., Comput. Appl. Biosci., 13:263-270 [1997]).

As used herein, "control sequence" includes all components, which are necessary or advantageous for the expression of a polynucleotide and/or polypeptide of the present invention. Each control sequence may be native or foreign to the nucleic acid sequence encoding the polypeptide. Such control sequences include, but are not limited to, a leader, polyadenylation sequence, propeptide sequence, promoter sequence, signal peptide sequence, initiation sequence and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

The phrase "suitable reaction conditions" refers to those conditions in the enzymatic conversion reaction solution (e.g., ranges of enzyme loading, substrate loading, temperature, pH, buffers, co-solvents, etc.) under which a pantothenate kinase polypeptide of the present invention is capable of converting a substrate to the desired product compound. Some exemplary "suitable reaction conditions" are provided herein.

As used herein, "loading," such as in "compound loading" or "enzyme loading" refers to the concentration or amount of a component in a reaction mixture at the start of the reaction.

As used herein, "substrate" in the context of an enzymatic conversion reaction process refers to the compound or molecule acted on by the engineered enzymes provided herein (e.g., engineered pantothenate kinase polypeptides).

As used herein, "increasing" yield of a product (e.g., a deoxyribose phosphate analog) from a reaction occurs when a particular component present during the reaction (e.g., a pantothenate kinase enzyme) causes more product to be produced, compared with a reaction conducted under the same conditions with the same substrate and other substituents, but in the absence of the component of interest.

A reaction is said to be "substantially free" of a particular enzyme if the amount of that enzyme compared with other enzymes that participate in catalyzing the reaction is less than about 2%, about 1%, or about 0.1% (wt/wt).

As used herein, "fractionating" a liquid (e.g., a culture broth) means applying a separation process (e.g., salt precipitation, column chromatography, size exclusion, and filtration) or a combination of such processes to provide a solution in which a desired protein comprises a greater percentage of total protein in the solution than in the initial liquid product.

As used herein, "starting composition" refers to any composition that comprises at least one substrate. In some embodiments, the starting composition comprises any suitable substrate.

As used herein, "product" in the context of an enzymatic conversion process refers to the compound or molecule resulting from the action of an enzymatic polypeptide on a substrate.

As used herein, "equilibration" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

As used herein, "alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis (e.g., (C1-C4)alkyl refers to an alkyl of 1 to 4 carbon atoms).

As used herein, "alkenyl" refers to groups of from 2 to 12 carbon atoms inclusively, either straight or branched containing at least one double bond but optionally containing more than one double bond.

As used herein, "alkynyl" refers to groups of from 2 to 12 carbon atoms inclusively, either straight or branched containing at least one triple bond but optionally containing more than one triple bond, and additionally optionally containing one or more double bonded moieties.

As used herein, "heteroalkyl, "heteroalkenyl," and heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —NRα—, —PH—, —S(O)—, —S(O)2, —S(O) NRα-, —S(O) 2NRα-, and the like, including combinations thereof, where each Rα is independently selected from hydrogen, alkyl, heteroalkyl, cycloalkyl, heterocycloalkyl, aryl, and heteroaryl.

As used herein, "alkoxy" refers to the group —ORβ wherein R β is an alkyl group is as defined above including optionally substituted alkyl groups as also defined herein.

As used herein, "aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

As used herein, "amino" refers to the group —NH2. Substituted amino refers to the group —NHRδ, NRδRδ, and NRδRδRδ, where each Rδ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylysulfonylamino, furanyl-oxy-sulfamino, and the like.

As used herein, "oxo" refers to ═O.

As used herein, "oxy" refers to a divalent group —O—, which may have various substituents to form different oxy groups, including ethers and esters.

As used herein, "carboxy" refers to —COOH.

As used herein, "carbonyl" refers to —C(O)—, which may have a variety of substituents to form different carbonyl groups including acids, acid halides, aldehydes, amides, esters, and ketones.

As used herein, "alkyloxycarbonyl" refers to —C(O) ORE, where RE is an alkyl group as defined herein, which can be optionally substituted.

As used herein, "aminocarbonyl" refers to —C(O)NH2. Substituted aminocarbonyl refers to —C(O)NRδRδ, where the amino group NRδRδ is as defined herein.

As used herein, "halogen" and "halo" refer to fluoro, chloro, bromo and iodo.

As used herein, "hydroxy" refers to —OH.

As used herein, "cyano" refers to —CN.

As used herein, "heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

As used herein, "heteroarylalkyl" refers to an alkyl substituted with a heteroaryl (i.e., heteroaryl-alkyl-groups), preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

As used herein, "heteroarylalkenyl" refers to an alkenyl substituted with a heteroaryl (i.e., heteroaryl-alkenyl-groups), preferably having from 2 to 6 carbon atoms inclusively in the alkenyl moiety and from 5 to 12 ring atoms inclusively in the heteroaryl moiety.

As used herein, "heteroarylalkynyl" refers to an alkynyl substituted with a heteroaryl (i.e., heteroaryl-alkynyl-groups), preferably having from 2 to 6 carbon atoms inclusively in the alkynyl moiety and from 5 to 12 ring atoms inclusively in the heteroaryl moiety.

As used herein, "heterocycle," "heterocyclic," and interchangeably "heterocycloalkyl," refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

As used herein, "membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

As used herein the term "culturing" refers to the growing of a population of microbial cells under any suitable conditions (e.g., using a liquid, gel or solid medium).

Recombinant polypeptides can be produced using any suitable methods known in the art. Genes encoding the wild-type polypeptide of interest can be cloned in vectors, such as plasmids, and expressed in desired hosts, such as *E. coli*, etc. Variants of recombinant polypeptides can be generated by various methods known in the art. Indeed, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Mutagenesis and directed evolution methods can be readily applied to enzyme-encoding polynucleotides to generate variant libraries that can be expressed, screened, and assayed. Any suitable mutagenesis and directed evolution methods find use in the present invention and are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, and all related US, as well as PCT and non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, the enzyme clones obtained following mutagenesis treatment are screened by subjecting the enzyme preparations to a defined temperature (or other assay conditions) and measuring the amount of enzyme activity remaining after heat treatments or other suitable assay conditions. Clones containing a polynucleotide encoding a polypeptide are then isolated from the gene, sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

After the variants are produced, they can be screened for any desired property (e.g., high or increased activity, or low or reduced activity, increased thermal activity, increased thermal stability, and/or acidic pH stability, etc.). In some embodiments, "recombinant pantothenate kinase polypeptides" (also referred to herein as "engineered pantothenate kinase polypeptides," "variant pantothenate kinase enzymes," "pantothenate kinase variants," and "pantothenate kinase combinatorial variants") find use. In some embodiments, "recombinant pantothenate kinase polypeptides" (also referred to as "engineered pantothenate kinase polypeptides," "variant pantothenate kinase enzymes," "pantothenate kinase variants," and "pantothenate kinase combinatorial variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature. For example a "heterologous polynucleotide" is any polynucleotide that is introduced into a host cell by laboratory techniques, and includes polynucleotides that are removed from a host cell, subjected to laboratory manipulation, and then reintroduced into a host cell.

As used herein, the terms "host cell" and "host strain" refer to suitable hosts for expression vectors comprising DNA provided herein (e.g., the polynucleotides encoding the pantothenate kinase variants). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues means polypeptides that contain one or more non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

As used herein, "stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess ("e.e.") calculated therefrom according to the formula [major enantiomer −minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess ("d.e."). Enantiomeric excess and diastereomeric excess are types of stereomeric excess.

As used herein, "regioselectivity" and "regioselective reaction" refer to a reaction in which one direction of bond making or breaking occurs preferentially over all other possible directions. Reactions can completely (100%) regioselective if the discrimination is complete, substantially regioselective (at least 75%), or partially regioselective (x %, wherein the percentage is set dependent upon the reaction of interest), if the product of reaction at one site predominates over the product of reaction at other sites.

As used herein, "chemoselectivity" refers to the preferential formation in a chemical or enzymatic reaction of one product over another.

As used herein, "pH stable" refers to a pantothenate kinase polypeptide that maintains similar activity (e.g., more than 60% to 80%) after exposure to high or low pH (e.g., 4.5-6 or 8 to 12) for a period of time (e.g., 0.5-24 hrs) compared to the untreated enzyme.

As used herein, "thermostable" refers to a pantothenate kinase polypeptide that maintains similar activity (more than 60% to 80% for example) after exposure to elevated temperatures (e.g., 40-80° C.) for a period of time (e.g., 0.5-24 h) compared to the wild-type enzyme exposed to the same elevated temperature.

As used herein, "solvent stable" refers to a pantothenate kinase polypeptide that maintains similar activity (more than e.g., 60% to 80%) after exposure to varying concentrations (e.g., 5-99%) of solvent (ethanol, isopropyl alcohol, dimethylsulfoxide [DMSO], tetrahydrofuran, 2-methyltetrahydrofuran, acetone, toluene, butyl acetate, methyl tert-butyl ether, etc.) for a period of time (e.g., 0.5-24 h) compared to the wild-type enzyme exposed to the same concentration of the same solvent.

As used herein, "thermo- and solvent stable" refers to a pantothenate kinase polypeptide that is both thermostable and solvent stable.

As used herein, "optional" and "optionally" mean that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included.

As used herein, "optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

DETAILED DESCRIPTION OF THE INVENTION

The present invention provides engineered pantothenate kinase (PanK) enzymes, polypeptides having PanK activity, and the polynucleotides encoding these enzymes, as well as the vectors and host cells comprising these polynucleotides and polypeptides. Methods for producing PanK enzymes are also provided. The present invention further provides compositions comprising the PanK enzymes and methods of using the engineered PanK enzymes. The present invention finds particular use in the production of pharmaceutical compounds.

In some embodiments, the present invention provides enzymes suitable for the production of phosphorylated glycerol derivatives and glyceraldehyde derivatives with bulky substituents on the C2 carbon of glycerol, especially phosphorylated ethynyl-glycerols and ethynyl-glyceraldehydes that are intermediates for the in vitro enzymatic synthesis of the non-natural nucleoside analog shown of compound (1).

Compound (1)

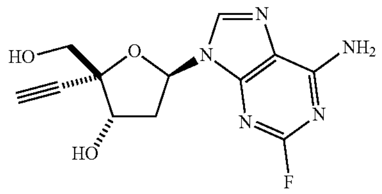

Production of phosphorylated glyceraldehyde derivatives such as compound (5), can be difficult. However, the corresponding non-phosphorylated glyceraldehyde derivatives (6) can be made by oxidizing the glycerol derivative (7) with an alcohol oxidase. Once the glycerol aldehyde is formed it can be phosphorylated into the desired intermediate (5) by PanK as shown in Scheme I.

Scheme I

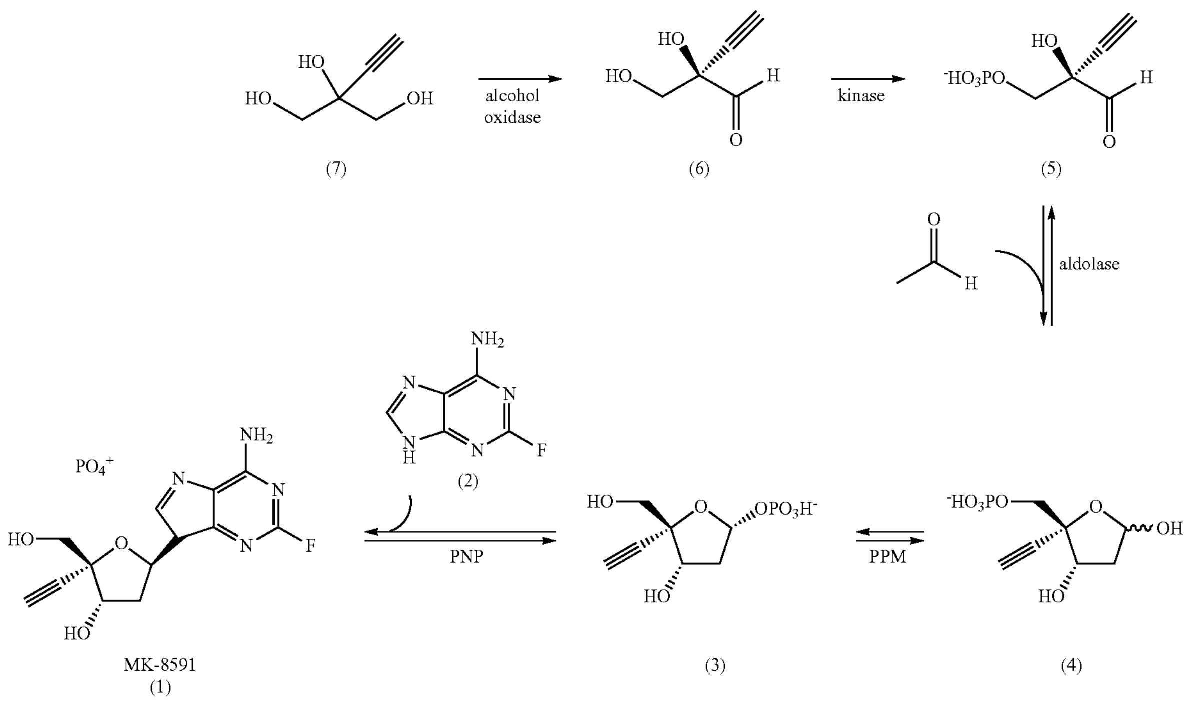

Engineered PanK Polypeptides

The present invention provides engineered PanK polypeptides, polynucleotides encoding the polypeptides, methods of preparing the polypeptides, and methods for using the polypeptides. Where the description relates to polypeptides, it is to be understood that it also describes the polynucleotides encoding the polypeptides. In some embodiments, the present invention provides engineered, non-naturally occurring PanK enzymes with improved properties as compared to wild-type PanK enzymes. Any suitable reaction conditions find use in the present invention. In some embodiments, methods are used to analyze the improved properties of the engineered polypeptides to carry out the isomerization reaction. In some embodiments, the reaction conditions are modified with regard to concentrations or amounts of engineered PanK, substrate(s), buffer(s), solvent(s), co-factors, pH, conditions including temperature and reaction time, and/or conditions with the engineered PanK polypeptide immobilized on a solid support, as further described below and in the Examples.

In some embodiments, additional reaction components or additional techniques are utilized to supplement the reaction conditions. In some embodiments, these include taking measures to stabilize or prevent inactivation of the enzyme, reduce product inhibition, shift reaction equilibrium to desired product formation.

In some further embodiments, any of the above described process for the conversion of substrate compound to product compound can further comprise one or more steps selected from: extraction, isolation, purification, crystallization, filtration, and/or lyophilization of product compound(s). Methods, techniques, and protocols for extracting, isolating, purifying, and/or crystallizing the product(s) from biocatalytic reaction mixtures produced by the processes provided herein are known to the ordinary artisan and/or accessed through routine experimentation. Additionally, illustrative methods are provided in the Examples below.

Engineered PanK Polynucleotides Encoding Engineered Polypeptides, Expression Vectors and Host Cells The present invention provides polynucleotides encoding the engineered enzyme polypeptides described herein. In some embodiments, the polynucleotides are operatively linked to one or more heterologous regulatory sequences that control gene expression to create a recombinant polynucleotide capable of expressing the polypeptide. In some embodiments, expression constructs containing at least one heterologous polynucleotide encoding the engineered enzyme polypeptide(s) is introduced into appropriate host cells to express the corresponding enzyme polypeptide(s).

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode an engineered enzyme (e.g., PanK) polypeptide. Thus, the present invention provides methods and compositions for the production of each and every possible variation of enzyme polynucleotides that could be made that encode the enzyme polypeptides described herein by selecting combinations based on the possible codon choices, and all such variations are to be considered specifically disclosed for any polypeptide described herein, including the amino acid sequences presented in the Examples (e.g., in the various Tables).

In some embodiments, the codons are preferably optimized for utilization by the chosen host cell for protein production. For example, preferred codons used in bacteria are typically used for expression in bacteria. Consequently, codon optimized polynucleotides encoding the engineered enzyme polypeptides contain preferred codons at about 40%, 50%, 60%, 70%, 80%, 90%, or greater than 90% of the codon positions in the full length coding region.

In some embodiments, the enzyme polynucleotide encodes an engineered polypeptide having enzyme activity with the properties disclosed herein, wherein the polypeptide comprises an amino acid sequence having at least 60%, 65%, 70%, 75%, 80%, 85%, 86%, 87%, 88%, 89%, 90%, 91%, 92%, 93%, 94%, 95%, 96%, 97%, 98%, 99% or more identity to a reference sequence selected from the SEQ ID NOS provided herein, or the amino acid sequence of any variant (e.g., those provided in the Examples), and one or more residue differences as compared to the reference polynucleotide(s), or the amino acid sequence of any variant as disclosed in the Examples (for example 1, 2, 3, 4, 5, 6, 7, 8, 9, 10 or more amino acid residue positions). In some embodiments, the reference polypeptide sequence comprises SEQ ID NO: 2, while in some other embodiments, the reference polypeptide sequence comprises SEQ ID NO: 30, SEQ ID NO: 60, SEQ ID NO: 132, SEQ ID NO: 222, SEQ ID NO: 230, SEQ ID NO: 240, and/or SEQ ID NO: 276.

In some embodiments, the polynucleotides are capable of hybridizing under highly stringent conditions to a reference polynucleotide sequence selected from any polynucleotide sequence provided herein, or a complement thereof, or a polynucleotide sequence encoding any of the variant enzyme polypeptides provided herein. In some embodiments, the polynucleotide capable of hybridizing under highly stringent conditions encodes an enzyme polypeptide comprising an amino acid sequence that has one or more residue differences as compared to a reference sequence.

In some embodiments, an isolated polynucleotide encoding any of the engineered enzyme polypeptides herein is manipulated in a variety of ways to facilitate expression of the enzyme polypeptide. In some embodiments, the polynucleotides encoding the enzyme polypeptides comprise expression vectors where one or more control sequences is present to regulate the expression of the enzyme polynucleotides and/or polypeptides. Manipulation of the isolated polynucleotide prior to its insertion into a vector may be desirable or necessary depending on the expression vector utilized. Techniques for modifying polynucleotides and nucleic acid sequences utilizing recombinant DNA methods are well known in the art. In some embodiments, the control sequences include among others, promoters, leader sequences, polyadenylation sequences, propeptide sequences, signal peptide sequences, and transcription terminators. In some embodiments, suitable promoters are selected based on the host cells selection. For bacterial host cells, suitable promoters for directing transcription of the nucleic acid constructs of the present disclosure, include, but are not limited to promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus* stearothennophilus maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is also a suitable transcription terminator sequence (i.e., a sequence recognized by a host cell to terminate transcription). In some embodiments, the terminator sequence is operably linked to the 3' terminus of the nucleic acid sequence encoding the enzyme polypeptide. Any suitable terminator which is functional in the host cell of choice finds use in the present invention. Exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is also a suitable leader sequence (i.e., a non-translated region of an mRNA that is important for translation by the host cell). In some embodiments, the leader sequence is operably linked to the 5' terminus of the nucleic acid sequence encoding the enzyme polypeptide. Any suitable leader sequence that is functional in the host cell of choice find use in the present invention. Exemplary leaders for filamentous fungal host cells are obtained from the genes for *Aspergillus oryzae* TAKA amylase, and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

In some embodiments, the control sequence is also a polyadenylation sequence (i.e., a sequence operably linked to the 3' terminus of the nucleic acid sequence and which, when transcribed, is recognized by the host cell as a signal to add polyadenosine residues to transcribed mRNA). Any suitable polyadenylation sequence which is functional in the host cell of choice finds use in the present invention. Exemplary polyadenylation sequences for filamentous fungal host cells include, but are not limited to the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are known (See e.g., Guo and Sherman, Mol. Cell. Biol., 15:5983-5990 [1995]).

In some embodiments, the control sequence is also a signal peptide (i.e., a coding region that codes for an amino acid sequence linked to the amino terminus of a polypeptide and directs the encoded polypeptide into the cell's secretory pathway). In some embodiments, the 5' end of the coding sequence of the nucleic acid sequence inherently contains a signal peptide coding region naturally linked in translation reading frame with the segment of the coding region that encodes the secreted polypeptide. Alternatively, in some embodiments, the 5' end of the coding sequence contains a signal peptide coding region that is foreign to the coding sequence. Any suitable signal peptide coding region which directs the expressed polypeptide into the secretory pathway of a host cell of choice finds use for expression of the engineered polypeptide(s). Effective signal peptide coding regions for bacterial host cells are the signal peptide coding regions include, but are not limited to those obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus* stearothermophilus neutral proteases (nprT, nprS, nprM), and *Bacillus subtilis* prsA. Further signal peptides are known in the art (See e.g., Simonen and Palva, Microbiol. Rev., 57:109-137 [1993]). In some embodiments, effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is also a propeptide coding region that codes for an amino acid sequence positioned at the amino terminus of a polypeptide. The resultant polypeptide is referred to as a "proenzyme," "propolypeptide," or "zymogen." A propolypeptide can be converted to a mature active polypeptide by catalytic or autocatalytic cleavage of the propeptide from the propolypeptide. The propeptide coding region may be obtained from any suitable source, including, but not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those that cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention is directed to a recombinant expression vector comprising a polynucleotide encoding an engineered enzyme polypeptide, and one or more expression regulating regions such as a promoter and a terminator, a replication origin, etc., depending on the type of hosts into which they are to be introduced. In some embodiments, the various nucleic acid and control sequences described herein are joined together to produce recombinant expression vectors which include one or more convenient restriction sites to allow for insertion or substitution of the nucleic acid sequence encoding the enzyme polypeptide at such sites. Alternatively, in some embodiments, the nucleic acid sequence of the present invention is expressed by inserting the nucleic acid sequence or a nucleic acid construct comprising the sequence into an appropriate vector for expression. In some embodiments involving the creation of the expression vector, the coding sequence is located in the vector so that the coding sequence is operably linked with the appropriate control sequences for expression.

The recombinant expression vector may be any suitable vector (e.g., a plasmid or virus), that can be conveniently subjected to recombinant DNA procedures and bring about the expression of the enzyme polynucleotide sequence. The choice of the vector typically depends on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector is one in which, when introduced into the host cell, it is integrated into the genome and replicated together with the chromosome(s) into which it has been integrated. Furthermore, in some embodiments, a single vector or plasmid, or two or more vectors or plasmids which together contain the total DNA to be introduced into the genome of the host cell, and/or a transposon is utilized.

In some embodiments, the expression vector contains one or more selectable markers, which permit easy selection of transformed cells. A "selectable marker" is a gene, the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in filamentous fungal host cells include, but are not limited to, amdS (acetamidase; e.g., from *A. nidulans* or *A. orzyae*), argB (ornithine carbamoyltransferases), bar (phosphinothricin acetyltransferase; e.g., from *S. hygroscopicus*), hph (hygromycin phosphotransferase), niaD (nitrate reductase), pyrG (orotidine-5'-phosphate decarboxylase; e.g., from *A. nidulans* or *A. orzyae*), sC (sulfate adenyltransferase), and trpC (anthranilate synthase), as well as equivalents thereof.

In another aspect, the present invention provides a host cell comprising at least one polynucleotide encoding at least one engineered enzyme polypeptide of the present invention, the polynucleotide(s) being operatively linked to one or more control sequences for expression of the engineered enzyme enzyme(s) in the host cell. Host cells suitable for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Exemplary host cells also include various *Escherichia coli* strains (e.g., W3110 (ΔfhuΔ) and BL21). Examples of bacterial selectable markers include, but are not limited to the dal genes from *Bacillus subtilis* or *Bacillus licheniformis*, or markers, which confer antibiotic resistance such as ampicillin, kanamycin, chloramphenicol, and or tetracycline resistance.

In some embodiments, the expression vectors of the present invention contain an element(s) that permits integration of the vector into the host cell's genome or autonomous replication of the vector in the cell independent of the genome. In some embodiments involving integration into the host cell genome, the vectors rely on the nucleic acid sequence encoding the polypeptide or any other element of the vector for integration of the vector into the genome by homologous or nonhomologous recombination.

In some alternative embodiments, the expression vectors contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements preferably contain a sufficient number of nucleotides, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori or the origins of replication of plasmids pBR322, pUC19, pACYC177 (which plasmid has the P15A ori), or pACYC184 permitting replication in *E. coli*, and pUB110, pE194, or pTA1060 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (See e.g., Ehrlich, Proc. Natl. Acad. Sci. USA 75:1433 [1978]).

In some embodiments, more than one copy of a nucleic acid sequence of the present invention is inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include, but are not limited to the p3xFLAG™ expression vectors (Sigma-Aldrich Chemicals), which include a CMV promoter and hGH polyadenylation site for expression in mammalian host cells and a pBR322 origin of replication and ampicillin resistance markers for amplification in *E. coli*. Other suitable expression vectors include, but are not limited to pBluescriptII SK(−) and pBK-CMV (Stratagene), and plasmids derived from pBR322 (Gibco BRL), pUC (Gibco BRL), pREP4, pCEP4 (Invitrogen) or pPoly (See e.g., Lathe et al., Gene 57:193-201 [1987]).

Thus, in some embodiments, a vector comprising a sequence encoding at least one variant pantothenate kinase is transformed into a host cell in order to allow propagation of the vector and expression of the variant pantothenate kinase(s). In some embodiments, the variant pantothenate kinases are post-translationally modified to remove the signal peptide and in some cases may be cleaved after secretion. In some embodiments, the transformed host cell described above is cultured in a suitable nutrient medium under conditions permitting the expression of the variant pantothenate kinase(s). Any suitable medium useful for culturing the host cells finds use in the present invention, including, but not limited to minimal or complex media containing appropriate supplements. In some embodiments, host cells are grown in HTP media. Suitable media are available from various commercial suppliers or may be prepared according to published recipes (e.g., in catalogues of the American Type Culture Collection).

In another aspect, the present invention provides host cells comprising a polynucleotide encoding an improved pantothenate kinase polypeptide provided herein, the polynucleotide being operatively linked to one or more control sequences for expression of the pantothenate kinase enzyme in the host cell. Host cells for use in expressing the pantothenate kinase polypeptides encoded by the expression vectors of the present invention are well known in the art and include but are not limited to, bacterial cells, such as *E. coli, Bacillus megaterium, Lactobacillus kefir, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture media and growth conditions for the above-described host cells are well known in the art.

Polynucleotides for expression of the pantothenate kinase may be introduced into cells by various methods known in the art. Techniques include among others, electroporation, biolistic particle bombardment, liposome mediated transfection, calcium chloride transfection, and protoplast fusion. Various methods for introducing polynucleotides into cells are known to those skilled in the art.

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. In some embodiments, the fungal host cells are yeast cells and filamentous fungal cells. The filamentous fungal host cells of the present invention include all filamentous forms of the subdivision Eumycotina and Oomycota. Filamentous fungi are characterized by a vegetative mycelium with a cell wall composed of chitin, cellulose and other complex polysaccharides. The filamentous fungal host cells of the present invention are morphologically distinct from yeast.

In some embodiments of the present invention, the filamentous fungal host cells are of any suitable genus and species, including, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium*, and/or *Volvariella*, and/or teleomorphs, or anamorphs, and synonyms, basionyms, or taxonomic equivalents thereof.

In some embodiments of the present invention, the host cell is a yeast cell, including but not limited to cells of *Candida, Hansenula, Saccharomyces, Schizosaccharomyces, Pichia, Kluyveromyces*, or *Yarrowia* species. In some embodiments of the present invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In some embodiments of the invention, the host cell is an algal cell such as *Chlamydomonas* (e.g., *C. reinhardtii*) and *Phormidium* (P. sp. ATCC29409).

In some other embodiments, the host cell is a prokaryotic cell. Suitable prokaryotic cells include, but are not limited to Gram-positive, Gram-negative and Gram-variable bacterial cells. Any suitable bacterial organism finds use in the present invention, including but not limited to *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*. In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, or *Zymomonas*. In some embodiments, the bacterial host strain is non-pathogenic to humans. In some embodiments the bacterial host strain is an industrial strain. Numerous bacterial industrial strains are known and suitable in the present invention. In some embodiments of the present invention, the bacterial host cell is an *Agrobacterium* species (e.g., *A. radiobacter, A. rhizogenes*, and *A. rubi*). In some embodiments of the present invention, the bacterial host cell is an *Arthrobacter* species (e.g., *A. aurescens, A. citreus, A. globiformis, A. hydrocarboglutamicus, A. mysorens, A. nicotianae, A. paraffineus, A. protophonniae, A. roseoparqffinus, A. sulfureus*, and *A. ureafaciens*). In some embodiments of the present invention, the bacterial host cell is a *Bacillus* species (e.g., *B. thuringensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans*, and *B. amyloliquefaciens*). In some embodiments, the host cell is an industrial *Bacillus* strain including but not limited to *B. subtilis, B. pumilus, B. licheniformis, B. megaterium, B. clausii, B. stearothermophilus*, or *B. amyloliquefaciens*. In some embodiments, the *Bacillus* host cells are *B. subtilis, B. licheniformis, B. megaterium, B. stearothermophilus*, and/or *B. amyloliquefaciens*. In some embodiments, the bacterial host cell is a *Clostridium* species (e.g., *C. acetobutylicum, C. tetani* E88, *C. lituseburense, C. saccharobutylicum, C. perfringens*, and *C. beijerinckii*). In some embodiments, the bacterial host cell is a *Corynebacterium* species (e.g., *C. glutamicum* and *C. acetoacidophilum*). In some embodiments the bacterial host cell is an *Escherichia* species (e.g., *E. coli*). In some embodiments, the host cell is *Escherichia coli* W3110. In some embodiments, the bacterial host cell is an *Erwinia* species (e.g., *E. uredovora, E. carotovora, E. ananas, E. herbicola, E. punctata*, and *E. terreus*). In some embodiments, the bacterial host cell is a *Pantoea* species (e.g., *P. citrea*, and *P. agglomerans*). In some embodiments the bacterial host cell is a *Pseudomonas* species (e.g., *P. putida, P. aeruginosa, P. mevalonii*, and P. sp. D-01 10). In some embodiments, the bacterial host cell is a *Streptococcus* species (e.g., *S. equisimiles, S. pyogenes*, and *S. uberis*). In some embodiments, the bacterial host cell is a *Streptomyces* species (e.g., *S. ambofaciens, S. achromogenes, S. avermitilis, S. coelicolor, S. aureofaciens, S. aureus, S. fungicidicus, S. griseus*, and *S. lividans*). In some embodiments, the bacterial host cell is a *Zymomonas* species (e.g., *Z. mobilis*, and *Z. lipolytica*).

Many prokaryotic and eukaryotic strains that find use in the present invention are readily available to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some embodiments, host cells are genetically modified to have characteristics that improve protein secretion, protein stability and/or other properties desirable for expression and/or secretion of a protein. Genetic modification can be achieved by genetic engineering techniques and/or classical microbiological techniques (e.g., chemical or UV mutagenesis and subsequent selection). Indeed, in some embodiments, combinations of recombinant modification and classical selection techniques are used to produce the host cells. Using recombinant technology, nucleic acid molecules can be introduced, deleted, inhibited or modified, in a manner that results in increased yields of pantothenate kinase variant(s) within the host cell and/or in the culture medium. For example, knockout of Alp1 function results in a cell that is protease deficient, and knockout of pyr5 function results in a cell with a pyrimidine deficient phenotype. In one genetic engineering approach, homologous recombination is used to induce targeted gene modifications by specifically targeting a gene in vivo to suppress expression of the encoded protein. In alternative approaches, siRNA, antisense and/or ribozyme technology find use in inhibiting gene expression. A variety of methods are known in the art for reducing expression of protein in cells, including, but not limited to deletion of all or part of the gene encoding the protein and site-specific mutagenesis to disrupt expression or activity of the gene product. (See e.g., Chaveroche et al., Nucl. Acids Res., 28:22 e97 [2000]; Cho et al., Molec. Plant Microbe Interact., 19:7-15 [2006]; Maruyama and Kitamoto, Biotechnol Lett., 30:1811-1817 [2008]; Takahashi et al., Mol. Gen. Genom., 272: 344-352 [2004]; and You et al., Arch. Microbiol., 191:615-622 [2009], all of which are incorporated by reference herein). Random mutagenesis, followed by screening for desired mutations also finds use (See e.g., Combier et al., *FEMS Microbiol. Lett.,* 220:141-8 [2003]; and Firon et al., *Eukary. Cell* 2:247-55 [2003], both of which are incorporated by reference).

Introduction of a vector or DNA construct into a host cell can be accomplished using any suitable method known in the art, including but not limited to calcium phosphate transfection, DEAE-dextran mediated transfection, PEG-mediated transformation, electroporation, or other common techniques known in the art. In some embodiments, the *Escherichia coli* expression vector pCK100900i (See, U.S. Pat. No. 9,714,437, which is hereby incorporated by reference herein) finds use.

In some embodiments, the engineered host cells (i.e., "recombinant host cells") of the present invention are cultured in conventional nutrient media modified as appropriate for activating promoters, selecting transformants, or amplifying the pantothenate kinase polynucleotide. Culture conditions, such as temperature, pH and the like, are those previously used with the host cell selected for expression, and are well-known to those skilled in the art. As noted, many standard references and texts are available for the culture and production of many cells, including cells of bacterial, plant, animal (especially mammalian) and archebacterial origin.

In some embodiments, cells expressing the variant pantothenate kinase polypeptides of the invention are grown under batch or continuous fermentations conditions. Classical "batch fermentation" is a closed system, wherein the compositions of the medium is set at the beginning of the fermentation and is not subject to artificial alternations during the fermentation. A variation of the batch system is a "fed-batch fermentation" which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. "Continuous fermentation" is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments of the present invention, cell-free transcription/translation systems find use in producing variant pantothenate kinase(s). Several systems are commercially available and the methods are well-known to those skilled in the art.

The present invention provides methods of making variant pantothenate kinase polypeptides or biologically active fragments thereof. In some embodiments, the method comprises: providing a host cell transformed with a polynucleotide encoding an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO: 2, SEQ ID NO: 30, SEQ ID NO: 60, SEQ ID NO: 132, SEQ ID NO: 222, SEQ ID NO: 230, SEQ ID NO: 240, and/or SEQ ID NO: 276, and comprising at least one mutation as provided herein; culturing the transformed host cell in a culture medium under conditions in which the host cell expresses the encoded variant pantothenate kinase polypeptide; and optionally recovering or isolating the expressed variant pantothenate kinase polypeptide, and/or recovering or isolating the culture medium containing the expressed variant pantothenate kinase polypeptide. In some embodiments, the methods further provide optionally lysing the transformed host cells after expressing the encoded pantothenate kinase polypeptide and optionally recovering and/or isolating the expressed variant pantothenate kinase polypeptide from the cell lysate. The present invention further provides methods of making a variant pantothenate kinase polypeptide comprising cultivating a host cell transformed with a variant pantothenate kinase polypeptide under conditions suitable for the production of the variant pantothenate kinase polypeptide and recovering the variant pantothenate kinase polypeptide. Typically, recovery or isolation of the pantothenate kinase polypeptide is from the host cell culture medium, the host cell or both, using protein recovery techniques that are well known in the art, including those described herein. In some embodiments, host cells are harvested by centrifugation, disrupted by physical or chemical means, and the resulting crude extract retained for further purification. Microbial cells employed in expression of proteins can be disrupted by any convenient method, including, but not limited to freeze-thaw cycling, sonication, mechanical disruption, and/or use of cell lysing agents, as well as many other suitable methods well known to those skilled in the art.

Engineered pantothenate kinase enzymes expressed in a host cell can be recovered from the cells and/or the culture medium using any one or more of the techniques known in the art for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ (Sigma-Aldrich). Thus, in some embodiments, the resulting polypeptide is recovered/isolated and optionally purified by any of a number of methods known in the art. For example, in some embodiments, the polypeptide is isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. In some embodiments, protein refolding steps are used, as desired, in completing the configuration of the mature protein. In addition, in some embodiments, high performance liquid chromatography (HPLC) is employed in the final purification steps. For example, in some embodiments, methods known in the art, find use in the present invention (See e.g., Parry et al., Biochem. J., 353:117 [2001]; and Hong et al., Appl. Microbiol. Biotechnol., 73:1331 [2007], both of which are incorporated herein by reference). Indeed, any suitable purification methods known in the art find use in the present invention.

Chromatographic techniques for isolation of the pantothenate kinase polypeptide include, but are not limited to reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., are known to those skilled in the art.

In some embodiments, affinity techniques find use in isolating the improved pantothenate kinase enzymes. For affinity chromatography purification, any antibody which specifically binds the pantothenate kinase polypeptide may be used. For the production of antibodies, various host animals, including but not limited to rabbits, mice, rats, etc., may be immunized by injection with the pantothenate kinase. The pantothenate kinase polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*Bacillus* Calmette Guerin) and *Corynebacterium parvum.*

In some embodiments, the pantothenate kinase variants are prepared and used in the form of cells expressing the enzymes, as crude extracts, or as isolated or purified preparations. In some embodiments, the pantothenate kinase variants are prepared as lyophilisates, in powder form (e.g., acetone powders), or prepared as enzyme solutions. In some embodiments, the pantothenate kinase variants are in the form of substantially pure preparations.

In some embodiments, the pantothenate kinase polypeptides are attached to any suitable solid substrate. Solid substrates include but are not limited to a solid phase, surface, and/or membrane. Solid supports include, but are not limited to organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

In some embodiments, immunological methods are used to purify pantothenate kinase variants. In one approach, antibody raised against a variant pantothenate kinase polypeptide (e.g., against a polypeptide comprising SEQ ID NO: 2, SEQ ID NO: 30, SEQ ID NO: 60, SEQ ID NO: 132, SEQ ID NO: 222, SEQ ID NO: 230, SEQ ID NO: 240, and/or SEQ ID NO: 276, and/or an immunogenic fragment thereof) using conventional methods is immobilized on beads, mixed with cell culture media under conditions in which the variant pantothenate kinase is bound, and precipitated. In a related approach, immunochromatography finds use.

In some embodiments, the variant pantothenate kinases are expressed as a fusion protein including a non-enzyme portion. In some embodiments, the variant pantothenate kinase sequence is fused to a purification facilitating domain. As used herein, the term "purification facilitating domain" refers to a domain that mediates purification of the polypeptide to which it is fused. Suitable purification domains include, but are not limited to metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; See e.g., Wilson et al., Cell 37:767 [1984]), maltose binding protein sequences, the FLAG epitope utilized in the FLAGS extension/affinity purification system (e.g., the system available from Immunex Corp), and the like. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography; See e.g., Porath et al., Prot. Exp. Purif., 3:263-281 [1992]) while the enterokinase cleavage site provides a means for separating the variant pantothenate kinase polypeptide from the fusion protein. pGEX vectors (Promega) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Accordingly, in another aspect, the present invention provides methods of producing the engineered enzyme polypeptides, where the methods comprise culturing a host cell capable of expressing a polynucleotide encoding the engineered enzyme polypeptide under conditions suitable for expression of the polypeptide. In some embodiments, the methods further comprise the steps of isolating and/or purifying the enzyme polypeptides, as described herein.

Appropriate culture media and growth conditions for host cells are well known in the art. It is contemplated that any suitable method for introducing polynucleotides for expression of the enzyme polypeptides into cells will find use in the present invention. Suitable techniques include, but are not limited to electroporation, biolistic particle bombardment, liposome mediated transfection, calcium chloride transfection, and protoplast fusion.

Various features and embodiments of the present invention are illustrated in the following representative examples, which are intended to be illustrative, and not limiting.

EXPERIMENTAL

The following Examples, including experiments and results achieved, are provided for illustrative purposes only and are not to be construed as limiting the present invention. Indeed, there are various suitable sources for many of the reagents and equipment described below. It is not intended that the present invention be limited to any particular source for any reagent or equipment item.

In the experimental disclosure below, the following abbreviations apply: M (molar); mM (millimolar), uM and μM (micromolar); nM (nanomolar); mol (moles); gm and g (gram); mg (milligrams); ug and μg (micrograms); L and 1 (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); psi and PSI (pounds per square inch); ° C. (degrees Centigrade); RT and rt (room temperature); RH (relative humidity); CV (coefficient of variability); CAM and cam (chloramphenicol); PMBS (polymyxin B sulfate); IPTG (isopropyl β-D-1-thiogalactopyranoside); LB (Luria broth); TB (terrific broth); SFP (shake flask powder); CDS (coding sequence); DNA (deoxyribonucleic acid); RNA (ribonucleic acid); nt (nucleotide; polynucleotide); aa (amino acid; polypeptide); *E. coli* W3110 (commonly used laboratory *E. coli* strain, available from the *Coli* Genetic Stock Center [CGSC], New Haven, Conn.); HTP (high throughput); HPLC (high pressure liquid chromatography); HPLC-UV (HPLC-Ultraviolet Visible Detector); 1H NMR (proton nuclear magnetic resonance spectroscopy); FIOPC (fold improvements over positive control); Sigma and Sigma-Aldrich (Sigma-Aldrich, St. Louis, Mo.; Difco (Difco Laboratories, BD Diagnostic Systems, Detroit, Mich.); Microfluidics (Microfluidics, Westwood, Mass.); Life Technologies (Life Technologies, a part of Fisher Scientific, Waltham, Mass.); Amresco (Amresco, LLC, Solon, Ohio); Carbosynth (Carbosynth, Ltd., Berkshire, UK); Varian (Varian Medical Systems, Palo Alto, Calif.); Agilent (Agilent Technologies, Inc., Santa Clara, Calif.); Infors (Infors USA Inc., Annapolis Junction, Md.); and Thermotron (Thermotron, Inc., Holland, Mich.).

Example 1

Variant Production

The parent gene for the evolved pantothenate kinase (EV-PanK) used to produce variants for the present invention was the *E. coli* pantothenate kinase. This gene was synthesized and cloned into pET-30a(+) vector. The gene sequence was optimized for expression in the BL21(DE3) strain of *E. coli*.

BL21(DE3) *E. coli* cells were transformed with the respective plasmid containing the PanK-encoding genes and plated on Luria broth (LB) agar plates containing 1% glucose and 50 μg/mL kanamycin (KAN), and grown overnight at 37° C. Single colonies were picked and inoculated into 180 μL LB containing 1% glucose and 50 μg/mL KAN 96-well shallow microtiter plates. The plates were sealed with air permeable seals and cultures were grown overnight at 30° C., 200 rpm and 85% relative humidity (RH). Then, 10 μL of each of the cell cultures were transferred into the wells of 96-well deepwell plates containing 390 μL TB, 50 μg/mL KAN. The deep-well plates were sealed with air permeable seals and incubated at 30° C., 250 rpm and 85% RH until $OD_{600}$ 0.6-0.8 was reached. The cell cultures were then induced by isopropyl thioglycoside (IPTG) to a final concentration of 1 mM and incubated overnight at 30° C., 250 rpm. The cells were then pelleted using centrifugation at 4000 rpm for 10 min. The supernatants were discarded and the pellets frozen at −80° C. prior to lysis.

Frozen pellets were lysed with 300 μL of lysis buffer containing 50 mM triethanol amine buffer, pH 7.5, 1 mg/mL lysozyme, 0.5 mg/mL PMBS, and 0.05% v/v DNase. The lysis mixture was shaken at room temperature (RT) for 2.5 hours. The plate was then centrifuged for 10 min at 4000 rpm and 4° C. The supernatants were then used in biocatalytic reactions as clarified lysate to determine the activity levels.

Example 2

Activity Assays

Libraries were produced using well-established techniques (e.g., recombination of previously identified beneficial mutations). The polypeptides encoded by each gene were produced in HTP, the clarified lysate was generated as described in Example 1.

Each 50 μL reaction was carried out in shallow 96-well plates with 10 μL of the clarified lysate solution, 5-40 g/L Compound 3 (EGA), 50 mM sodium phosphate buffer, at pH 7.5. The plates were heat sealed and incubated at 30° C. and agitated at 600 RPM in a 50 mm throw Infors shaker overnight maintained at 85% RH for 20 hours.

To produce a chromophore containing species and enable simple reaction monitoring, the reactions samples were derivatized using 2,4-dinitrophenylhydrazine (DNPH). The DNPH derivatization creates a covalent bond between DNPH and aldehydes such as the glyceraldehydes explored for this invention. Post reaction, 20 uL of reaction was combined with 200 uL DNPH (15 mg/mL in DMSO with 2.5% 6N HCl) in new 96 well plates. The derivatization reaction incubated for 1 hour at room temperature. The samples were then filtered by centrifugation using 0.22 micron 96 well filter plates in preparation for testing by UHPLC-MS.

The activity of each sample was measured using an analytical method which monitored the mass spectrum (MS) signal of the desired product, phospho-ethynyl glyceraldehyde (SIM=373). The UHPLC-MS method is an isocratic method run at 1 mL/min on a Zorbax Eclipse HD C18 column. Mobile phase A consisting of H2O with 0.05% formic acid and mobile phase B consisting of Acetonitrile with 0.05% formic acid at a ratio of 60% A and 40% B.

The activity of variant enzymes was calculated by dividing the MS area counts for each variant by the average MS area counts for eight positive parent enzyme samples contained on the same 96 well plate. The amount of product produce by each variant was calculated using a previously determined standard curve.

The following table lists the sequences and activities of a series of evolved enzymes with dramatically improved enzyme activity and tolerance to increased substrate load.

TABLE 2-1

PanK Variant Activity Relative to SEQ ID NO: 2

| SEQ ID NO: (nt/aa) | Amino Acid Differences (Relative to SEQ ID NO: 2) | Conversion Fold Improvement (Relative to SEQ ID NO: 2)[1] |
|---|---|---|
| 33/34 | Y240F/I281M/N282M | + |
| 25/26 | Y240F/L277M | + |
| 39/40 | Y240F | + |
| 43/44 | Y240F | + |
| 3/4 | Y240F/L277M/I281M/N282M | + |
| 9/10 | I54S/Y240W/L277M/I281M | + |

TABLE 2-1-continued

| PanK Variant Activity Relative to SEQ ID NO: 2 | | |
|---|---|---|
| SEQ ID NO: (nt/aa) | Amino Acid Differences (Relative to SEQ ID NO: 2) | Conversion Fold Improvement (Relative to SEQ ID NO: 2)[1] |
| 17/18 | L277I/I281L | + |
| 5/6 | Y240F/L277I | + |
| 35/36 | Y240F/L277I/I281L | + |
| 23/24 | Y240W/I281M | + |
| 37/38 | L277I/I281L | + |
| 7/8 | L277M | + |
| 27/28 | Y240F/L277M | + |
| 21/22 | Y240W/L277I/I281M | ++ |
| 15/16 | Y240F/I281M | ++ |
| 41/42 | L277M/I281M | ++ |
| 19/20 | Y240F/L277M/I281M | ++ |
| 13/14 | L277M/I281M | ++ |
| 31/32 | Y240W/L277I/I281M | +++ |
| 11/12 | Y240F/L277M/I281M | +++ |
| 29/30 | L277I/I281M | +++ |

[1]Levels of increased activity were determined relative to the reference polypeptide of SEQ ID NO: 2, and defined as follows: "+" = 1.40 to 2.50; "++" > 2.50; and "+++" > 7.50.

Example 3

Production of Engineered Polypeptides in pCK110900

The polynucleotide sequence encoding SEQ ID NO: 30 (i.e., SEQ ID NO: 29) was cloned into a pCK110900 vector system (See e.g., U.S. Pat. No. 9,714,437, which is hereby incorporated by reference in its entirety) and subsequently expressed in *E. coli* W3110fhuA under the control of the lac promoter. The pantothenate kinase having the amino acid sequence SEQ ID NO: 30 differs from SEQ ID NO: 2 by having mutations L277I/I281 M.

In a 96-well format, single colonies were picked and grown in 180 μL LB containing 1% glucose and 30 μg/mL CAM, at 30° C., 200 rpm, 85% humidity. Following overnight growth, 204 of the grown cultures were transferred into a deep well plate containing 3804 of TB with 30 μg/mL CAM. The cultures were grown at 30° C., 250 rpm, with 85% humidity. When the optical density (0D600) of the cultures reached 0.6-0.8, expression of the pantothenate kinase gene was induced by addition of IPTG to a final concentration of 1 mM. Following induction, growth was continued for 18-20 hours. Cells were harvested by centrifugation at 4000 rpm at 4° C. for 10 minutes and the media discarded. The cell pellets were stored at −80° C. until ready for use. Prior to performing the assay, cell pellets were resuspended in 250 μL of lysis buffer containing 50 mM potassium phosphate, pH 7.5, with 1 g/L lysozyme and 0.5 g/L PMBS. The plates were agitated with medium-speed shaking for 2 hours on a microtiter plate shaker at room temperature. The plates were then centrifuged at 4000 rpm for 20 minutes at 4° C., and the clarified supernatants were used in the HTP assay reaction described below.

Shake-flask procedures can be used to generate engineered pantothenate kinase polypeptide shake-flask powders (SFP), which are useful for secondary screening assays and/or use in the biocatalytic processes described herein. Shake flask powder (SFP) preparation of enzymes provides a more purified preparation (e.g., up to 30% of total protein) of the engineered enzyme, as compared to the cell lysate used in HTP assays and also allows for the use of more concentrated enzyme solutions. To start the cultures, a single colony of *E. coli* containing a plasmid encoding an engineered polypeptide of interest was inoculated into 50 mL LB with 30 μg/mL CAM and 1% glucose. The culture was grown overnight (at least 16 hours) in an incubator at 30° C., with shaking at 250 rpm. Following overnight growth, the $OD_{600}$ of the culture was measured. The grown culture was diluted into 250 mL of TB with 30 μg/mL CAM, in a 1L shakeflask, to a final $OD_{600}$ of 0.2. The 250 mL culture was grown at 30° C. at 250 rpm, until $OD_{600}$ reached 0.6-0.8. Expression of the panthothenate kinase gene was induced by addition of IPTG to a final concentration of 1 mM, and growth was continued for an additional 18-20 hours. Cells were harvested by transferring the culture into a pre-weighed centrifuge bottle, then centrifuged at 4000 rpm for 20 minutes, at 4° C. The cell pellet was resuspended and washed with 30 mL of cold 50 mM potassium phosphate, pH 7.5 buffer, and re-centrifuged at 4000 rpm for 20 minutes at 4° C. The supernatant was discarded and the remaining cell pellet was weighed. The cells were kept frozen at −80° C. for at least 2 hours prior to lysis. In some embodiments, the cells are stored at −80° C. until ready to use. For lysis, the cell pellet was resuspended in 6 mL of cold 50 mM potassium phosphate, pH 7.5 per 1 g cell pellet. The resuspended cells were lysed using a 110L MICROFLUIDIZER® processor system (Microfluidics). Cell debris was removed by centrifugation at 10,000 rpm for 60 minutes at 4° C. The clarified lysate was collected, frozen at −80° C., and then lyophilized, using standard methods known in the art. Lyophilization of frozen clarified lysate provides a dry shake-flask powder comprising crude engineered polypeptide.

Example 4

Evolution and Screening of Engineered Polypeptides Derived from SEQ ID NO: 30 for Improved Activity The engineered polynucleotide encoding the polypeptide having pantothenate kinase activity of SEQ ID NO: 30 (i.e., SEQ ID NO: 29), was used to generate the further engineered polypeptides of Table 4-1. These polypeptides displayed improved pantothenate kinase activity (e.g., % conversion of ethynyl glyceraldehyde to ethynyl glyceraldehyde phosphate product), as compared to the starting polypeptide.

TABLE 4-1

| PanK Variant Activity Relative to SEQ ID NO: 30 | | |
|---|---|---|
| SEQ ID NO: (nt/aa) | Amino Acid Differences (Relative to SEQ ID NO: 30) | Percent Conversion Fold Improvement (Relative to SEQ ID NO: 30)[1] |
| 45/46 | L13D; Q14E; Q19T; A22G | +++ |
| 49/50 | A22G; F218E | +++ |
| 53/54 | L13D; Q14E; A22G; A37L | +++ |
| 55/56 | W20M | +++ |
| 59/60 | F15L; V27N; W283H | +++ |
| 61/62 | V27N; Q78A; L123W; W283H | +++ |
| 63/64 | W20M; R24A; T30R; V75E | +++ |
| 65/66 | W20M; L70D; V75E | +++ |
| 57/58 | S26P | +++ |
| 67/68 | L13D; Q19T | +++ |
| 73/74 | R24S; T30R; V75E | ++ |
| 75/76 | Q19R; M29S | ++ |
| 79/80 | V27N; W283L | ++ |
| 71/72 | F15L; V27N | ++ |
| 81/82 | F15L; V27N; W283L; A305I | ++ |
| 83/84 | W20M/R24S/D25T/N69T/V75E | ++ |
| 85/86 | F15L/V27N/A305I | ++ |
| 87/88 | F15L/V27N/W283L | ++ |
| 89/90 | W20M/R24A | ++ |

TABLE 4-1-continued

| PanK Variant Activity Relative to SEQ ID NO: 30 | | |
|---|---|---|
| SEQ ID NO: (nt/aa) | Amino Acid Differences (Relative to SEQ ID NO: 30) | Percent Conversion Fold Improvement (Relative to SEQ ID NO: 30)[1] |
| 91/92 | V27N/Q78A | ++ |
| 93/94 | F15L/S26L/W283H | ++ |
| 95/96 | L13D/A22T | + |
| 97/98 | L13D/Q14E/A22T/R106A/F247M | + |
| 99/100 | V75E | + |
| 101/102 | M29S | + |
| 105/106 | R24A | + |
| 107/108 | S26L | + |
| 69/70 | V27N | + |
| 109/110 | L13D/Q14E/F218E/F247M/A305T | + |
| 111/112 | F15L/W283L | + |
| 77/78 | Q19R/A22D/S26P/N69Y | + |
| 103/104 | R24A/T30R | + |
| 51/52 | V27N/W283H | + |
| 113/114 | S26P/M29S | + |
| 115/116 | L13D | + |
| 117/118 | R24S/V75E/R86H/Q134L | + |
| 47/48 | L13D/Q14E/A22G | + |
| 119/120 | A22G/F218E/I271S | + |

[1]Levels of increased activity were determined relative to the reference polypeptide of SEQ ID NO: 30, and defined as follows: "+" = 1.40 to 2.50; "++" >2.50; and "+++" >4.0

The engineered polypeptides were generated from the "backbone" amino acid sequence of SEQ ID NO: 30 using directed evolution methods as described above together with the HTP assay and analytical methods described below.

Directed evolution began with the polynucleotide set forth in SEQ ID NO: 29. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product (compound 6 to compound 5 shown in Scheme 1).

The enzyme assay was carried out in a 96-well format, in 100 μL total volume/well, which included HTP enzyme lysate, 20 g/L (151 mM) ethynyl glyceraldehyde, 2 eq. acetyl phosphate, 5 g/L (9.8 mM) ATP, 20 g/L WT acetate kinase from *Thermotoga maritima,* 10 mM $MgCl_2$, 100 mM potassium phosphate, pH 7.8, final concentrations. The reactions were performed by adding the following into each well: (i) 80 μL of solution containing 25 g/L ethynyl glyceraldehyde, 2 eq. acetyl phosphate, 6.25 g/L ATP, 25 g/L WT acetate kinase from *Thermotoga maritima,* 12.5 mM $MgCl_2$, 125 mM potassium phosphate. The pH of the mixture was adjusted to 7.8, (ii) 20 μL of the HTP clarified lysate (prepared as described above), diluted 4-fold in 50 mM potassium phosphate, pH 7.5 buffer. The reaction plate was heat-sealed and shaken at 600 rpm, at 30° C. for 20-22 hours.

After 20-22 hours, 10 μL of the samples were transferred into separate plates. The samples were mixed with 190 μL of 20 g/L (S)-(−)-1-amino-2-(methoxymethyl)pyrrolidine in water. The plates were sealed and shaken at 400 rpm, at 25° C. for 1 hour. The derivatization reaction was quenched by adding 200 μL $CH_3CN$. The samples were then shaken in a microtiter plate shaker at room temperature, and then centrifuged at 4000 rpm at 4° C. for 10 min. The quenched sample was further diluted 10× in water prior to UPLC analysis. The UPLC run parameters are described below.

TABLE 4-2

| UPLC Parameters | | |
|---|---|---|
| Instrument | Thermo Fisher UltiMate 3000 | |
| Column | Waters HSS T3, 2.1 × 50 mm<br>Gradient (A: 100 mM Triethylammonium acetate in water; B: acetonitrile | |
| | Time (min) | % B |
| Mobile Phase | 0.00 | 1 |
| | 1.30 | 95 |
| | 1.32 | 1 |
| | 1.75 | 1 |
| Flow Rate | 1.0 mL/min | |
| Run time | 1.75 min | |
| Peak Retention Times | SAMP-derivatized product at 1.18 min;<br>SAMP-derivatized substrate at 1.32 nm | |
| Column Temperature | 40° C. | |
| Injection Volume | 10 μL | |
| UV Detection | 247 nm | |

Example 5

Evolution and Screening of Engineered Polypeptides Derived from SEQ ID NO: 60 for Improved Activity The engineered polynucleotide encoding the polypeptide having pantothenate kinase activity of SEQ ID NO: 60 (i.e., SEQ ID NO: 59) was used to generate the further engineered polypeptides of Table 5-1. The pantothenate kinase having the amino acid sequence SEQ ID NO: 60 differs from SEQ ID NO: 2 by having mutations F15L/V27N/L277I/I281M/W283H. These polypeptides displayed improved pantothenate kinase activity (e.g., % conversion of ethynyl glyceraldehyde to ethynyl glyceraldehyde phosphate product), as compared to the starting polypeptide. The engineered polypeptides, having the amino acid sequences of even-numbered sequence identifiers were generated from the "backbone" amino acid sequence of SEQ ID NO:59 using directed evolution methods as described above together with the HTP assay and analytical methods described below.

Directed evolution began with the polynucleotide set forth in SEQ ID NO: 59. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product.

The enzyme assay was carried out in a 96-well format, in 100 μL total volume/well, which included HTP enzyme lysate, 30 g/L (227 mM) ethynyl glyceraldehyde, 2 eq. acetyl phosphate, 5 g/L (9.8 mM) ATP, 20 g/L WT acetate kinase from *Thermotoga maritima,* 10 mM $MgCl_2$, 100 mM potassium phosphate, pH 7.8, final concentrations. The reactions were performed by adding the following into each well: (i) 86 μL of solution containing 34.9 g/L ethynyl glyceraldehyde, 528 mM acetyl phosphate, 5.8 g/L ATP, 23.3 g/L WT acetate kinase from *Thermotoga maritima,* 11.6 mM $MgCl_2$, 116 mM potassium phosphate. The pH of the mixture was adjusted to 7.8, (ii) 14 μL of the HTP clarified lysate (prepared as described previously). The reaction plate was heat-sealed and shaken at 600 rpm, at 30° C. for 20-22 hours.

After 20-22 hours, 200 μL of 50 mM potassium phosphate, pH 7.5 was mixed with the samples. In separate plates, 20 μL of the samples were transferred and mixed with 180 μL of 6 g/L solution of (S)-(−)-1-Amino-2-(methoxymethyl)pyrrolidine in water. The plates were sealed and shaken at 400 rpm, at 25° C. for 1 hour. The derivatization reaction was quenched by adding 200 μL $CH_3CN$. The samples were then shaken in a microtiter plate shaker at room temperature, and then centrifuged at 4000 rpm at 4° C. for 10 min. The quenched sample was further diluted 2× in water prior to UPLC analysis.

TABLE 5-1

PanK Variant Activity Relative to SEQ ID NO: 60

| SEQ ID NO: (nt/aa) | Amino Acid Differences (Relative to SEQ ID NO: 60) | Percent Conversion Fold Improvement (Relative to SEQ ID NO: 60)[1] |
|---|---|---|
| 121/122 | R119P; V157M; S161K | ++ |
| 123/124 | G41C; R119P; S161R; N169Q; N261G; A308V | ++ |
| 125/126 | E44P; L76Q; R119P; V157M; S161K | ++ |
| 127/128 | R119P; N261G; S298R; A308I | ++ |
| 129/130 | G41C; I54W; R119P; V157M; N169Q; N261G | ++ |
| 131/132 | I54V; V157M; S161K; N261G; A308I | ++ |
| 133/134 | Q19A; A22G; I54V; V157M; N169Q | ++ |
| 135/136 | E44P; I54V; R119P; V157M; S161R; N261P; S298R | ++ |
| 137/138 | G41R | ++ |
| 139/140 | G41C; E44Q; N169Q; N261P; S298R; A308V | ++ |
| 141/142 | V157M | ++ |
| 143/144 | G41C; E44Q; I54V; R119P; R120K; V157M; N261G; S298R; A308V | ++ |
| 145/146 | E44Q; I54W; R119P; N169Q | ++ |
| 147/148 | I54W; R119A; V157M; S161K; N169Q | + |
| 149/150 | V157M; A308V | + |
| 151/152 | E44Q; I54V; R119K; R120K; V157M; S161R; N261G | + |
| 153/154 | E44Q; R119P; S161R; N261P; S298R | + |
| 155/156 | G41C; E44Q; I54V; R119A; R120K; V157M; N169Q; N261P | + |
| 157/158 | Q14E; Q19T; G41C; V157M; S161K; N261P | + |
| 159/160 | A22G; R106A; F218E | + |
| 161/162 | E44P; V157M; S298R | + |
| 163/164 | V157M; N169Q; N261P; S298R; A308I | + |
| 165/166 | V157M; S161R; A308V | + |
| 167/168 | R119K; V157M; S161R; N169Q; N261P | + |
| 169/170 | G41C; E44Q; I54V; R119P; R120K; S161K; N169Q; N261G; S298R | + |
| 171/172 | G41C; R119P; S161R; A308V | + |
| 173/174 | E44Q; N261P; A308V | + |
| 175/176 | E44P; I54W; R119A; R120K; N169Q; N261G | + |
| 177/178 | E310S | + |
| 179/180 | G41C; E44Q; N169Q; N261P; A308V | + |
| 181/182 | G41C; E44P; I54W; R119P; S298R; A305T | + |
| 183/184 | R119Q; N169Q; N261G | + |
| 185/186 | E44Q; V157M; S161K; N169Q | + |
| 187/188 | E44P; R119K; V157M; S161K | + |
| 189/190 | E44Q; N261G; S298R; A308V | + |
| 191/192 | E44P; R119P; R120K; N261P | + |
| 193/194 | R120K; V157M; N261P | + |
| 195/196 | T302A | + |
| 197/198 | E44Q; I54V; R119A; R120K; V157M; S161R; N169Q | + |
| 199/200 | V157M; S161R; N169Q; N261G | + |
| 201/202 | Q19T; A22G; G41C; E44P; I54V; R119A; V157M; N261G; S298R; A308I | + |
| 203/204 | G250R | + |
| 205/206 | G41C; E44P; S161R; N169Q; N261G | + |

| | | |
|---|---|---|
| Instrument | Thermo Fisher UltiMate 3000 | |
| Column | Waters HSS T3, 2.1 × 50 mm | |
| | Gradient (A: 100 mM Triethylammonium acetate in water; B: acetonitrile | |
| | Time (min) | % B |
| Mobile Phase | 0.00 | 1 |
| | 1.30 | 95 |
| | 1.32 | 1 |
| | 1.75 | 1 |
| Flow Rate | 1.0 mL/min | |
| Run time | 1.75 min | |
| Peak Retention Times | SAMP-derivatized product at 1.18 min; SAMP-derivatized substrate at 1.32 nm | |
| Column Temperature | 40° C. | |
| Injection Volume | 10 μL | |
| UV Detection | 247 nm | |

[1]Levels of increased activity were determined relative to the reference polypeptide of SEQ ID NO: 60, and defined as follows: "+" = 1.50 to 2.00 and "++" >2.00 to <3.00

Example 6

Evolution and Screening of Engineered Polypeptides Derived from SEQ ID NO: 132 for Improved Activity and Thermostability The engineered polynucleotide encoding the polypeptide having pantothenate kinase activity of SEQ ID NO: 132 (i.e., SEQ ID NO: 131) was used to generate the further engineered polypeptides of Table 6-1. The pantothenate kinase having the amino acid sequence SEQ ID NO: 132 differs from SEQ ID NO: 2 by having mutations F15L/V27N/I54V/V157M/S161 K/N261 G/L277I/I281 M/W283H/A308I. These polypeptides displayed improved pantothenate kinase activity (e.g., % conversion of ethynyl glyceraldehyde to ethynyl glyceraldehyde phosphate product), as compared to the starting polypeptide. The engineered polypeptides, having the amino acid sequences of even-numbered sequence identifiers were generated from the "backbone" amino acid sequence of SEQ ID NO: 132 using directed evolution methods as described above together with the HTP assay and analytical methods described below.

Directed evolution began with the polynucleotide set forth in SEQ ID NO: 131. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product.

Enzymes were lysed as previously described. The clarified lysates were transferred in Bio-RAD hard-shell PCR plates and were incubated at 34° C. for 2 hours. After the lysates were pre-incubated, they were diluted to 40%, by mixing 40 μL of the clarified lysate with 60 μL of 50 mM potassium phosphate, pH 7.5.

The enzyme assay was carried out in a 96-well format, in 100 µL total volume/well, which included HTP enzyme lysate, 30 g/L (227 mM) ethynyl glyceraldehyde, 2 eq. acetyl phosphate, 5 g/L (9.8 mM) ATP, 20 g/L WT acetate kinase from *Thermotoga maritima,* 10 mM $MgCl_2$, 100 mM potassium phosphate, pH 7.8, final concentrations. The reactions were performed by adding the following into each well: (i) 87.5 µL of solution containing 34.3 g/L ethynyl glyceraldehyde, 519 mM acetyl phosphate, 5.7 g/L ATP, 22.9 g/L WT acetate kinase from *Thermotoga maritima,* 11.4 mM $MgCl_2$, 114 mM potassium phosphate. The pH of the mixture was adjusted to 7.8, (ii) 12.5 µL of the diluted, pre-heated lysate (prepared as described above). The reaction plate was heat-sealed and shaken at 600 rpm, at 30° C. for 20-22 hours.

After 20-22 hours, 200 µL of 50 mM potassium phosphate, pH 7.5 was mixed with the samples. In separate plates, 20 µL of the samples were transferred and mixed with 180 µL of 6 g/L solution of (S)-(−)-1-Amino-2-(methoxymethyl)pyrrolidine in water. The plates were sealed and shaken at 400 rpm, at 25° C. for 1 hour. The derivatization reaction was quenched by adding 200 µL CH3CN. The samples were then shaken in a microtiter plate shaker at room temperature, and then centrifuged at 4000 rpm at 4° C. for 10 min. The quenched sample was further diluted 2× in water prior to UPLC analysis.

TABLE 6-1

PanK Variants With Improved Thermostability and Activity Relative to SEQ ID NO: 132

| SEQ ID NO: (nt/aa) | Amino Acid Differences (Relative to SEQ ID NO: 132) | Percent Conversion Fold Improvement (Relative to SEQ ID NO: 132)[1] |
|---|---|---|
| 207/208 | F64L | + |
| 209/210 | Y180E | + |
| 211/212 | L123W | + |
| 213/214 | Q134R | + |
| 215/216 | L123W | + |
| 217/218 | T125S | + |
| 219/220 | T125G | + |
| 221/222 | L123H | + |
| 223/224 | R71Q | + |
| 225/226 | R24A; L48M | + |

[1]Levels of increased activity were determined relative to the reference polypeptide of SEQ ID NO: 132, and defined as follows: "+" = 1.50 to 2.00

In addition to the pre-heated lysates, many of the variants with a wide range of activities, including the variants from Table 6-2, were re-grown and re-evaluated using non-heated lysates. The reactions were carried out as described above, except for the omission of the heating step. Table 6-2 list variants that are improved over SEQ ID NO: 132, under the non-heated conditions.

TABLE 6-2

PanKinase Variant Activity Relative to SEQ ID NO: 132

| SEQ ID NO: (nt/aa) | Amino Acid Differences (Relative to SEQ ID NO: 132) | Percent Conversion Fold Improvement (Relative to SEQ ID NO: 132)[1] |
|---|---|---|
| 209/210 | Y180E; | ++ |
| 217/218 | T125S; | + |
| 219/220 | T125G; | + |
| 227/228 | S92G; L301M; | + |

[1]Levels of increased activity were determined relative to the reference polypeptide of SEQ ID NO: 132, and defined as follows: "+" = 1.50 to 2.00 and "++" >2.00 to <2.5.

Example 7

Evolution and Screening of Engineered Polypeptides Derived from SEQ ID NO: 222 for Improved Activity and Thermostability The engineered polynucleotide encoding the polypeptide having pantothenate kinase activity of SEQ ID NO: 222 (i.e., SEQ ID NO: 221) was used to generate the further engineered polypeptides of Table 7-1. The pantothenate kinase having the amino acid sequence SEQ ID NO: 222 differs from SEQ ID NO: 2 by having mutations F15L/V27N/I54V/L123H/V157M/S161 K/N261 G/L277I/I281 M/W283H/A308I. These polypeptides displayed improved pantothenate kinase activity (e.g., % conversion of ethynyl glyceraldehyde to ethynyl glyceraldehyde phosphate product), as compared to the starting polypeptide. The engineered polypeptides, having the amino acid sequences of even-numbered sequence identifiers were generated from the "backbone" amino acid sequence of SEQ ID NO: 222 using directed evolution methods as described above together with the HTP assay and analytical methods described below.

Directed evolution began with the polynucleotide set forth in SEQ ID NO: 221. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product.

The enzyme assay was carried out in a 96-well format, in 50 µL total volume/well, which included HTP enzyme lysate, 18 g/L (136 mM) ethynyl glyceraldehyde, 2 eq. acetyl phosphate, 5 g/L (9.8 mM) ATP, 20 g/L WT acetate kinase from *Thermotoga maritima,* 10 mM $MgCl_2$, 100 mM potassium phosphate, pH 7.8, final concentrations. The reactions were performed by adding the following into each well: (i) 43.3 µL of solution containing 20.8 g/L ethynyl glyceraldehyde, 315 mM acetyl phosphate, 5.8 g/L ATP, 23.1 g/L WT acetate kinase from *Thermotoga maritima,* 11.5 mM $MgCl_2$, 115 mM potassium phosphate. The pH of the mixture was adjusted to 7.8, (ii) 6.7 µL of 1.5% (v/v) diluted PanK HTP lysate. The reaction plate was heat-sealed and shaken at 600 rpm, at 30° C. for 20-22 hours.

After 20-22 hours, 200 µL of 50 mM potassium phosphate, pH 7.5 was mixed with the samples. In separate plates, 20 µL of the samples were transferred and mixed with 180 µL of 6 g/L solution of (S)-(−)-1-Amino-2-(methoxymethyl)pyrrolidine in water. The plates were sealed and shaken at 400 rpm, at 25° C. for 1 hour. The derivatization reaction was quenched by adding 200 µL CH3CN. The samples were then shaken in a microtiter plate shaker at room temperature, and then centrifuged at 4000 rpm at 4° C. for 10 min. The quenched sample was further diluted 2× in water prior to UPLC analysis.

TABLE 7-1

| PanK Variant Activity Relative to SEQ ID NO: 222 | | |
|---|---|---|
| SEQ ID NO: (nt/aa) | Amino Acid Differences (Relative to SEQ ID NO: 222) | Percent Conversion Fold Improvement (Relative to SEQ ID NO: 222)[1] |
| 229/230 | K143G | + |
| 231/232 | H154P | + |
| 233/234 | N83P; G84H; A305T | + |

[1]Levels of increased activity were determined relative to the reference polypeptide of SEQ ID NO: 222, and defined as follows: "+" = 1.30 to 1.50.

Example 8

Evolution and Screening of Engineered Polypeptides Derived from SEQ ID NO: 230 for Improved Activity The engineered polynucleotide encoding the polypeptide having pantothenate kinase activity of SEQ ID NO: 230 (i.e., SEQ ID NO: 229) was used to generate the further engineered polypeptides of Table 8-1. The pantothenate kinase having the amino acid sequence SEQ ID NO: 230 differs from SEQ ID NO: 2 by having mutations F15L/V27N/I54V/L123H/K143G/V157M/S161K/N261G/L277I/I281M/W283H/A308I. These polypeptides displayed improved pantothenate kinase activity (e.g., % conversion of ethynyl glyceraldehyde to ethynyl glyceraldehyde phosphate product), as compared to the starting polypeptide. The engineered polypeptides, having the amino acid sequences of even-numbered sequence identifiers were generated from the "backbone" amino acid sequence of SEQ ID NO: 230 using directed evolution methods as described above together with the HTP assay and analytical methods described below.

Directed evolution began with the polynucleotide set forth in SEQ ID NO: 229. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product.

The enzyme assay was carried out in a 96-well format, in 50 μL total volume/well, which included HTP enzyme lysate, 3 g/L ethynyl glyceraldehyde, 2 eq. acetyl phosphate, 1 g/L ATP, 10 g/L WT acetate kinase (AcK) from *Thermotoga maritima,* 10 mM $MgCl_2$, 100 mM potassium phosphate, pH 6.8, final concentrations. The reactions were performed by adding the following into each well: (i) 30 μL of solution containing 5 g/L ethynyl glyceraldehyde, 75.7 mM acetyl phosphate, 1.7 g/L ATP, 16.7 g/L WT acetate kinase from *Thermotoga maritima,* 16.7 mM $MgCl_2$, 167 mM potassium phosphate. The pH of the mixture was adjusted to 6.8, (ii) 20 μL of 1.125% (v/v) diluted PanK HTP lysate. The reaction plate was heat-sealed and shaken at 600 rpm, at 30° C. for 3 hours.

After 3 hours, 100 μL of 50 mM potassium phosphate, pH 7.5 was mixed with the samples. In separate plates, 20 μL of the samples were transferred and mixed with 180 μL of 5 g/L solution of (S)-(−)-1-Amino-2-(methoxymethyl)pyrrolidine in water. The plates were sealed and shaken at 400 rpm, at 25° C. for 1 hour. The derivatization reaction was quenched by adding 200 μL $CH_3CN$. The samples were then shaken in a microtiter plate shaker at room temperature, and then centrifuged at 4000 rpm at 4° C. for 10 min. The quenched sample was further diluted 5× in water prior to UPLC analysis.

Hit variants from the high throughput screening were grown in 250-mL shakeflasks and enzyme powders generated. The activity of the enzyme powders was evaluated using 0.025-0.5 g/L enzyme powder, 3 g/L ethynyl glyceraldehyde, 2 equivalents of acetyl phosphate, 1 g/L ATP, 10 g/L AcK WT, 10 mM $MgCl_2$, 100 mM Potassium Phosphate, pH 6.8, 600 rpm, 30° C., 3 hours, using similar assay as described above. Polypeptides with improved activity are listed in Table 8-1.

TABLE 8-1

| PanK Variant Activity Relative to SEQ ID NO: 230 | | |
|---|---|---|
| SEQ ID NO: (nt/aa) | Amino Acid Differences (Relative to SEQ ID NO: 230) | Percent Conversion Fold Improvement (Relative to SEQ ID NO: 230)[1] |
| 235/236 | L13H; N169S; D213E; F247L; H283S; Q288T | + |
| 237/238 | E49D; F247L | ++ |
| 239/240 | V75Q; T104F; L284V | +++ |
| 241/242 | N169S; F247L | + |
| 243/244 | F247L | + |
| 245/246 | F64I; T104F; H154P; L284V | + |
| 247/248 | D16E; F247L | + |

[1]Levels of increased activity were determined relative to the reference polypeptide of SEQ ID NO: 230 and defined as follows: "+" 1.25 to 2.50, "++" >2.50, "+++" >3.50

Example 9

Evolution and Screening of Engineered Polypeptides Derived from SEQ ID NO: 240 for Improved Activity The engineered polynucleotide encoding the polypeptide having pantothenate kinase activity of SEQ ID NO: 240 (i.e., SEQ ID NO: 239) was used to generate the further engineered polypeptides of Table 9-1. The pantothenate kinase having the amino acid sequence SEQ ID NO: 240 differs from SEQ ID NO: 2 by having mutations F15L/V27N/I54V/V75Q/T104F/L123H/K143G/V157M/S161K/N261G/L277I/I281M/W283 H/L284V/A308I. These polypeptides displayed improved pantothenate kinase activity (e.g., % conversion of ethynyl glyceraldehyde to ethynyl glyceraldehyde phosphate product), as compared to the starting polypeptide. The engineered polypeptides, having the amino acid sequences of even-numbered sequence identifiers were generated from the "backbone" amino acid sequence of SEQ ID NO: 240 using directed evolution methods as described above together with the HTP assay and analytical methods described below.

Directed evolution began with the polynucleotide set forth in SEQ ID NO: 239. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product.

The enzyme assay was carried out in a 96-well format, in 50 μL total volume/well, which included HTP enzyme lysate, 3 g/L ethynyl glyceraldehyde, 2 eq. acetyl phosphate, 0.125 g/L ATP, 0.5 g/L of improved acetate kinase (SEQ ID NO: 272), 10 mM $MgCl_2$, 100 mM potassium phosphate, pH 6.8, final concentrations. The reactions were performed by adding the following into each well: (i) 30 μL of solution containing 5 g/L ethynyl glyceraldehyde, 75.7 mM acetyl phosphate, 0.21 g/L ATP, 0.83 g/L of improved acetate kinase (SEQ ID NO: 272), 16.7 mM $MgCl_2$, 167 mM potassium phosphate. The pH of the mixture was adjusted to 6.8, (ii) 20 μL of 2.5% (v/v) diluted PanK HTP lysate. The reaction plate was heat-sealed and shaken at 600 rpm, at 30° C. for 3 hours.

After 3 hours, 100 μL of 50 mM potassium phosphate, pH 7.5 was mixed with the samples. In separate plates, 20 μL of the samples were transferred and mixed with 180 μL of 10 g/L solution of O-benzylhydroxylamine in methanol. The plates were sealed and shaken at 400 rpm, at 25° C. for 20-30 minutes. Samples were further diluted 4× in methanol prior to UPLC analysis, using the method described below in Table 9-2.

Hit variants were grown in 250-mL shakeflasks and enzyme powders generated. The activity of the enzyme powders was evaluated at 0.025-0.5 g/L SF Powder, 3 g/L ethynyl glyceraldehyde, 2 eq. acetyl phosphate, 0.1 g/L ATP, 0.5 g/L of improved acetate kinase (SEQ ID NO: 272), 10 mM $MgCl_2$, 100 mM Potassium Phosphate, pH 6.8, 600 rpm, 30° C., 3h, using similar assay as described above. Polypeptides with improved activity are listed in Table 9-1.

TABLE 9-1

PanK Variant Activity Relative to SEQ ID NO: 240

| SEQ ID NO: (nt/aa) | Amino Acid Differences (Relative to SEQ ID NO: 240) | Percent Conversion Fold Improvement (Relative to SEQ ID NO: 240)[1] |
|---|---|---|
| 249/250 | L8E; F64I; F247L | ++ |
| 251/252 | L8E; F247L; H283S | ++ |
| 253/254 | L8E; L13H; Q14A; N83P; F247L | + |
| 255/256 | L8E; F64I; D213E; F247L | + |
| 257/258 | K264R; T276S | + |
| 259/260 | T10S | ++ |
| 261/262 | L8W | + |

[1]Levels of increased activity were determined relative to the reference polypeptide of SEQ ID NO: 240 and defined as follows: "+" 1.25 to 2.00, "++" >2.00

TABLE 9-2

UPLC Parameters

| | | |
|---|---|---|
| Instrument | Thermo Fisher UltiMate 3000 | |
| Column | Wates Acquity BEH C18 1.7um 2.1 × 50<br>Gradient (A: 100 mM Triethylammonium acetate in water; B: acetonitrile | |
| | Time (min) | % B |
| Mobile Phase | 0.00 | 12.5 |
| | 1.00 | 70 |
| | 1.10 | 100 |
| | 1.30 | 100 |
| | 1.31 | 12.5 |
| | 2.10 | 12.5 |
| Flow Rate | 1.0 mL/min | |
| Run time | 2.1 min | |
| Peak Retention Times | O-benzylhydroxylamine-derivatized product at 1.12 minutes; O-benzylhydroxylamine-derivatized substrate at 1.35 minutes | |
| Column Temperature | 40° C. | |

TABLE 9-2-continued

UPLC Parameters

| | |
|---|---|
| Injection Volume | 5 μL |
| UV Detection | 210 nm |

Example 10

Evolution and Screening of Engineered Polypeptides Derived from SEQ ID NO: 252 for Improved Activity The engineered polynucleotide encoding the polypeptide having pantothenate kinase activity of SEQ ID NO: 252 (i.e., SEQ ID NO: 251) was used to generate the further engineered polypeptides of Table 8-1. These polypeptides displayed improved pantothenate kinase activity (e.g., % conversion of ethynyl glyceraldehyde to ethynyl glyceraldehyde phosphate product), as compared to the starting polypeptide. The engineered polypeptides, having the amino acid sequences of even-numbered sequence identifiers were generated from the "backbone" amino acid sequence of SEQ ID NO: 252 using directed evolution methods as described above together with the HTP assay and analytical methods described below.

Directed evolution began with the polynucleotide set forth in SEQ ID NO: 251. Engineered polypeptides were then selected as starting "backbone" gene sequences. Libraries of engineered polypeptides were generated using various well-known techniques (e.g., saturation mutagenesis, recombination of previously identified beneficial amino acid differences) and screened using HTP assay and analysis methods that measured the polypeptides ability to convert the ethynyl glyceraldehyde substrate to ethynyl glyceraldehyde phosphate product.

The enzyme assay was carried out in a 96-well format, in 50 μL total volume/well, which included HTP enzyme lysate, 3 g/L ethynyl glyceraldehyde, 2 eq. acetyl phosphate, 0.125 g/L ATP, 0.5 g/L of improved acetate kinase (SEQ ID NO: 274), 10 mM $MgCl_2$, 100 mM potassium phosphate, pH 6.8, final concentrations. The reactions were performed by adding the following into each well: (i) 30 μL of solution containing 5 g/L ethynyl glyceraldehyde, 75.7 mM acetyl phosphate, 0.21 g/L ATP, 0.83 g/L of improved acetate kinase (SEQ ID NO: 274) 16.7 mM $MgCl_2$, 167 mM potassium phosphate. The pH of the mixture was adjusted to 6.8, (ii) 20 μL of 5% (v/v) diluted PanK HTP lysate. The reaction plate was heat-sealed and shaken at 600 rpm, at 30° C. for 3 hours.

After 3 hours, 100 μL of 50 mM potassium phosphate, pH 7.5 was mixed with the samples. In separate plates, 20 μL of the samples were transferred and mixed with 180 μL of 10 g/L solution of O-benzylhydroxylamine in methanol. The plates were sealed and shaken at 400 rpm, at 25° C. for 20-30 minutes. Samples were further diluted 4× in methanol prior to UPLC analysis, using the method described in Table 9.2.

Hit variants were grown in 250-mL shakeflasks and enzyme powders generated. The activity of the enzyme powders was evaluated at 0.025-0.5 g/L SF Powder, 3 g/L ethynyl glyceraldehyde, 2 eq. acetyl phosphate, 0.1 g/L ATP, 0.5 g/L of improved acetate kinase (SEQ ID NO: 274), 10 mM $MgCl_2$, 100 mM Potassium Phosphate, pH 6.8, 600 rpm, 30° C., 3h, using similar assay as described above. The engineered polypeptides of this example were expressed and screened with a 10 amino acid histidine tag at the beginning of the amino acid sequence of each engineered polypeptide.

Polypeptides with improved activity are listed in Table 10-1 Amino acid differences are listed relative to SEQ ID NO: 276, which is the engineered polypeptide of SEQ ID NO: 252, without the 10 amino acid histidine tag. Utilization of SEQ ID NO: 276 as the reference sequence for amino acid differences preserves the uniform numbering of amino acids and the position of residue differences/mutations across the engineered polypeptides described in these examples. The pantothenate kinase having the amino acid sequence SEQ ID NO: 276 differs from SEQ ID NO: 2 by having mutations L8E/F15L/V27N/I54V/V75Q/T104F/L123H/K143G/V157M/S161K/F247L/N261G/L277I/I281M/H283S/L284V/A308I.

TABLE 10-1

PanK Variant Activity Relative to SEQ ID NO: 252

| SEQ ID NO: (nt/aa) | Amino Acid Differences (Relative to SEQ ID NO: 276) | Percent Conversion Fold Improvement (Relative to SEQ ID NO: 252)[1] |
|---|---|---|
| 263/264 | L23V; L61I; S304G | + |
| 265/266 | P11Q; L13R; L23V; L61V; Q85V; S304G | + |
| 267/268 | L23V; L61V | + |
| 269/270 | L13R; Q19T; L61I | + |

[1]Levels of increased activity were determined relative to the reference polypeptide of SEQ ID NO: 252 and defined as follows: "+" 1.25 to 2.00

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s)

We claim:

1. An engineered pantothenate kinase polypeptide comprising an amino acid sequence having at least 85% sequence identity to SEQ ID NO: 2, or to a functional fragment thereof, wherein said polypeptide or fragment thereof comprises an amino acid substitution corresponding to amino acid position 277 and/or 281 in SEQ ID NO: 2, wherein said polypeptide has increased ability to convert ethynyl glyceraldehyde to ethynyl glyceraldehyde phosphate when compared the wild-type polypeptide having the amino acid sequence SEQ ID NO: 2.

2. The polypeptide of claim 1, wherein the amino acid substitution is L277M or L277I.

3. The polypeptide of claim 1, wherein the amino acid substitution is at both amino acid positions 277 and 281.

4. The polypeptide of claim 3, wherein the amino acid substitution is L277I/I281L, L277M/1281M, or L277I/I281 M.

5. The polypeptide of claim 4, wherein the mutation is L277I/I281 M.

6. The polypeptide of claim 5, wherein the polypeptide further comprises amino acid substitutions selected from the group consisting of amino acid position 13, 13/14/19/22, 13/14/22, 13/14/22/37, 13/14/22/106/247, 13/14/218/247/305, 13/19, 13/22, 15/26/283, 15/27, 15/27/283, 15/27/283/305, 15/27/305, 15/283, 19/22/26/69, 19/29, 20, 20/24, 20/24/25/69/75, 20/24/30/75, 20/70/75, 22/218, 22/218/271, 24, 24/30, 24/30/75, 24/75/86/134, 26, 26/29, 27, 27/78, 27/78/123/283, 27/283, 29, and 75.

7. The polypeptide of claim 6, wherein the amino acid substitutions is F15L/V27N/L277I/I281M/W283H.

8. The polypeptide of claim 7, wherein the polypeptide further comprises amino acid substitutions selected from the group consisting of amino acid positions 14/19/41/157/161/261, 19/22/41/44/54/119/157/261/298/308, 19/22/54/157/169, 22/106/218, 41, 41/44/54/119/120/157/169/261, 41/44/54/157/120/157/261/298/308, 41/44/54/119/120/161/169/261/298, 41/44/54/119/298/305, 41/44/161/169/261, 41/44/169/261/298/308, 41/44/169/261/308, 41/54/119/157/169/261, 41/119/161/169/261/308, 41/119/161/308, 44/54/119/120/157/161/169, 44/54/119/120/157/161/261, 44/54/119/120/169/261,44/54/119/157/161/261/298, 44/54/119/169, 44/76/119/157/161, 44/119/120/261, 44/119/157/161, 44/119/161/261/298, 44/157/161/169, 44/157/298, 44/261/298/308, 44/261/308, 54/119/157/161/169, 54/157/161/261/308, 119/157/161, 119/157/161/169/261, 119/169/261, 119/261/298,1308, 120/157/261, 157, 157/161/169/261, 157/161/308, 157/169/261/298/308, 157/308, 250, 302, and 310.

9. The polypeptide of claim 8, wherein the amino acid substitutions is F15L/V27N/I54V/V157M/S161K/N261G/L277I/I281 M/W283H/A308I.

10. The polypeptide of claim 9, wherein the polypeptide further comprises amino acid substitutions selected from the group consisting of amino acid positions 24/48, 64, 71, 92/301, 123, 125, 134, and 180.

11. The polypeptide of claim 10, wherein the amino acid substitutions is F15L/V27N/154V/L123H/V157M/S161K/N261 G/L277I/I281 M/W283H/A308I.

12. The polypeptide of claim 11, wherein the polypeptide further comprises amino acid substitutions selected from the group consisting of amino acid positions 83/84/305, 143, and 154.

13. The polypeptide of claim 12, wherein the amino acid substitutions is F15L/V27N/154V/L123H/K143G/V157M/S161K/N261G/L277I/I281M/W283H/A308I.

14. The polypeptide of claim 13, wherein the polypeptide further comprises amino acid substitutions selected from the group consisting of amino acid positions 13/169/213/247/283/288, 16/247, 49/247, 64/104/154/284, 75/104/284, 169/247, and 247.

15. The polypeptide of claim 14, wherein the amino acid substitutions is F15L/V27N/154V/V75Q/T104F/L123H/K143G/V157M/S161K/N261G/L277I/I281M/W283H/L284V/A308I.

16. The polypeptide of claim 15, wherein the polypeptide further comprises amino acid substitutions selected from the group consisting of amino acid positions 8, 8/13/14/83/247, 8/64/213/247, 8/64/247, 8/247/283, 10, and 264/276.

17. The polypeptide of claim 16, wherein the amino acid substitutions is L8E/F15L/V27N/I54V/V75Q/T104F/L123H/K143G/V157M/S161K/F247L/N261G/L277I/I281M/H283S/L284V/A308I.

18. The polypeptide of claim 17, wherein the polypeptide further comprises amino acid substitutions selected from the group consisting of amino acid positions 11/13/23/61/85/304, 13/19/61, 23/61, and 23/61/304.

19. A composition comprising the engineered pantothenate kinase of claim 1.

20. A polynucleotide sequence encoding an engineered pantothenate kinase polypeptide, wherein said polynucleotide sequence comprises at least 85% sequence identity to SEC) ID NO: 1, wherein the polynucleotide sequence encodes the polypeptide of claim 1.

21. A polynucleotide sequence encoding the engineered pantothenate Kinase of claim 1.

22. The polynucleotide sequence of claim 21, wherein said polynucleotide sequence is operably linked to a control sequence.

23. The polynucleotide sequence of claim 21, wherein said polynucleotide sequence is radon optimized.

24. An expression vector comprising at least one polynucleotide sequence of claim 21.

25. A host cell comprising at least one expression vector of claim 24.

26. A host cell comprising at least one polynucleotide sequence of claim 21.

27. A method of producing an engineered pantothenate kinase in a host cell, comprising culturing the host cell of claim 26, under suitable conditions, such that at least one engineered pantothenate kinase is produced.

28. The method of claim 27, further comprising recovering at least one engineered pantothenate kinase from the culture and/or host cell.

29. The method of claim 27, further comprising the step of purifying said at least one engineered pantothenate kinase.

* * * * *

SEQUENCE LISTING

```
<160> NUMBER OF SEQ ID NOS: 276

<210> SEQ ID NO 1
<211> LENGTH: 951
<212> TYPE: DNA
<213> ORGANISM: Artificial Sequence
<220> FEATURE:
<223> OTHER INFORMATION: Pantothenate Kinase from Escherichia coli

<400> SEQUENCE: 1

atgagcatca aagagcagac cctgatgacc ccgtacctgc agttcgaccg taaccaatgg     60

gcggcgctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggctt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtat    720

attaaccgtt tcctgaaatt tcgtgagggt gcgttcaccg acccggatag ctactttcac    780

aactatgcga aactgaccaa ggaagaggcg atcaaaaccg cgatgaccct gtggaaggag    840

atcaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 2
<211> LENGTH: 316
<212> TYPE: PRT
<213> ORGANISM: Artificial Sequence
```

<220> FEATURE:
<223> OTHER INFORMATION: Pantothenate Kinase from Escherichia coli

<400> SEQUENCE: 2

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Leu Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 3
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 3

```
atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120
```

-continued ggtattaacg aggatctgag cctggaggaa gtggcggaaa tctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggttc 720
attaaccgtt tcctgaaatt tcgtgagggt gcgttcaccg acccggatag ctactttcac 780
aactatgcga aactgaccaa ggaagaggcg atcaaaaccg cgatgaccat gtggaaggag 840
atgatgtggc tgaacctgaa gcaaaacatt ctgccgaccc gtgaacgtgc gagcctgatt 900
ctgaccaaaa gcgcgaacca cgcggtggag gaagttcgtc tgcgtaagta a 951

<210> SEQ ID NO 4
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 4

Met Ser Ile Lys Glu Gln Thr Leu Met Thr Pro Tyr Leu Gln Phe Asp
1 5 10 15

Arg Asn Gln Trp Ala Ala Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

-continued

```
Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Met Trp Lys Glu Met Met Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 5
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 5

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggttc     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

attaactggc tgaacctgaa gcaaaacatt ctgccgaccc gtgaacgtgc gagcctgatt     900

ctgaccaaaa gcgcgaacca cgcggtggag gaagttcgtc tgcgtaagta a              951


<210> SEQ ID NO 6
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 6

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
```

-continued

```
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 7
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 7

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360
```

-continued

```
gttgaactga tcaccaccga cggcttcctg cacccgaacc aagtgctgaa ggagcgtggt    420

ctgatgaaga aaaagggctt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat gtggaaggag    840

attaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951
```

<210> SEQ ID NO 8
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 8

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255
```

Ser Tyr Phe His Asn Tyr Ala Lys Leu Thr Lys Glu Glu Ala Ile Lys
260 265 270

Thr Ala Met Thr Met Trp Lys Glu Ile Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 9
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 9
atgagcatca aagagcagac cctgatgacc ccgtacctgc agttcgaccg taaccaatgg 60
gcggcgctgc gtgatagcgt tccgatgacc ctgagcgagg acgaaatcgc gcgtctgaag 120
ggtattaacg aggatctgag cctggaggaa gtggcggaaa gctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg caccccgaacc aagtgctgaa ggagcgtggt 420
ctgatgaaga aaaagggttt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtgg 720
attaaccgtt tcctgaaatt tcgtgagggt gcgttcaccg acccggatag ctactttcac 780
aactatgcga aactgaccaa ggaagaggcg atcaaaaccg cgatgaccat gtggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaagta a 951

<210> SEQ ID NO 10
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 10

Met Ser Ile Lys Glu Gln Thr Leu Met Thr Pro Tyr Leu Gln Phe Asp
1 5 10 15

Arg Asn Gln Trp Ala Ala Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ser Tyr Leu Pro Leu Ser Arg Leu Leu Asn Phe
50 55 60

Tyr Ile Ser Ser Asn Leu Arg Arg Gln Ala Val Leu Glu Gln Phe Leu

-continued

```
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Trp
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Met Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 11
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 11

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggctt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660
```

```
gacttcgtgg attttagcat ctacgttgac gcgccggagg atctgctgca gacctggttc    720

attaaccgtt tcctgaaatt tcgtgagggt gcgttcaccg acccggatag ctactttcac    780

aactatgcga aactgaccaa ggaagaggcg atcaaaaccg cgatgaccat gtggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 12
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 12

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Met Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300
```

Ala Asn His Ala Val Glu Glu Val Arg Leu Arg Lys
305 310 315

<210> SEQ ID NO 13
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 13
atgagcatca aagagcagac cctgatgacc ccgtacctgc agttcgaccg taaccaatgg 60
gcggcgctgc gtgatagcgt tccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggctt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat gtggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaagta a 951

<210> SEQ ID NO 14
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 14

Met Ser Ile Lys Glu Gln Thr Leu Met Thr Pro Tyr Leu Gln Phe Asp
1 5 10 15

Arg Asn Gln Trp Ala Ala Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly

```
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Met Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 15
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 15

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggttc     720

attaaccgtt tcctgaaatt tcgtgagggt gcgttcaccg acccggatag ctactttcac     780

aactatgcga aactgaccaa ggaagaggcg atcaaaaccg cgatgacctt gtggaaggag     840

atgaactggc tgaacctgaa gcaaaacatt ctgccgaccc gtgaacgtgc gagcctgatt     900
```

ctgaccaaaa gcgcgaacca cgcggtggag gaagttcgtc tgcgtaagta a 951

<210> SEQ ID NO 16
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 16

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Leu Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 17
<211> LENGTH: 951
<212> TYPE: DNA
<213> ORGANISM: Artificial Sequence
<220> FEATURE:

<223> OTHER INFORMATION: Pantothenate Kinase from Escherichia coli variant

<400> SEQUENCE: 17

```
atgagcatca aagagcagac cctgatgacc ccgtacctgc agttcgaccg taaccaatgg      60
gcggcgctgc gtgatagcgt tccgatgacc ctgagcgagg acgaaatcgc gcgtctgaag     120
ggtattaacg aggatctgag cctggaggaa gtggcggaaa tctacctgcc gctgagccgt     180
ctgctgaact tctatattag cagcaacctg cgtcgtcagg cggttctgga acaatttctg     240
ggtaccaacg gccagcgtat cccgtatatc attagcattg cgggtagcgt ggcggttggc     300
aaaagcacca ccgcgcgtgt gctgcaggcg ctgctgagcc gttggccgga gcaccgtcgt     360
gttgaactga tcaccaccga cggcttcctg cacccgaacc aagtgctgaa ggagcgtggt     420
ctgatgaaga aaaagggttt cccggaaagc tacgatatgc accgtctggt gaaatttgtt     480
agcgacctga agagcggtgt gccgaacgtt accgcgccgg tgtacagcca cctgatctat     540
gatgttattc cggacggcga taaaaccgtg gttcagccgg acatcctgat tctggagggt     600
ctgaacgtgc tgcaaagcgg catggactat ccgcacgatc cgcaccacgt gtttgttagc     660
gacttcgtgg attttagcat ctacgttgac gcgccggagg atctgctgca gacctggtat     720
attaaccgtt tcctgaaatt tcgtgagggt gcgttcaccg acccggatag ctactttcac     780
aactatgcga aactgaccaa ggaagaggcg atcaaaaccg cgatgaccat ttggaaggag     840
ttgaactggc tgaacctgaa gcaaaacatt ctgccgaccc gtgaacgtgc gagcctgatt     900
ctgaccaaaa gcgcgaacca cgcggtggag gaagttcgtc tgcgtaagta a              951
```

<210> SEQ ID NO 18
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 18

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
```

```
            165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Leu Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 19
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 19

atgagcatca aagagcagac cctgatgacc ccgtacctgc agttcgaccg taaccaatgg     60

gcggcgctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggctt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggttc    720

attaaccgtt tcctgaaatt tcgtgagggt gcgttcaccg acccggatag ctactttcac    780

aactatgcga aactgaccaa ggaagaggcg atcaaaaccg cgatgaccat gtggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 20
<211> LENGTH: 316
<212> TYPE: PRT
<213> ORGANISM: Artificial Sequence
<220> FEATURE:
<223> OTHER INFORMATION: Pantothenate Kinase from Escherichia coli
```

variant

<400> SEQUENCE: 20

Met Ser Ile Lys Glu Gln Thr Leu Met Thr Pro Tyr Leu Gln Phe Asp
1 5 10 15

Arg Asn Gln Trp Ala Ala Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Phe
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Met Trp Lys Glu Met Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 21
<211> LENGTH: 951
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 21
atgagcatca aagagcagac cctgatgacc ccgtacctgc agttcgaccg taaccaatgg 60
gcggcgctgc gtgatagcgt tccgatgacc ctgagcgagg acgaaatcgc gcgtctgaag 120

```
ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtgg    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951
```

```
<210> SEQ ID NO 22
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 22

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
```

```
    210                 215                 220

Phe Ser Ile Tyr Val Asp Ala Pro Glu Asp Leu Leu Gln Thr Trp Trp
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 23
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 23

atgagcatca aagagcagac cctgatgacc ccgtacctgc agttcgaccg taaccaatgg     60

gcggcgctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtgg    720

attaaccgtt tcctgaaatt tcgtgagggt gcgttcaccg acccggatag ctactttcac    780

aactatgcga aactgaccaa ggaagaggcg atcaaaaccg cgatgaccct gtggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 24
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 24

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30
```

```
Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Trp
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Leu Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 25
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 25

```
atgagcatca aagagcagac cctgatgacc ccgtacctgc agttcgaccg taaccaatgg     60

gcggcgctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420
```

-continued

```
ctgatgaaga aaaagggctt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggttc    720

attaaccgtt tcctgaaatt tcgtgagggt gcgttcaccg acccggatag ctactttcac    780

aactatgcga aactgaccaa ggaagaggcg atcaaaaccg cgatgaccat gtggaaggag    840

attaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951
```

```
<210> SEQ ID NO 26
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 26

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
```

```
            260                 265                 270

Thr Ala Met Thr Met Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 27
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 27

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggttc     720

attaaccgtt tcctgaaatt tcgtgagggt gcgttcaccg acccggatag ctactttcac     780

aactatgcga aactgaccaa ggaagaggcg atcaaaaccg cgatgaccat gtggaaggag     840

attaactggc tgaacctgaa gcaaaacatt ctgccgaccc gtgaacgtgc gagcctgatt     900

ctgaccaaaa gcgcgaacca cgcggtggag gaagttcgtc tgcgtaagta a              951


<210> SEQ ID NO 28
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 28

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80
```

```
Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Met Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 29
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 29

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660
```

```
gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 30
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 30

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
```

305 310 315

<210> SEQ ID NO 31
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 31
atgagcatca aagagcagac cctgatgacc ccgtacctgc agttcgaccg taaccaatgg 60
gcggcgctgc gtgatagcgt tccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtgg 720
attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaagta a 951

<210> SEQ ID NO 32
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 32

Met Ser Ile Lys Glu Gln Thr Leu Met Thr Pro Tyr Leu Gln Phe Asp
1 5 10 15

Arg Asn Gln Trp Ala Ala Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

```
Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Trp
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 33
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 33

```
atgagcatca aagagcagac cctgatgacc ccgtacctgc agttcgaccg taaccaatgg     60

gcggcgctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggttc    720

attaaccgtt tcctgaaatt tcgtgagggt gcgttcaccg acccggatag ctactttcac    780

aactatgcga aactgaccaa ggaagaggcg atcaaaaccg cgatgacctt gtggaaggag    840

atgatgtggc tgaacctgaa gcaaaacatt ctgccgaccc gtgaacgtgc gagcctgatt    900

ctgaccaaaa gcgcgaacca cgcggtggag gaagttcgtc tgcgtaagta a             951
```

<210> SEQ ID NO 34
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 34

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Leu Trp Lys Glu Met Met Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 35
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 35

```
atgagcatca aagagcagac cctgatgacc ccgtacctgc agttcgaccg taaccaatgg     60
gcggcgctgc gtgatagcgt tccgatgacc ctgagcgagg acgaaatcgc gcgtctgaag    120
ggtattaacg aggatctgag cctggaggaa gtggcggaaa tctacctgcc gctgagccgt    180
ctgctgaact tctatattag cagcaacctg cgtcgtcagg cggttctgga acaatttctg    240
ggtaccaacg gccagcgtat cccgtatatc attagcattg cgggtagcgt ggcggttggc    300
aaaagcacca ccgcgcgtgt gctgcaggcg ctgctgagcc gttggccgga gcaccgtcgt    360
gttgaactga tcaccaccga cggcttcctg cacccgaacc aagtgctgaa ggagcgtggt    420
ctgatgaaga aaaagggttt cccggaaagc tacgatatgc accgtctggt gaaatttgtt    480
agcgacctga agagcggtgt gccgaacgtt accgcgccgg tgtacagcca cctgatctat    540
gatgttattc cggacggcga taaaaccgtg gttcagccag acatcctgat tctggagggt    600
ctgaacgtgc tgcaaagcgg catggactat ccgcacgatc cgcaccacgt gtttgttagc    660
gacttcgtgg attttagcat ctacgttgac gcgccggagg atctgctgca gacctggttc    720
attaaccgtt tcctgaaatt tcgtgagggt gcgttcaccg acccggatag ctactttcac    780
aactatgcga aactgaccaa ggaagaggcg atcaaaaccg cgatgaccat ttggaaggag    840
ttgaactggc tgaacctgaa gcaaaacatt ctgccgaccc gtgaacgtgc gagcctgatt    900
ctgaccaaaa gcgcgaacca cgcggtggag gaagttcgtc tgcgtaagta a             951
```

<210> SEQ ID NO 36
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 36

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175
```

```
His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Leu Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

```
<210> SEQ ID NO 37
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 37

atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

ttgaactggc tgaacctgaa gcaaaacatt ctgccgaccc gtgaacgtgc gagcctgatt     900

ctgaccaaaa gcgcgaacca cgcggtggag gaagttcgtc tgcgtaagta a              951
```

```
<210> SEQ ID NO 38
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant
```

<400> SEQUENCE: 38

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Leu Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315

<210> SEQ ID NO 39
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 39
atgagcatca aagagcagac cctgatgacc ccgtacctgc agttcgaccg taaccaatgg 60
gcggcgctgc gtgatagcgt tccgatgacc ctgagcgagg acgaaatcgc gcgtctgaag 120
ggtattaacg aggatctgag cctggaggaa gtggcggaaa tctacctgcc gctgagccgt 180

```
ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggttc    720

attaaccgtt tcctgaaatt tcgtgagggt gcgttcaccg acccggatag ctactttcac    780

aactatgcga aactgaccaa ggaagaggcg atcaaaaccg cgatgacctt gtggaaggag    840

attaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951
```

<210> SEQ ID NO 40
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 40

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220
```

```
Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Leu Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 41
<211> LENGTH: 951
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 41

atgagcatca aagagcagac cctgatgacc ccgtacctgc agttcgaccg taaccaatgg     60

gcggcgctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat gtggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 42
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 42

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30
```

```
Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Met Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 43
<211> LENGTH: 951
<212> TYPE: DNA
<213> ORGANISM: Artificial Sequence
<220> FEATURE:
<223> OTHER INFORMATION: Pantothenate Kinase from Escherichia coli variant

<400> SEQUENCE: 43

```
atgagcatca aagagcagac cctgatgacc ccgtacctgc agttcgaccg taaccaatgg      60

gcggcgctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420
```

```
ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggttc    720

attaaccgtt tcctgaaatt tcgtgagggt gcgttcaccg acccggatag ctactttcac    780

aactatgcga aactgaccaa ggaagaggcg atcaaaaccg cgatgaccct gtggaaggag    840

atcaactggc tgaacctgaa gcaaaacatt ctgccgaccc gtgaacgtgc gagcctgatt    900

ctgaccaaaa gcgcgaacca cgcggtggag gaagttcgtc tgcgtaagta a             951


<210> SEQ ID NO 44
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 44

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Phe
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270
```

```
Thr Ala Met Thr Leu Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 45
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 45

atgagcatca aagagcagac cctgatgacc ccgtacgatg aattcgaccg taacacttgg      60

gcgggcctgc gtgatagcgt tccgatgacc ctgagcgagg acgaaatcgc acgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gttcgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948


<210> SEQ ID NO 46
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 46

Met Ser Ile Lys Glu Gln Thr Leu Met Thr Pro Tyr Asp Glu Phe Asp
1               5                   10                  15

Arg Asn Thr Trp Ala Gly Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80
```

-continued

```
Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 47
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 47

atgagcatca aagagcagac cctgatgacc ccgtacgatg aattcgaccg taaccaatgg     60

gcgggcctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720
```

attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 48
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 48

Met Ser Ile Lys Glu Gln Thr Leu Met Thr Pro Tyr Asp Glu Phe Asp
1 5 10 15

Arg Asn Gln Trp Ala Gly Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 49
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 49

```
atgagcatca aagagcagac cctgatgacc ccgtacctgc aattcgaccg taaccaatgg      60

gcgggcctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt ggaggttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ctggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948
```

<210> SEQ ID NO 50
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 50

```
Met Ser Ile Lys Glu Gln Thr Leu Met Thr Pro Tyr Leu Gln Phe Asp
1               5                   10                  15

Arg Asn Gln Trp Ala Gly Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125
```

```
Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Glu Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 51
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 51

atgagcatca aagagcagac cctgatgacc ccgtacctgc agtttgaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 52
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 52

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315

<210> SEQ ID NO 53
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 53

```
atgagcatca aagagcagac cctgatgacc ccgtacgatg aattcgaccg taaccaatgg     60
gcgggcctgc gtgatagcgt tccgatgacc ctgagcgagg acgaaatcct gcgtctgaag    120
ggtattaacg aggatctgag cctggaggaa gtggcggaaa tctacctgcc gctgagccgt    180
ctgctgaact tctatattag cagcaacctg cgtcgtcagg cggttctgga acaatttctg    240
ggtaccaacg gccagcgtat cccgtatatc attagcattg cgggtagcgt ggcggttggc    300
aaaagcacca ccgcgcgtgt gctgcaggcg ctgctgagcc gttggccgga gcaccgtcgt    360
gttgaactga tcaccaccga cggcttcctg cacccgaacc aagtgctgaa ggagcgtggt    420
ctgatgaaga aaaagggttt cccggaaagc tacgatatgc accgtctggt gaaatttgtt    480
agcgacctga agagcggtgt gccgaacgtt accgcgccgg tgtacagcca cctgatctat    540
gatgttattc cggacggcga taaaaccgtg gttcagccgg acatcctgat tctggagggt    600
ctgaacgtgc tgcaaagcgg catggactat ccgcacgatc cgcaccacgt gtttgttagc    660
gacttcgtgg attttagcat ctacgttgac gcgccggagg atctgctgca gacctggtac    720
attaaccgtt tcctgaaatt tcgtgagggt gcgttcaccg acccggatag ctactttcac    780
aactatgcga aactgaccaa ggaagaggcg atcaaaaccg cgatgaccat ttggaaggag    840
atgaactggc tgaacctgaa gcaaaacatt ctgccgaccc gtgaacgtgc gagcctgatt    900
ctgaccaaaa gcgcgaacca cgcggtggag gaagttcgtc tgcgtaag                 948
```

<210> SEQ ID NO 54
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 54

```
Met Ser Ile Lys Glu Gln Thr Leu Met Thr Pro Tyr Asp Glu Phe Asp
1               5                   10                  15

Arg Asn Gln Trp Ala Gly Leu Arg Asp Ser Val Pro Met Thr Leu Ser
            20                  25                  30

Glu Asp Glu Ile Leu Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175
```

-continued

```
His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 55
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 55

```
atgagcatca aagagcagac cctgatgacc ccgtacctgc agttcgaccg taaccaaatg      60

gcggcgctgc gcgatagcgt tccgatgacg ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948
```

<210> SEQ ID NO 56
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 56

Met Ser Ile Lys Glu Gln Thr Leu Met Thr Pro Tyr Leu Gln Phe Asp
1 5 10 15

Arg Asn Gln Met Ala Ala Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 57
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 57
atgagcatca aagagcagac cctgatgacc ccgtacctgc agttcgaccg taaccaatgg 60
gcggctctgc gtgatccggt tccgatgacc ctgagcgagg acgaaatcgc gcgtctgaag 120
ggtattaacg aggatctgag cctggaggaa gtggcggaaa tctacctgcc gctgagccgt 180

-continued

```
ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 58
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 58

```
Met Ser Ile Lys Glu Gln Thr Leu Met Thr Pro Tyr Leu Gln Phe Asp
1               5                   10                  15

Arg Asn Gln Trp Ala Ala Leu Arg Asp Pro Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220
```

-continued

```
Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 59
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 59

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                948
```

<210> SEQ ID NO 60
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 60

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
```

```
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 61
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 61

```
atgagcatca aagagcagac cctgatgacc ccgtacctgc agtttgaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga agcgtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaatgga tcaccaccga cggcttcctg cacccgaacc aagtgctgaa ggagcgtggt     420

ctgatgaaga aaaagggttt cccggaaagc tacgatatgc accgtctggt gaaatttgtt     480
```

-continued

```
agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 62
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 62

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Ala Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Trp Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270
```

-continued

```
Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 63
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 63

atgagcatca aagagcagac cctgatgacc ccgtacctgc agttcgaccg taaccaaatg     60

gcggcgctgg cggatagcgt tccgatgcgc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggaactgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948


<210> SEQ ID NO 64
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 64

Met Ser Ile Lys Glu Gln Thr Leu Met Thr Pro Tyr Leu Gln Phe Asp
1               5                   10                  15

Arg Asn Gln Met Ala Ala Leu Ala Asp Ser Val Pro Met Arg Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Glu Leu Glu Gln Phe Leu
65                  70                  75                  80

Gly Thr Asn Gly Gln Arg Ile Pro Tyr Ile Ile Ser Ile Ala Gly Ser
```

-continued

```
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 65
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 65

atgagcatca aagagcagac cctgatgacc ccgtacctgc agttcgaccg taaccaaatg      60

gcggcgctgc gcgatagcgt tccgatgacg ctgagcgagg acgaaatcgc gcgtctgaag     120

ggtattaacg aggatctgag cctggaggaa gtggcggaaa tctacctgcc gctgagccgt     180

ctgctgaact tctatattag cagcaacgat cgtcgtcagg cggaactgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat cctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720
```

-continued

```
attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948


<210> SEQ ID NO 66
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 66

Met Ser Ile Lys Glu Gln Thr Leu Met Thr Pro Tyr Leu Gln Phe Asp
1               5                   10                  15

Arg Asn Gln Met Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Asp Arg Arg Gln Ala Glu Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 67
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 67
atgagcatca aagagcagac cctgatgacc ccgtacgatc aattcgaccg taacacttgg 60
gcggccctgc gtgatagcgt tccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat ctggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 68
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 68

Met Ser Ile Lys Glu Gln Thr Leu Met Thr Pro Tyr Asp Gln Phe Asp
1               5                   10                  15

Arg Asn Thr Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys

```
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 69
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 69

atgagcatca aagagcagac cctgatgacc ccgtacctgc agtttgaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggcctga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcgcaaacca cgcggtggag gaagttcgtc tgcgtaag                  948
```

<210> SEQ ID NO 70
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 70

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 71
<211> LENGTH: 948
<212> TYPE: DNA
<213> ORGANISM: Artificial Sequence
<220> FEATURE:
<223> OTHER INFORMATION: Pantothenate Kinase from Escherichia coli variant -continued

<400> SEQUENCE: 71

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 72
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 72

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
```

-continued

```
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 73
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 73

atgagcatca aagagcagac cctgatgacc ccgtacctgc agttcgaccg taaccaatgg      60

gcggcgctga gcgatagcgt tccgatgcgc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggaactgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat cctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948


<210> SEQ ID NO 74
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 74
```

```
Met Ser Ile Lys Glu Gln Thr Leu Met Thr Pro Tyr Leu Gln Phe Asp
1               5                   10                  15

Arg Asn Gln Trp Ala Ala Leu Ser Asp Ser Val Pro Met Arg Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Glu Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 75
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 75

```
atgagcatca aagagcagac cctgatgacc ccgtacctgc agttcgaccg taaccgctgg     60

gcggctctgc gtgattcggt tccgtcgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240
```

```
ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccatgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 76
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 76

```
Met Ser Ile Lys Glu Gln Thr Leu Met Thr Pro Tyr Leu Gln Phe Asp
1               5                   10                  15

Arg Asn Arg Trp Ala Ala Leu Arg Asp Ser Val Pro Ser Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
```

-continued

```
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 77
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 77

```
atgagcatca aagagcagac cctgatgacc ccgtacctgc agttcgaccg taaccgctgg     60

gcggatctgc gtgatccggt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagctacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 78
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 78

```
Met Ser Ile Lys Glu Gln Thr Leu Met Thr Pro Tyr Leu Gln Phe Asp
1               5                   10                  15

Arg Asn Arg Trp Ala Asp Leu Arg Asp Pro Val Pro Met Thr Leu Ser
            20                  25                  30

Glu Asp Glu Ile Ala Arg Leu Lys Gly Ile Asn Glu Asp Leu Ser Leu
        35                  40                  45
```

```
Glu Glu Val Ala Glu Ile Tyr Leu Pro Leu Ser Arg Leu Leu Asn Phe
    50                  55                  60

Tyr Ile Ser Ser Tyr Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 79
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 79

atgagcatca aagagcagac cctgatgacc ccgtacctgc agtttgaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480
```

agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaacctgc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 80
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 80

Met Ser Ile Lys Glu Gln Thr Leu Met Thr Pro Tyr Leu Gln Phe Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn Leu Leu Asn Leu Lys Gln 275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 81
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 81
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaacctgc tgaacctgaa gcaaaacatt ctgccgaccc gtgaacgtgc gagcctgatt 900
ctgaccaaaa gcatcaacca cgcggtggag gaagttcgtc tgcgtaag 948

<210> SEQ ID NO 82
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 82

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

```
Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Leu Leu Asn Leu Lys Gln
        275                 280                 285

Asn Ile Leu Pro Thr Arg Glu Arg Ala Ser Leu Ile Leu Thr Lys Ser
    290                 295                 300

Ile Asn His Ala Val Glu Glu Val Arg Leu Arg Lys
305                 310                 315


<210> SEQ ID NO 83
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 83

atgagcatca aagagcagac cctgatgacc ccgtacctgc agttcgaccg taaccaaatg      60

gcggcgctga gcactagcgt tccgatgacg ctgagcgagg acgaaatcgc gcgtctgaag     120

ggtattaacg aggatctgag cctggaggaa gtggcggaaa tctacctgcc gctgagccgt     180

ctgctgaact tctatattag cagcaccctg cgtcgtcagg cggaactgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat cctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780
```

aactatgcga aactgaccaa ggaagaggcg atcaaaaccg cgatgaccat ttggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 84
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 84

Met Ser Ile Lys Glu Gln Thr Leu Met Thr Pro Tyr Leu Gln Phe Asp
1 5 10 15

Arg Asn Gln Met Ala Ala Leu Ser Thr Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Thr Leu Arg Arg Gln Ala Glu Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 85
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 85

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcatcaacca cgcggtggag gaagttcgtc tgcgtaag                  948
```

<210> SEQ ID NO 86
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 86

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140
```

```
Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ile Asn His Ala Val Glu Glu Val Arg Leu Arg Lys
305                 310                 315


<210> SEQ ID NO 87
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 87

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaacctgc tgaacctgaa gcaaaacatt ctgccgaccc gtgaacgtgc gagcctgatt     900

ctgaccaaaa gcgcgaacca cgcggtggag gaagttcgtc tgcgtaag                  948


<210> SEQ ID NO 88
```

<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 88

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Leu Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 89
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 89

-continued

```
atgagcatca aagagcagac cctgatgacc ccgtacctgc agttcgaccg taaccaaatg     60

gcggcgctgg cggatagcgt tccgatgacg ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aggtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat cctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 90
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 90

```
Met Ser Ile Lys Glu Gln Thr Leu Met Thr Pro Tyr Leu Gln Phe Asp
1               5                   10                  15

Arg Asn Gln Met Ala Ala Leu Ala Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190
```

```
Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 91
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 91

```
atgagcatca aagagcagac cctgatgacc ccgtacctgc agtttgaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga agcgtttctg    240

ggtaccaacg gccagcgtat cccgtatatc attagcattg cgggtagcgt ggcggttggc    300

aaaagcacca ccgcgcgtgt gctgcaggcg ctgctgagcc gttggcctga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 92
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 92

```
Met Ser Ile Lys Glu Gln Thr Leu Met Thr Pro Tyr Leu Gln Phe Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Ala Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 93
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 93

```
atgagcatca aagagcagac cctgatgacc ccgtacctgc agctggaccg taaccaatgg     60

gcggcgctgc gtgatctggt gccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240
```

```
ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 94
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 94

```
Met Ser Ile Lys Glu Gln Thr Leu Met Thr Pro Tyr Leu Gln Leu Asp
1               5                   10                  15

Arg Asn Gln Trp Ala Ala Leu Arg Asp Leu Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240
```

```
Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 95
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 95

atgagcatca aagagcagac cctgatgacc ccgtacgatc aattcgaccg taaccaatgg      60

gcgaccctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gttcgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ctggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948


<210> SEQ ID NO 96
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 96

Met Ser Ile Lys Glu Gln Thr Leu Met Thr Pro Tyr Asp Gln Phe Asp
1               5                   10                  15

Arg Asn Gln Trp Ala Thr Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45
```

```
Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 97
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 97

```
atgagcatca aagagcagac cctgatgacc ccgtacgatg aattcgaccg taaccaatgg      60

gcgaccctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcggcagt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540
```

```
gatgttattc cggacggcga taaaaccgtg gttcagccag acatcctgat tctggagggt    600

ctgaacgtgc tgcaaagcgg catggactat ccgcacgatc cgcaccacgt gttcgttagc    660

gacttcgtgg attttagcat ctacgttgac gcgccggagg atctgctgca gacctggtac    720

attaaccgtt tcctgaaaat gcgtgagggt gcgttcaccg acccggatag ctactttcac    780

aactatgcga aactgaccaa ggaagaggcg attaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948


<210> SEQ ID NO 98
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 98

Met Ser Ile Lys Glu Gln Thr Leu Met Thr Pro Tyr Asp Glu Phe Asp
1               5                   10                  15

Arg Asn Gln Trp Ala Thr Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Ala Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Met Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285
```

```
Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 99
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 99

atgagcatca aagagcagac cctgatgacc ccgtacctgc agttcgaccg taaccaatgg      60

gcggcgctgc gtgatagcgt tccgatgacg ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggaactgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aggtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat cctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948


<210> SEQ ID NO 100
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 100

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Glu Leu Glu Gln Phe Leu
65                  70                  75                  80

Gly Thr Asn Gly Gln Arg Ile Pro Tyr Ile Ile Ser Ile Ala Gly Ser
                85                  90                  95
```

-continued

```
Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 101
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 101

```
atgagcatca aagagcagac cctgatgacc ccgtacctgc agttcgaccg taaccagtgg     60

gcggctctgc gtgattcggt tccgtcgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780
```

aactatgcga aactgaccaa ggaagaggcg atcaaaaccg cgatgaccat ttggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 102
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 102

Met Ser Ile Lys Glu Gln Thr Leu Met Thr Pro Tyr Leu Gln Phe Asp
1 5 10 15

Arg Asn Gln Trp Ala Ala Leu Arg Asp Ser Val Pro Ser Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 103

<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 103

```
atgagcatca aagagcagac cctgatgacc ccgtacctgc agttcgaccg taaccaatgg     60

gcggcgctgg cggatagcgt tccgatgcgc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat cctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 104
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 104

```
Met Ser Ile Lys Glu Gln Thr Leu Met Thr Pro Tyr Leu Gln Phe Asp
1               5                   10                  15

Arg Asn Gln Trp Ala Ala Leu Ala Asp Ser Val Pro Met Arg Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140
```

```
Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 105
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 105

```
atgagcatca aagagcagac cctgatgacc ccgtacctgc agttcgaccg taaccaatgg     60

gcggcgctgg cggatagcgt tccgatgacg ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 106
<211> LENGTH: 316

<212> TYPE: PRT
<213> ORGANISM: Artificial Sequence
<220> FEATURE:
<223> OTHER INFORMATION: Pantothenate Kinase from Escherichia coli
variant

<400> SEQUENCE: 106

```
Met Ser Ile Lys Glu Gln Thr Leu Met Thr Pro Tyr Leu Gln Phe Asp
1               5                   10                  15

Arg Asn Gln Trp Ala Ala Leu Ala Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 107
<211> LENGTH: 948
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 107
atgagcatca aagagcagac cctgatgacc ccgtacctgc agttcgaccg taaccaatgg 60
gcggcgctgc gtgatctggt gccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acaatttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agcgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaactggc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 108
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 108

```
Met Ser Ile Lys Glu Gln Thr Leu Met Thr Pro Tyr Leu Gln Phe Asp
1               5                   10                  15

Arg Asn Gln Trp Ala Ala Leu Arg Asp Leu Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190
```

```
Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 109
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 109

atgagcatca aagagcagac cctgatgacc ccgtacgatg aattcgaccg taaccaatgg      60

gcggccctgc gtgatagcgt tccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acaatttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt ggaggttagc     660

gacttcgtgg attttagcat ctacgttgac gcgccggagg atctgctgca gacctggtac     720

attaaccgtt tcctgaaaat gcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcactaacca cgcggtggag gaagttcgtc tgcgtaag                  948


<210> SEQ ID NO 110
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 110

Met Ser Ile Lys Glu Gln Thr Leu Met Thr Pro Tyr Asp Glu Phe Asp
```

-continued

```
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Glu Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Met Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Thr Asn His Ala Val Glu Glu Val Arg Leu Arg Lys
305                 310                 315
```

<210> SEQ ID NO 111
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 111

```
atgagcatca aagagcagac cctgatgacc ccgtacctgc agctggaccg taaccaatgg     60

gcggcgctgc gtgatagcgt tccgatgacc ctgagcgagg acgaaattgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300
```

```
aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaacctgc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 112
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 112

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240
```

```
Ile Asn Arg Phe Leu Lys Phe Arg Glu Gly Ala Phe Thr Asp Pro Asp
            245                 250                 255

Ser Tyr Phe His Asn Tyr Ala Lys Leu Thr Lys Glu Glu Ala Ile Lys
        260                 265                 270

Thr Ala Met Thr Ile Trp Lys Glu Met Asn Leu Leu Asn Leu Lys Gln
    275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 113
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 113

```
atgagcatca aagagcagac cctgatgacc ccgtacctgc agttcgaccg taaccagtgg     60

gcggctctgc gtgatccggt tccgtcgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                948
```

<210> SEQ ID NO 114
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 114

```
Met Ser Ile Lys Glu Gln Thr Leu Met Thr Pro Tyr Leu Gln Phe Asp
1               5                   10                  15

Arg Asn Gln Trp Ala Ala Leu Arg Asp Pro Val Pro Ser Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
```

-continued

```
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 115
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 115

```
atgagcatca aagagcagac cctgatgacc ccgtacgatc aattcgaccg taaccaatgg     60

gcggccctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540
```

```
gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaactggc tgaacctgaa gcaaaacatt ctgccgaccc gtgaacgtgc gagcctgatt    900

ctgaccaaaa gcgcgaacca cgcggtggag gaagttcgtc tgcgtaag                 948
```

<210> SEQ ID NO 116
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 116

```
Met Ser Ile Lys Glu Gln Thr Leu Met Thr Pro Tyr Asp Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285
```

```
Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 117
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 117

atgagcatca aagagcagac cctgatgacc ccgtacctgc agttcgaccg taaccaatgg      60

gcggcgctga gcgatagcgt tccgatgacg ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggaactgga acaatttctg     240

ggtaccaacg gccagcatat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc tggtgctgaa ggagcgtggt     420

ctgatgaaga aaaagggttt cccggaaagc tacgatatgc accgtctggt gaaatttgtt     480

agcgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaactggc tgaacctgaa gcaaaacatt ctgccgaccc gtgaacgtgc gagcctgatt     900

ctgaccaaaa gcgcgaacca cgcggtggag gaagttcgtc tgcgtaag                  948


<210> SEQ ID NO 118
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 118

Met Ser Ile Lys Glu Gln Thr Leu Met Thr Pro Tyr Leu Gln Phe Asp
1               5                   10                  15

Arg Asn Gln Trp Ala Ala Leu Ser Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Glu Leu Glu Gln Phe Leu
65                  70                  75                  80

Gly Thr Asn Gly Gln His Ile Pro Tyr Ile Ile Ser Ile Ala Gly Ser
                85                  90                  95

Val Ala Val Gly Lys Ser Thr Thr Ala Arg Val Leu Gln Ala Leu Leu
```

```
            100                 105                 110

Ser Arg Trp Pro Glu His Arg Arg Val Glu Leu Ile Thr Thr Asp Gly
        115                 120                 125

Phe Leu His Pro Asn Leu Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 119
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 119

```
atgagcatca aagagcagac cctgatgacc ccgtacctgc aattcgaccg taaccaatgg     60

gcgggcctgc gtgatagcgt tccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acaatttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt ggaggttagc    660

gacttcgtgg attttagcat ctacgttgac gccccggagg atctgctgca gacctggtac    720

attaaccgtt tcctgaaatt tcgtgagggt gcgttcaccg acccggatag ctactttcac    780

aactatgcga aactgaccaa ggaagaggcg agtaaaaccg cgatgaccat ttggaaggag    840
```

atgaactggc tgaacctgaa gcaaaacatt ctgccgaccc gtgaacgtgc gagcctgatt 900
ctgaccaaaa gcgcgaacca cgcggtggag gaagttcgtc tgcgtaag 948

<210> SEQ ID NO 120
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 120

Met Ser Ile Lys Glu Gln Thr Leu Met Thr Pro Tyr Leu Gln Phe Asp
1 5 10 15

Arg Asn Gln Trp Ala Gly Leu Arg Asp Ser Val Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Glu Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ser Lys
260 265 270

Thr Ala Met Thr Ile Trp Lys Glu Met Asn Trp Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 121
<211> LENGTH: 948

<212> TYPE: DNA
<213> ORGANISM: Artificial Sequence
<220> FEATURE:
<223> OTHER INFORMATION: Pantothenate Kinase from Escherichia coli variant

<400> SEQUENCE: 121
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcctcgt 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
aaagacctga agagcggtgt gccgaatgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aattatgcga aactgaccaa ggaagaggcg atcaaaaccg cgatgaccat ttggaaggag 840
atgaaccacc tgaacctgaa gcaaaacatt ctgccgaccc gtgaacgtgc gagcctgatt 900
ctgaccaaaa gcgcaaacca cgcggtggag gaagttcgtc tgcgtaag 948

<210> SEQ ID NO 122
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 122

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Pro Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val

```
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 123
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 123

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcctcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

cgtgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagtctgatt    900

ctgaccaaaa gcgcaaacca cgttgtggag gaagttcgtc tgcgtaag                948
```

<210> SEQ ID NO 124
<211> LENGTH: 316
<212> TYPE: PRT

<213> ORGANISM: Artificial Sequence
<220> FEATURE:
<223> OTHER INFORMATION: Pantothenate Kinase from Escherichia coli variant

<400> SEQUENCE: 124

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Cys Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Arg Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Val Val Glu Glu Val Arg Leu Arg Lys
305                 310                 315
```

<210> SEQ ID NO 125
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 125

```
atgagcatca aagagcagac cctgatgacc ccgtacctgc agctggaccg taaccaatgg     60
```

```
gcggcgctgc gtgatagtaa cccgatgacc ctgagcgagg acgaaatcgc gcgtctgaag    120

ggtattaacc ctgatctgag cctggaggaa gtggcggaaa tctacctgcc gctgagccgt    180

ctgctgaact tctatattag cagcaacctg cgtcgtcagg cggttcagga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcctcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgaatgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                 948
```

<210> SEQ ID NO 126
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 126

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Pro Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Gln Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
```

195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 127
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 127
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcctcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agcgacctga agagcggtgt gccgaatgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
gggtatgcga aactgaccaa ggaagaggcg atcaaaaccg cgatgaccat ttggaaggag 840
atgaaccacc tgaacctgaa gcaaaacatt ctgccgaccc gtgaacgtgc gcgtctgatt 900
ctgaccaaaa gcgcaaacca catcgtggag gaagttcgtc tgcgtaag 948

<210> SEQ ID NO 128
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 128

Met Ser Ile Lys Glu Gln Thr Leu Met Thr Pro Tyr Leu Gln Leu Asp
1 5 10 15

```
Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Ile Val Glu Glu Val Arg Leu Arg Lys
305                 310                 315
```

<210> SEQ ID NO 129
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 129

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacg aggatctgag cctggaggaa gtggcggaat ggtacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300
```

-continued

```
aaaagcacca ccgcgcgtgt gctgcaggcg ctgctgagcc gttggccgga gcatcctcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

agtgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                 948
```

<210> SEQ ID NO 130
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 130

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Cys Ile Asn Glu Asp Leu Ser Leu
        35                  40                  45

Glu Glu Val Ala Glu Trp Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
```

```
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 131
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 131

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

aaagacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

gggtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca catcgtggag gaagttcgtc tgcgtaag                  948


<210> SEQ ID NO 132
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 132

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60
```

```
Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 133
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 133

```
atgagcatca aagagcagac cctgatgacc ccgtacctgc aactggaccg taacgcgtgg      60

gcggggctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

agtgacctga agagcggtgt gccgcaagtt accgcgccgg tgtacagcca cctgatctat     540

gatgttattc cggacggcga taaaaccgtg gttcagccgg acatcctgat tctggagggt     600
```

```
ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgctgtggag gaagttcgtc tgcgtaag                 948
```

```
<210> SEQ ID NO 134
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 134

Met Ser Ile Lys Glu Gln Thr Leu Met Thr Pro Tyr Leu Gln Leu Asp
1               5                   10                  15

Arg Asn Ala Trp Ala Gly Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
```

```
    290                 295                 300

Ala Asn His Ala Val Glu Glu Val Arg Leu Arg Lys
305                 310                 315
```

<210> SEQ ID NO 135
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 135

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacc ctgatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcctcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

cgtgacctga agagcggtgt gccgaatgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

ccgtatgcga aactgaccaa ggaagaggcg atcaaaaccg cgatgaccat ttggaaggag    840

atgaaccacc tgaacctgaa gcaaaacatt ctgccgaccc gtgaacgtgc gcgtctgatt    900

ctgaccaaaa gcgcaaacca cgctgtggag gaagttcgtc tgcgtaag                 948
```

<210> SEQ ID NO 136
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 136

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Pro Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110
```

Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Arg Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Ala Val Glu Glu Val Arg Leu Arg Lys
305                 310                 315

<210> SEQ ID NO 137
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 137
atgagcatca aagagcagac cctgatgacc ccgtacctgc agctggaccg taaccaatgg    60
gcggcgctgc gtgatagtaa cccgatgacc ctgagcgagg acgaaatcgc gcgtctgaag   120
cggattaacg aggatctgag cctggaggaa gtggcggaaa tctacctgcc gctgagccgt   180
ctgctgaact tctatattag cagcaacctg cgtcgtcagg cggttctgga acagtttctg   240
ggtaccaacg gccagcgtat cccgtatatc attagcattg cgggtagcgt ggcggttggc   300
aaaagcacca ccgcgcgtgt gctgcaggcg ctgctgagcc gttggccgga gcatcgtcgt   360
gttgaactga tcaccaccga cggcttcctg cacccgaacc aagtgctgaa ggagcgtggt   420
ctgatgaaga aaaagggttt cccggaaagc tacgatatgc accgtctggt gaaatttgtt   480
agcgacctga agagcggtgt gccgaacgtt accgcgccgg tgtacagcca cctgatctat   540
gatgttattc cggacggcga taaaaccgtg gttcagccgg acatcctgat tctggagggt   600
ctgaacgtgc tgcaaagcgg catggactat ccgcacgatc cgcaccacgt gtttgttagc   660
gacttcgtgg attttagcat ctacgttgac gcgccggagg atctgctgca gacctggtac   720
attaaccgtt tcctgaaatt tcgtgagggt gcgttcaccg acccggatag ctactttcac   780
aactatgcga aactgaccaa ggaagaggcg atcaaaaccg cgatgaccat ttggaaggag   840

```
atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                 948


<210> SEQ ID NO 138
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 138

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Arg Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 139
<211> LENGTH: 948
<212> TYPE: DNA
```

<213> ORGANISM: Artificial Sequence
<220> FEATURE:
<223> OTHER INFORMATION: Pantothenate Kinase from Escherichia coli variant

<400> SEQUENCE: 139

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacc aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agtgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

ccgtatgcga aactgaccaa ggaagaggcg atcaaaaccg cgatgaccat ttggaaggag    840

atgaaccacc tgaacctgaa gcaaaacatt ctgccgaccc gtgaacgtgc gcgtctgatt    900

ctgaccaaaa gcgcaaacca cgttgtggag gaagttcgtc tgcgtaag                 948
```

<210> SEQ ID NO 140
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 140

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Cys Ile Asn Gln Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160
```

```
Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Val Val Glu Glu Val Arg Leu Arg Lys
305                 310                 315
```

<210> SEQ ID NO 141
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 141

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

agtgacctga agagcggtgt gccgaatgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aattatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca cgcggtggag gaagttcgtc tgcgtaag                  948
```

<210> SEQ ID NO 142
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 142

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 143
<211> LENGTH: 948
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 143
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
tgtattaacc aggatctgag cctggaggaa gtggcggaag tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcctaag 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
agtgacctga agagcggtgt gccgaatgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
gggtatgcga aactgaccaa ggaagaggcg atcaaaaccg cgatgaccat ttggaaggag 840
atgaaccacc tgaacctgaa gcaaaacatt ctgccgaccc gtgaacgtgc gcgtctgatt 900
ctgaccaaaa gcgcaaacca cgttgtggag gaagttcgtc tgcgtaag 948

<210> SEQ ID NO 144
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 144

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Cys Ile Asn Gln Asp Leu Ser Leu
35 40 45

Glu Glu Val Ala Glu Val Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Pro Lys Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

```
Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Val Val Glu Glu Val Arg Leu Arg Lys
305                 310                 315


<210> SEQ ID NO 145
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 145

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacc aggatctgag cctggaggaa gtggcggaat ggtacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcctcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agtgacctga agagcggtgt gccgcaagtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aactatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca cgcggtggag gaagttcgtc tgcgtaag                  948


<210> SEQ ID NO 146
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 146

Met Ser Ile Lys Glu Gln Thr Leu Met Thr Pro Tyr Leu Gln Leu Asp
1               5                   10                  15
```

```
Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Gln Asp Leu Ser Leu
        35                  40                  45

Glu Glu Val Ala Glu Trp Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 147
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 147

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaat ggtacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatgcccgt     360
```

```
gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                948


<210> SEQ ID NO 148
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 148

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Trp Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Ala Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255
```

Ser Tyr Phe His Asn Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 149
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 149
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
agtgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaaccacc tgaacctgaa gcaaaacatt ctgccgaccc gtgaacgtgc gagcctgatt 900
ctgaccaaaa gcgcaaacca cgttgtggag gaagttcgtc tgcgtaag 948

<210> SEQ ID NO 150
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 150

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

-continued

```
Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Val Val Glu Glu Val Arg Leu Arg Lys
305                 310                 315
```

<210> SEQ ID NO 151
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 151

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacc aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcataaaaag     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

cgtgacctga agagcggtgt gccgaatgtt accgcgccgg tgtacagcca cctgatctat     540

gatgttattc cggacggcga taaaaccgtg gttcagccgg acatcctgat tctggagggt     600
```

```
ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                 948
```

<210> SEQ ID NO 152
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 152

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Gln Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Lys Lys Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Arg Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300
```

Ala Asn His Ala Val Glu Glu Val Arg Leu Arg Lys
305 310 315

<210> SEQ ID NO 153
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 153
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacc aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcctcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
cgtgacctga agagcggtgt gccgaatgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
ccgtatgcga aactgaccaa ggaagaggcg atcaaaaccg cgatgaccat ttggaaggag 840
atgaaccacc tgaacctgaa gcaaaacatt ctgccgaccc gtgaacgtgc gcgtctgatt 900
ctgaccaaaa gcgcaaacca cgcggtggag gaagttcgtc tgcgtaag 948

<210> SEQ ID NO 154
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 154

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Gln Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

-continued

```
Ser Arg Trp Pro Glu His Pro Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Arg Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Ala Val Glu Glu Val Arg Leu Arg Lys
305                 310                 315
```

<210> SEQ ID NO 155
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 155

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacc aggatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatgccaag    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

agtgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

ccgtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900
```

ctgaccaaaa gcgcaaacca cgctgtggag gaagttcgtc tgcgtaag 948

<210> SEQ ID NO 156
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 156

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Cys Ile Asn Gln Asp Leu Ser Leu
35 40 45

Glu Glu Val Ala Glu Val Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Ala Lys Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val
145 150 155 160

Ser Asp Leu Lys Ser Gly Val Pro Gln Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Pro Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Thr Lys Ser
290 295 300

Ala Asn His Ala Val Glu Glu Val Arg Leu Arg Lys
305 310 315

<210> SEQ ID NO 157
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 157

```
atgagcatca aagagcagac cctgatgacc ccgtacctgg aactggaccg taacacgtgg      60

gcggcgctgc gtgatagtaa cccgatgacc ctgagcgagg acgaaatcgc gcgtctgaag     120

tgtattaacg aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

aaagacctga agagcggtgt gccgaatgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

ccgtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca cgcggtggag gaagttcgtc tgcgtaag                 948
```

<210> SEQ ID NO 158
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 158

```
Met Ser Ile Lys Glu Gln Thr Leu Met Thr Pro Tyr Leu Glu Leu Asp
1               5                   10                  15

Arg Asn Thr Trp Ala Ala Leu Arg Asp Ser Asn Pro Met Thr Leu Ser
            20                  25                  30

Glu Asp Glu Ile Ala Arg Leu Lys Cys Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160
```

```
Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 159
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 159

```
atgagcatca aagagcagac cctgatgacc ccgtacctgc agctggaccg taaccaatgg     60

gcggggctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcggctgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt ggaagttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ctggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                 948
```

<210> SEQ ID NO 160
<211> LENGTH: 316
<212> TYPE: PRT
<213> ORGANISM: Artificial Sequence
<220> FEATURE:

<223> OTHER INFORMATION: Pantothenate Kinase from Escherichia coli
variant

<400> SEQUENCE: 160

```
Met Ser Ile Lys Glu Gln Thr Leu Met Thr Pro Tyr Leu Gln Leu Asp
1               5                   10                  15

Arg Asn Gln Trp Ala Gly Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Ala Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Glu Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 161
<211> LENGTH: 948
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 161

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120
```

```
ggtattaacc ctgatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

agtgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gcgtctgatt    900

ctgaccaaaa gcgcaaacca cgcggtggag gaagttcgtc tgcgtaag                 948
```

```
<210> SEQ ID NO 162
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 162

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Pro Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205
```

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Ala Val Glu Glu Val Arg Leu Arg Lys
305                 310                 315

<210> SEQ ID NO 163
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 163
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcaccgtcgt 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
agtgacctga agagcggtgt gccgcaagtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
ccgtatgcga aactgaccaa ggaagaggcg atcaaaaccg cgatgaccat ttggaaggag 840
atgaaccacc tgaacctgaa gcaaaacatt ctgccgaccc gtgaacgtgc gcgtctgatt 900
ctgaccaaaa gcgcaaacca catcgtggag gaagttcgtc tgcgtaag 948

<210> SEQ ID NO 164
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 164

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser

```
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Ile Val Glu Glu Val Arg Leu Arg Lys
305                 310                 315
```

<210> SEQ ID NO 165
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 165

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360
```

```
gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

cgtgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagtctgatt    900

ctgaccaaaa gcgcaaacca cgttgtggag gaagttcgtc tgcgtaag                948
```

```
<210> SEQ ID NO 166
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 166

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Arg Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255
```

Ser Tyr Phe His Asn Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Thr Lys Ser
290 295 300

Ala Asn His Val Val Glu Glu Val Arg Leu Arg Lys
305 310 315

<210> SEQ ID NO 167
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 167
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcataaacgt 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
cgtgacctga agagcggtgt gccgcaagtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
ccgtatgcga aactgaccaa ggaagaggcg atcaaaaccg cgatgaccat ttggaaggag 840
atgaaccacc tgaacctgaa gcaaaacatt ctgccgaccc gtgaacgtgc gagcctgatt 900
ctgaccaaaa gcgcaaacca cgcggtggag gaagttcgtc tgcgtaag 948

<210> SEQ ID NO 168
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 168

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu

-continued

```
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Lys Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Arg Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 169
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 169

atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacc aggatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcctaag    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

aaagacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660
```

```
gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gcgtctgatt    900

ctgaccaaaa gcgcaaacca cgctgtggag gaagttcgtc tgcgtaag                 948


<210> SEQ ID NO 170
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 170

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Cys Ile Asn Gln Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Lys Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Lys Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300
```

Ala Asn His Ala Val Glu Glu Val Arg Leu Arg Lys
305 310 315

<210> SEQ ID NO 171
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 171
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
tgtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcctcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
cgtgacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aattatgcga aactgaccaa ggaagaggcg atcaaaaccg cgatgaccat ttggaaggag 840
atgaaccacc tgaacctgaa gcaaaacatt ctgccgaccc gtgaacgtgc gagtctgatt 900
ctgaccaaaa gcgcaaacca cgttgtggag gaagttcgtc tgcgtaag 948

<210> SEQ ID NO 172
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 172

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Cys Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Pro Arg Val Glu Leu Ile Thr Thr Asp Gly

```
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Arg Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Val Val Glu Glu Val Arg Leu Arg Lys
305                 310                 315
```

<210> SEQ ID NO 173
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 173

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacc aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agcgacctga agagcggtgt gccgaatgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

ccgtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900
```

ctgaccaaaa gcgcaaacca cgttgtggag gaagttcgtc tgcgtaag 948

<210> SEQ ID NO 174
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 174

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Gln Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Pro Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Thr Lys Ser
290 295 300

Ala Asn His Val Val Glu Glu Val Arg Leu Arg Lys
305 310 315

<210> SEQ ID NO 175
<211> LENGTH: 948
<212> TYPE: DNA
<213> ORGANISM: Artificial Sequence
<220> FEATURE:

<223> OTHER INFORMATION: Pantothenate Kinase from Escherichia coli variant

<400> SEQUENCE: 175

```
atgagcatca aagagcagac cctgatgacc ccgtacctgc agctggaccg taaccaatgg      60
gcggcgctgc gtgatagtaa cccgatgacc ctgagcgagg acgaaatcgc gcgtctgaag     120
ggtattaacc ctgatctgag cctggaggaa gtggcggaat ggtacctgcc gctgagccgt     180
ctgctgaact tctatattag cagcaacctg cgtcgtcagg cggttctgga acagtttctg     240
ggtaccaacg gccagcgtat cccgtatatc attagcattg cgggtagcgt ggcggttggc     300
aaaagcacca ccgcgcgtgt gctgcaggcg ctgctgagcc gttggccgga gcatgccaag     360
gttgaactga tcaccaccga cggcttcctg cacccgaacc aagtgctgaa ggagcgtggt     420
ctgatgaaga aaaagggttt cccggaaagc tacgatatgc accgtctggt gaaatttgtt     480
agcgacctga agagcggtgt gccgcaagtt accgcgccgg tgtacagcca cctgatctat     540
gatgttattc cggacggcga taaaaccgtg gttcagccgg acatcctgat tctggagggt     600
ctgaacgtgc tgcaaagcgg catggactat ccgcacgatc cgcaccacgt gtttgttagc     660
gacttcgtgg attttagcat ctacgttgac gcgccggagg atctgctgca gacctggtac     720
attaaccgtt tcctgaaatt tcgtgagggt gcgttcaccg acccggatag ctactttcac     780
gggtatgcga aactgaccaa ggaagaggcg atcaaaaccg cgatgaccat ttggaaggag     840
atgaaccacc tgaacctgaa gcaaaacatt ctgccgaccc gtgaacgtgc gagcctgatt     900
ctgaccaaaa gcgcaaacca cgcggtggag gaagttcgtc tgcgtaag                  948
```

<210> SEQ ID NO 176
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 176

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Pro Asp Leu Ser Leu
        35                  40                  45

Glu Glu Val Ala Glu Trp Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Ala Lys Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Gln Val Thr Ala Pro Val Tyr Ser
```

```
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 177
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 177

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtgtcg gaagttcgtc tgcgtaag                 948
```

<210> SEQ ID NO 178
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 178

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Ser Glu Val Arg Leu Arg Lys
305                 310                 315
```

<210> SEQ ID NO 179
<211> LENGTH: 948
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 179

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120
```

```
tgtattaacc aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

ccgtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgttgtggag gaagttcgtc tgcgtaag                 948
```

```
<210> SEQ ID NO 180
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 180

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Cys Ile Asn Gln Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
```

```
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Val Val Glu Glu Val Arg Leu Arg Lys
305                 310                 315
```

<210> SEQ ID NO 181
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 181

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacc ctgatctgag cctggaggaa gtggcggaat ggtacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcctcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaatgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gcgtctgatt    900

ctgaccaaaa gcacaaacca cgcggtggag gaagttcgtc tgcgtaag                 948
```

<210> SEQ ID NO 182
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 182

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30
```

Glu Asp Glu Ile Ala Arg Leu Lys Cys Ile Asn Pro Asp Leu Ser Leu
35 40 45

Glu Glu Val Ala Glu Trp Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Pro Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Arg Leu Ile Leu Thr Lys Ser
290 295 300

Thr Asn His Ala Val Glu Glu Val Arg Leu Arg Lys
305 310 315

<210> SEQ ID NO 183
<211> LENGTH: 948
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 183
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcaacgt 360
gttgaactga tcaccaccga cggcttcctg cacccgaacc aagtgctgaa ggagcgtggt 420

```
ctgatgaaga aaaagggttt cccggaaagc tacgatatgc accgtctggt gaaatttgtt    480

agtgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgctgtggag gaagttcgtc tgcgtaag                 948
```

<210> SEQ ID NO 184
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 184

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Gln Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
```

```
        260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 185
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 185

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacc aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

aaagacctga agagcggtgt gccgcaagtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

aattatgcga aactgaccaa ggaagaggcg atcaaaaccg cgatgaccat ttggaaggag     840

atgaaccacc tgaacctgaa gcaaaacatt ctgccgaccc gtgaacgtgc gagtctgatt     900

ctgaccaaaa gcgcaaacca cgctgtggag gaagttcgtc tgcgtaag                  948


<210> SEQ ID NO 186
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 186

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Gln Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80
```

```
Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 187
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 187

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacc ctgatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcataaacgt    360

gttgaactga tcaccaccga cggcttcctg caccccgaacc aagtgctgaa ggagcgtggt    420

ctgatgaaga aaaagggttt cccggaaagc tacgatatgc accgtctgat gaaatttgtt    480

aaagacctga agagcggtgt gccgaatgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660
```

-continued

```
gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagtctgatt    900

ctgaccaaaa gcgcaaacca cgcggtggag gaagttcgtc tgcgtaag                  948


<210> SEQ ID NO 188
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 188

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Pro Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Lys Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
```

305 310 315

<210> SEQ ID NO 189
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 189
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacc aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcgtcgt 360
gttgaactga tcaccaccga cggcttcctg cacccgaacc aagtgctgaa ggagcgtggt 420
ctgatgaaga aaaagggttt cccggaaagc tacgatatgc accgtctggt gaaatttgtt 480
agtgacctga agagcggtgt gccgaatgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
gggtatgcga aactgaccaa ggaagaggcg atcaaaaccg cgatgaccat ttggaaggag 840
atgaaccacc tgaacctgaa gcaaaacatt ctgccgaccc gtgaacgtgc gcgtctgatt 900
ctgaccaaaa gcgcaaacca cgttgtggag gaagttcgtc tgcgtaag 948

<210> SEQ ID NO 190
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 190

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Gln Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

```
Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Val Val Glu Glu Val Arg Leu Arg Lys
305                 310                 315


<210> SEQ ID NO 191
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 191

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacc ctgatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcctaag     360

gttgaactga tcaccaccga cggcttcctg cacccgaacc aagtgctgaa ggagcgtggt     420

ctgatgaaga aaaagggttt cccggaaagc tacgatatgc accgtctggt gaaatttgtt     480

agtgacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

ccgtatgcga aactgaccaa ggaagaggcg atcaaaaccg cgatgaccat ttggaaggag     840

atgaaccacc tgaacctgaa gcaaaacatt ctgccgaccc gtgaacgtgc gagtctgatt     900

ctgaccaaaa gcgcaaacca cgcggtggag gaagttcgtc tgcgtaag                  948
```

<210> SEQ ID NO 192
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 192

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Pro Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Pro Lys Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 193
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 193
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaaa tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatcgtaag 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
agtgacctga agagcggtgt gccgaatgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
ccgtatgcga aactgaccaa ggaagaggcg atcaaaaccg cgatgaccat ttggaaggag 840
atgaaccacc tgaacctgaa gcaaaacatt ctgccgaccc gtgaacgtgc gagcctgatt 900
ctgaccaaaa gcgcaaacca cgcggtggag gaagttcgtc tgcgtaag 948

<210> SEQ ID NO 194
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 194

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Lys Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val
145 150 155 160

Ser Asp Leu Lys Ser Gly Val Pro Asn Val Thr Ala Pro Val Tyr Ser
165 170 175

```
His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Pro Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 195
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 195

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctggctaaaa gcgcaaacca cgcggtggag gaagttcgtc tgcgtaag                 948
```

<210> SEQ ID NO 196
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 196

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Ile Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Val Lys Phe Val
145 150 155 160

Ser Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr
225 230 235 240

Ile Asn Arg Phe Leu Lys Phe Arg Glu Gly Ala Phe Thr Asp Pro Asp
245 250 255

Ser Tyr Phe His Asn Tyr Ala Lys Leu Thr Lys Glu Glu Ala Ile Lys
260 265 270

Thr Ala Met Thr Ile Trp Lys Glu Met Asn His Leu Asn Leu Lys Gln
275 280 285

Asn Ile Leu Pro Thr Arg Glu Arg Ala Ser Leu Ile Leu Ala Lys Ser
290 295 300

Ala Asn His Ala Val Glu Glu Val Arg Leu Arg Lys
305 310 315

<210> SEQ ID NO 197
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 197
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacc aggatctgag cctggaggaa gtggcggaag tctacctgcc gctgagccgt 180
ctgctgaact tctatattag cagcaacctg cgtcgtcagg cggttctgga acagtttctg 240
ggtaccaacg gccagcgtat cccgtatatc attagcattg cgggtagcgt ggcggttggc 300
aaaagcacca ccgcgcgtgt gctgcaggcg ctgctgagcc gttggccgga gcatgccaag 360
gttgaactga tcaccaccga cggcttcctg cacccgaacc aagtgctgaa ggagcgtggt 420
ctgatgaaga aaaagggttt cccggaaagc tacgatatgc accgtctgat gaaatttgtt 480
cgtgacctga agagcggtgt gccgcaagtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
aactatgcga aactgaccaa ggaagaggcg atcaaaaccg cgatgaccat ttggaaggag 840
atgaaccacc tgaacctgaa gcaaaacatt ctgccgaccc gtgaacgtgc gagtctgatt 900
ctgaccaaaa gcgcaaacca cgctgtggag gaagttcgtc tgcgtaag 948

<210> SEQ ID NO 198
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 198

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Gln Asp Leu Ser Leu
35 40 45

Glu Glu Val Ala Glu Val Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Ala Lys Val Glu Leu Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val
145 150 155 160

Arg Asp Leu Lys Ser Gly Val Pro Gln Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

```
Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315


<210> SEQ ID NO 199
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 199

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaaa tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcaccgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

cgtgacctga agagcggtgt gccgcaagtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

gggtatgcga aactgaccaa ggaagaggcg atcaaaaccg cgatgaccat ttggaaggag     840

atgaaccacc tgaacctgaa gcaaaacatt ctgccgaccc gtgaacgtgc gagtctgatt     900

ctgaccaaaa gcgcaaacca cgctgtggag gaagttcgtc tgcgtaag                  948


<210> SEQ ID NO 200
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 200

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30
```

```
Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Arg Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 201
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 201

```
atgagcatca aagagcagac cctgatgacc ccgtacctgc aactggaccg taacacgtgg     60

gcggggctgc gtgatagtaa cccgatgacc ctgagcgagg acgaaatcgc gcgtctgaag    120

tgtattaacc ctgatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatgcccgt    360

gttgaactga tcaccaccga cggcttcctg cacccgaacc aagtgctgaa ggagcgtggt    420
```

-continued

```
ctgatgaaga aaaagggttt cccggaaagc tacgatatgc accgtctgat gaaatttgtt    480

agtgacctga agagcggtgt gccgaatgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gcgtctgatt    900

ctgaccaaaa gcgcaaacca catcgtggag gaagttcgtc tgcgtaag                 948
```

<210> SEQ ID NO 202
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 202

```
Met Ser Ile Lys Glu Gln Thr Leu Met Thr Pro Tyr Leu Gln Leu Asp
1               5                   10                  15

Arg Asn Thr Trp Ala Gly Leu Arg Asp Ser Asn Pro Met Thr Leu Ser
            20                  25                  30

Glu Asp Glu Ile Ala Arg Leu Lys Cys Ile Asn Pro Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Ala Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270
```

```
Thr Ala Met Thr Ile Trp Lys Glu Met Asn His Leu Asn Leu Lys Gln
        275                 280                 285

Asn Ile Leu Pro Thr Arg Glu Arg Ala Arg Leu Ile Leu Thr Lys Ser
    290                 295                 300

Ala Asn His Ile Val Glu Glu Val Arg Leu Arg Lys
305                 310                 315


<210> SEQ ID NO 203
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 203

atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

agcgacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagcgt gcgttcaccg acccggatag ctactttcac    780

aactatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca cgcggtggag gaagttcgtc tgcgtaag                 948


<210> SEQ ID NO 204
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 204

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80
```

-continued

```
Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Arg Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 205
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 205

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

tgtattaacc ctgatctgag cctggaggaa gtggcggaaa tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcaccgtcgt    360

gttgaactga tcaccaccga cggcttcctg cacccgaacc aagtgctgaa ggagcgtggt    420

ctgatgaaga aaaagggttt cccggaaagc tacgatatgc accgtctggt gaaatttgtt    480

cgtgacctga agagcggtgt gccgcaagtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720
```

```
attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagtctgatt    900

ctgaccaaaa gcgcaaacca cgcggtggag gaagttcgtc tgcgtaag                948


<210> SEQ ID NO 206
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 206

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Cys Ile Asn Pro Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Arg Asp Leu Lys Ser Gly Val Pro Gln Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315
```

<210> SEQ ID NO 207
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 207

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaacc tgtatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948
```

<210> SEQ ID NO 208
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 208

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Leu
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125
```

```
Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315


<210> SEQ ID NO 209
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 209

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

aaagacctga agagcggtgt gccgaacgtt accgcgccgg tgtacagcca cctgatcgag     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

gggtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca catcgtggag gaagttcgtc tgcgtaag                  948
```

<210> SEQ ID NO 210
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 210

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Glu Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 211
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 211

```
atgagcatca aagagcagac cctgatgacc ccgtacctgc agctggaccg taaccaatgg     60
gcggcgctgc gtgatagtaa cccgatgacc ctgagcgagg acgaaatcgc gcgtctgaag    120
ggtattaacg aggatctgag cctggaggaa gtggcggaag tctacctgcc gctgagccgt    180
ctgctgaact tctatattag cagcaacctg cgtcgtcagg cggttctgga acagtttctg    240
ggtaccaacg gccagcgtat cccgtatatc attagcattg cgggtagcgt ggcggttggc    300
aaaagcacca ccgcgcgtgt gctgcaggcg ctgctgagcc gttggccgga gcatcgtcgt    360
gttgaatgga tcaccaccga cggcttcctg cacccgaacc aagtgctgaa ggagcgtggt    420
ctgatgaaga aaaagggttt cccggaaagc tacgatatgc accgtctgat gaaatttgtt    480
aaagacctga agagcggtgt gccgaacgtt accgcgccgg tgtacagcca cctgatctat    540
gatgttattc cggacggcga taaaaccgtg gttcagccgg acatcctgat tctggagggt    600
ctgaacgtgc tgcaaagcgg catggactat ccgcacgatc cgcaccacgt gtttgttagc    660
gacttcgtgg attttagcat ctacgttgac gcgccggagg atctgctgca gacctggtac    720
attaaccgtt tcctgaaatt tcgtgagggt gcgttcaccg acccggatag ctactttcac    780
gggtatgcga aactgaccaa ggaagaggcg atcaaaaccg cgatgaccat ttggaaggag    840
atgaaccacc tgaacctgaa gcaaaacatt ctgccgaccc gtgaacgtgc gagcctgatt    900
ctgaccaaaa gcgcaaacca catcgtggag gaagttcgtc tgcgtaag                 948
```

<210> SEQ ID NO 212
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 212

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Trp Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175
```

-continued

```
His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 213
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 213

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc gggtgctgaa ggagcgtggt     420

ctgatgaaga aaaagggttt cccggaaagc tacgatatgc accgtctgat gaaatttgtt     480

aaagacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

gggtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca catcgtggag gaagttcgtc tgcgtaag                  948
```

<210> SEQ ID NO 214
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 214

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Arg Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315

<210> SEQ ID NO 215
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 215
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aggatctgag cctggaggaa gtggcggaag tctacctgcc gctgagccgt 180

```
ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaatgga tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                948
```

```
<210> SEQ ID NO 216
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 216

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Trp Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220
```

```
Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315


<210> SEQ ID NO 217
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 217

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tctcgaccga cggcttcctg cacccgaacc aagtgctgaa ggagcgtggt     420

ctgatgaaga aaaagggttt cccggaaagc tacgatatgc accgtctgat gaaatttgtt     480

aaagacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

gggtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca catcgtggag gaagttcgtc tgcgtaag                 948


<210> SEQ ID NO 218
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 218

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
```

```
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Ser Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 219
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 219

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcggtaccga cggcttcctg cacccgaacc aagtgctgaa ggagcgtggt     420

ctgatgaaga aaaagggttt cccggaaagc tacgatatgc accgtctgat gaaatttgtt     480
```

```
aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948
```

```
<210> SEQ ID NO 220
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 220

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Gly Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270
```

```
Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315


<210> SEQ ID NO 221
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 221

atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaacata tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948


<210> SEQ ID NO 222
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 222

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
```

```
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315


<210> SEQ ID NO 223
<211> LENGTH: 948
<212> TYPE: DNA
<213> ORGANISM: Artificial Sequence
<220> FEATURE:
<223> OTHER INFORMATION: Pantothenate Kinase from Escherichia coli
      variant

<400> SEQUENCE: 223

atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cagcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaactga tcaccaccga cggcttcctg cacccgaacc aagtgctgaa ggagcgtggt     420

ctgatgaaga aaaagggttt cccggaaagc tacgatatgc accgtctgat gaaatttgtt     480

aaagacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720
```

```
attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                948


<210> SEQ ID NO 224
<211> LENGTH: 316
<212> TYPE: PRT
<213> ORGANISM: Artificial Sequence
<220> FEATURE:
<223> OTHER INFORMATION: Pantothenate Kinase from Escherichia coli
      variant

<400> SEQUENCE: 224

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Gln Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 225
<211> LENGTH: 948
<212> TYPE: DNA
<213> ORGANISM: Artificial Sequence
<220> FEATURE:
<223> OTHER INFORMATION: Pantothenate Kinase from Escherichia coli
variant

<400> SEQUENCE: 225

```
atgagcatca aagagcagac cctgatgacc ccgtacctgc agctggaccg taaccaatgg     60

gcggcgctgg ctgatagtaa cccgatgacc ctgagcgagg acgaaatcgc gcgtctgaag    120

ggtattaacg aggatctgag catggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948
```

<210> SEQ ID NO 226
<211> LENGTH: 316
<212> TYPE: PRT
<213> ORGANISM: Artificial Sequence
<220> FEATURE:
<223> OTHER INFORMATION: Pantothenate Kinase from Escherichia coli
variant

<400> SEQUENCE: 226

```
Met Ser Ile Lys Glu Gln Thr Leu Met Thr Pro Tyr Leu Gln Leu Asp
1               5                   10                  15

Arg Asn Gln Trp Ala Ala Leu Ala Asp Ser Asn Pro Met Thr Leu Ser
            20                  25                  30

Glu Asp Glu Ile Ala Arg Leu Lys Gly Ile Asn Glu Asp Leu Ser Met
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
```

-continued

```
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 227
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 227

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attggtattg cgggtagcgt ggcggttggc    300

aaaagcacca ccgcgcgtgt gctgcaggcg ctgctgagcc gttggccgga gcatcgtcgt    360

gttgaactga tcaccaccga cggcttcctg cacccgaacc aagtgctgaa ggagcgtggt    420

ctgatgaaga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

atgaccaaaa gcgcaaacca catcgtggag gaagttcgtc tgcgtaag                 948
```

<210> SEQ ID NO 228
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 228

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Gly Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Met Thr Lys Ser
    290                 295                 300

Ala Asn His Ile Val Glu Glu Val Arg Leu Arg Lys
305                 310                 315
```

<210> SEQ ID NO 229
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 229

```
atgagcatca aagagcagac cctgatgacc ccgtacctgc agctggaccg taaccaatgg     60
gcggcgctgc gtgatagtaa cccgatgacc ctgagcgagg acgaaatcgc gcgtctgaag    120
ggtattaacg aggatctgag cctggaggaa gtggcggaag tctacctgcc gctgagccgt    180
ctgctgaact tctatattag cagcaacctg cgtcgtcagg cggttctgga acagtttctg    240
ggtaccaacg gccagcgtat cccgtatatc attagcattg cgggtagcgt ggcggttggc    300
aaaagcacca ccgcgcgtgt gctgcaggcg ctgctgagcc gttggccgga gcatcgtcgt    360
gttgaacata tcaccaccga cggcttcctg cacccgaacc aagtgctgaa ggagcgtggt    420
ctgatgggga aaaagggttt cccggaaagc tacgatatgc accgtctgat gaaatttgtt    480
aaagacctga agagcggtgt gccgaacgtt accgcgccgg tgtacagcca cctgatctat    540
gatgttattc cggacggcga taaaaccgtg gttcagccgg acatcctgat tctggagggt    600
ctgaacgtgc tgcaaagcgg catggactat ccgcacgatc cgcaccacgt gtttgttagc    660
gacttcgtgg attttagcat ctacgttgac gcgccggagg atctgctgca gacctggtac    720
attaaccgtt tcctgaaatt tcgtgagggt gcgttcaccg acccggatag ctactttcac    780
gggtatgcga aactgaccaa ggaagaggcg atcaaaaccg cgatgaccat ttggaaggag    840
atgaaccacc tgaacctgaa gcaaaacatt ctgccgaccc gtgaacgtgc gagcctgatt    900
ctgaccaaaa gcgcaaacca catcgtggag gaagttcgtc tgcgtaag                 948
```

<210> SEQ ID NO 230
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 230

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
```

```
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 231
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 231

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaacata tcaccaccga cggcttcctg cacccgaacc aagtgctgaa ggagcgtggt     420

ctgatgaaga aaaagggttt cccggaaagc tacgatatgc ctcgtctgat gaaatttgtt     480

aaagacctga agagcggtgt gccgaacgtt accgcgccgg tgtacagcca cctgatctat     540

gatgttattc cggacggcga taaaaccgtg gttcagccgg acatcctgat tctggagggt     600

ctgaacgtgc tgcaaagcgg catggactat ccgcacgatc cgcaccacgt gtttgttagc     660

gacttcgtgg attttagcat ctacgttgac gcgccggagg atctgctgca gacctggtac     720

attaaccgtt tcctgaaatt tcgtgagggt gcgttcaccg acccggatag ctactttcac     780

gggtatgcga aactgaccaa ggaagaggcg atcaaaaccg cgatgaccat ttggaaggag     840

atgaaccacc tgaacctgaa gcaaaacatt ctgccgaccc gtgaacgtgc gagcctgatt     900

ctgaccaaaa gcgcaaacca catcgtggag gaagttcgtc tgcgtaag                  948
```

<210> SEQ ID NO 232
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 232

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met Pro Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 233
<211> LENGTH: 948
<212> TYPE: DNA
<213> ORGANISM: Artificial Sequence
<220> FEATURE:
<223> OTHER INFORMATION: Pantothenate Kinase from Escherichia coli variant

<400> SEQUENCE: 233

```
atgagcatca aagagcagac cctgatgacc ccgtacctgc agctggaccg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240
```

ggtaccccac accagcgtat cccgtatatc attagcattg cgggtagcgt ggcggttggc 300
aaaagcacca ccgcgcgtgt gctgcaggcg ctgctgagcc gttggccgga gcatcgtcgt 360
gttgaacaca tcaccaccga cggcttcctg cacccgaacc aagtgctgaa ggagcgtggt 420
ctgatgaaga aaaagggttt cccggaaagc tacgatatgc accgtctgat gaaatttgtt 480
aaagacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
gggtatgcga aactgaccaa ggaagaggcg atcaaaaccg cgatgaccat ttggaaggag 840
atgaaccacc tgaacctgaa gcaaaacatt ctgccgaccc gtgaacgtgc gagcctgatt 900
ctgaccaaaa gcaccaacca catcgtggag gaagttcgtc tgcgtaag 948

<210> SEQ ID NO 234
<211> LENGTH: 316
<212> TYPE: PRT
<213> ORGANISM: Artificial Sequence
<220> FEATURE:
<223> OTHER INFORMATION: Pantothenate Kinase from Escherichia coli variant

<400> SEQUENCE: 234

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Val Tyr Leu Pro Leu Ser Arg Leu Leu Asn Phe
50 55 60

Tyr Ile Ser Ser Asn Leu Arg Arg Gln Ala Val Leu Glu Gln Phe Leu
65 70 75 80

Gly Thr Pro His Gln Arg Ile Pro Tyr Ile Ile Ser Ile Ala Gly Ser
85 90 95

Val Ala Val Gly Lys Ser Thr Thr Ala Arg Val Leu Gln Ala Leu Leu
100 105 110

Ser Arg Trp Pro Glu His Arg Arg Val Glu His Ile Thr Thr Asp Gly
115 120 125

Phe Leu His Pro Asn Gln Val Leu Lys Glu Arg Gly Leu Met Lys Lys
130 135 140

Lys Gly Phe Pro Glu Ser Tyr Asp Met His Arg Leu Met Lys Phe Val
145 150 155 160

Lys Asp Leu Lys Ser Gly Val Pro Asn Val Thr Ala Pro Val Tyr Ser
165 170 175

His Leu Ile Tyr Asp Val Ile Pro Asp Gly Asp Lys Thr Val Val Gln
180 185 190

Pro Asp Ile Leu Ile Leu Glu Gly Leu Asn Val Leu Gln Ser Gly Met
195 200 205

Asp Tyr Pro His Asp Pro His His Val Phe Val Ser Asp Phe Val Asp
210 215 220

Phe Ser Ile Tyr Val Asp Ala Pro Glu Asp Leu Leu Gln Thr Trp Tyr

```
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Thr Asn His Ile Val Glu Glu Val Arg Leu Arg Lys
305                 310                 315
```

<210> SEQ ID NO 235
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 235

```
atgagcatca aagagcagac cctgatgacc ccgtaccatc agctggaccg taaccaatgg     60

gcggcgctgc gcgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaact tctatatttc gagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaacata tcaccaccga cggcttcctg cacccgaacc aagtgctgaa ggagcgtggt    420

ctgatgggga aaaagggttt cccggaaagc tacgatatgc accgtctgat gaaatttgtt    480

aaagacctga agagcggtgt gccgagcgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgagc cgcaccacgt gtttgttagc    660

gacttcgtgg attttagcat ctacgttgac gcgccggagg atctgctgca gacctggtac    720

attaaccgtt tcctgaaact gcgtgagggt gcgttcaccg acccggatag ctactttcac    780

gggtatgcga aactgaccaa ggaagaggcg atcaaaaccg cgatgaccat ttggaaggag    840

atgaacagcc tgaacctgaa gacgaacatt ctgccgaccc gtgaacgtgc gagcctgatt    900

ctgaccaaaa gcgcaaacca catcgtggag gaagttcgtc tgcgtaag                 948
```

<210> SEQ ID NO 236
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 236

```
Met Ser Ile Lys Glu Gln Thr Leu Met Thr Pro Tyr His Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
```

```
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Ser Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Glu Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Leu Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn Ser Leu Asn Leu Lys Thr
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 237
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 237

```
atgagcatca aagagcagac cctgatgacc ccgtacctgc agctggaccg taaccaatgg      60

gcggcgctgc gcgatagtaa cccgatgacc ctgagcgagg acgaaatcgc gcgtctgaag     120

ggtattaacg aggatctgag cctggatgaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360

gttgaacata tcaccaccga cggcttcctg cacccgaacc aagtgctgaa ggagcgtggt     420

ctgatgggga aaaagggttt cccggaaagc tacgatatgc accgtctgat gaaatttgtt     480

aaagacctga agagcggtgt gccgaacgtt accgcgccgg tgtacagcca cctgatctat     540

gatgttattc cggacggcga taaaaccgtg gttcagccgg acatcctgat tctggagggt     600
```

```
ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaact gcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948


<210> SEQ ID NO 238
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 238

Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Asp Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Leu Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300
```

Ala Asn His Ile Val Glu Glu Val Arg Leu Arg Lys
305 310 315

<210> SEQ ID NO 239
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 239
atgagcatca aagagcagac cctgatgacc ccgtacctgc agctggaccg taaccaatgg 60
gcggcgctgc gtgatagtaa cccgatgacc ctgagcgagg acgaaatcgc gcgtctgaag 120
ggtattaacg aagatctgag cctggaggaa gtggcggaag tctacctgcc gctgagccgt 180
ctgctgaact tctatattag cagcaacctg cgtcgtcagg cgcagctgga acagtttctg 240
ggtaccaatg gccagcgtat cccgtatatc attagcattg cgggtagcgt ggcggttggc 300
aaaagcacct ttgcgcgtgt gctgcaggcg ctgctgagcc gttggccgga gcatcgtcgt 360
gttgaacata tcaccaccga cggcttcctg cacccgaacc aagtgctgaa ggagcgtggt 420
ctgatgggga aaaagggttt cccggaaagc tacgatatgc accgtctgat gaaatttgtt 480
aaagacctga agagcggtgt gccgaacgtt accgcgccgg tgtacagcca cctgatctat 540
gatgttattc cggacggcga taaaaccgtg gttcagccgg acatcctgat tctggagggt 600
ctgaacgtgc tgcaaagcgg catggactat ccgcacgatc cgcaccacgt gtttgttagc 660
gacttcgtgg attttagcat ctacgttgac gcgccggagg atctgctgca gacctggtac 720
attaaccgtt tcctgaaatt tcgtgagggt gcgttcaccg acccggatag ctactttcac 780
gggtatgcga aactgaccaa ggaagaggcg atcaaaaccg cgatgaccat ttggaaggag 840
atgaaccacg tgaacctgaa gcaaaacatt ctgccgaccc gtgaacgtgc gagcctgatt 900
ctgaccaaaa gcgcaaacca catcgtggag gaagttcgtc tgcgtaag 948

<210> SEQ ID NO 240
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 240

Met Ser Ile Lys Glu Gln Thr Leu Met Thr Pro Tyr Leu Gln Leu Asp
1 5 10 15

Arg Asn Gln Trp Ala Ala Leu Arg Asp Ser Asn Pro Met Thr Leu Ser
20 25 30

Glu Asp Glu Ile Ala Arg Leu Lys Gly Ile Asn Glu Asp Leu Ser Leu
35 40 45

Glu Glu Val Ala Glu Val Tyr Leu Pro Leu Ser Arg Leu Leu Asn Phe
50 55 60

Tyr Ile Ser Ser Asn Leu Arg Arg Gln Ala Gln Leu Glu Gln Phe Leu
65 70 75 80

Gly Thr Asn Gly Gln Arg Ile Pro Tyr Ile Ile Ser Ile Ala Gly Ser
85 90 95

Val Ala Val Gly Lys Ser Thr Phe Ala Arg Val Leu Gln Ala Leu Leu
100 105 110

Ser Arg Trp Pro Glu His Arg Arg Val Glu His Ile Thr Thr Asp Gly
115 120 125

```
Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Val Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

```
<210> SEQ ID NO 241
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 241

atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaact tctatatttc gagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaacata tcaccaccga cggcttcctg cacccgaacc aagtgctgaa ggagcgtggt    420

ctgatgggga aaaagggttt cccggaaagc tacgatatgc accgtctgat gaaatttgtt    480

aaagacctga agagcggtgt gccgagcgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaact gcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                948
```

<210> SEQ ID NO 242
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 242

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Ser Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Leu Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

<210> SEQ ID NO 243
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 243

```
atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaact tctatattag cagcaacctg cgtcgtcagg cggttctgga acagtttctg    240

ggtaccaacg gccagcgtat cccgtatatc attagcattg cgggtagcgt ggcggttggc    300

aaaagcacca ccgcgcgtgt gctgcaggcg ctgctgagcc gttggccgga gcatcgtcgt    360

gttgaacata tcaccaccga cggcttcctg cacccgaacc aagtgctgaa ggagcgtggt    420

ctgatgggga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt gcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948
```

<210> SEQ ID NO 244
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 244

```
Met Ser Ile Lys Glu Gln Thr Leu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190
```

```
Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Leu Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315


<210> SEQ ID NO 245
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 245

atgagcatca aagagcagac cctgatgacc ccgtacctgc agctggaccg taaccaatgg     60

gcggcgctgc gtgatagtaa cccgatgacc ctgagcgagg acgaaatcgc gcgtctgaag    120

ggtattaacg aggatctgag cctggaggaa gtggcggaag tctacctgcc gctgagccgt    180

ctgctgaaca tttatattag cagcaacctg cgtcgtcagg cggttctgga acagtttctg    240

ggtaccaacg gccagcgtat cccgtatatc attagcattg cgggtagcgt ggcggttggc    300

aaaagcacct ttgcgcgtgt gctgcaggcg ctgctgagcc gttggccgga gcatcgtcgt    360

gttgaacata tcaccaccga cggcttcctg cacccgaacc aagtgctgaa ggagcgtggt    420

ctgatgggga aaaagggttt cccggaaagc tacgatatgc ctcgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaatt tcgtgagggt gcgttcaccg acccggatag ctactttcac    780

gggtatgcga aactgaccaa ggaagaggcg atcaaaaccg cgatgaccat ttggaaggag    840

atgaaccacg tgaacctgaa gcaaaacatt ctgccgaccc gtgaacgtgc gagcctgatt    900

ctgaccaaaa gcgcaaacca catcgtggag gaagttcgtc tgcgtaag                 948


<210> SEQ ID NO 246
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 246

Met Ser Ile Lys Glu Gln Thr Leu Met Thr Pro Tyr Leu Gln Leu Asp
1               5                   10                  15
```

-continued

```
Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Ile
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Phe Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met Pro Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn His Val Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```

```
<210> SEQ ID NO 247
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 247

atgagcatca aagagcagac cctgatgacc ccgtacctgc agctggagcg taaccaatgg      60

gcggcgctgc gtgatagtaa cccgatgacc ctgagcgagg acgaaatcgc gcgtctgaag     120

ggtattaacg aggatctgag cctggaggaa gtggcggaag tctacctgcc gctgagccgt     180

ctgctgaact tctatattag cagcaacctg cgtcgtcagg cggttctgga acagtttctg     240

ggtaccaacg gccagcgtat cccgtatatc attagcattg cgggtagcgt ggcggttggc     300

aaaagcacca ccgcgcgtgt gctgcaggcg ctgctgagcc gttggccgga gcatcgtcgt     360
```

```
gttgaacata tcaccaccga cggcttcctg cacccgaacc aagtgctgaa ggagcgtggt    420

ctgatgggga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaact gcgtgagggt gcgttcaccg acccggatag ctactttcac    780

gggtatgcga aactgaccaa ggaagaggcg atcaaaaccg cgatgaccat ttggaaggag    840

atgaaccacc tgaacctgaa gcaaaacatt ctgccgaccc gtgaacgtgc gagcctgatt    900

ctgaccaaaa gcgcaaacca catcgtggag gaagttcgtc tgcgtaag                 948
```

<210> SEQ ID NO 248
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 248

```
Met Ser Ile Lys Glu Gln Thr Leu Met Thr Pro Tyr Leu Gln Leu Glu
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140

Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Leu Arg Glu Gly Ala Phe Thr Asp Pro Asp
                245                 250                 255

Ser Tyr Phe His Gly Tyr Ala Lys Leu Thr Lys Glu Glu Ala Ile Lys
```

```
            260                 265                 270

Thr Ala Met Thr Ile Trp Lys Glu Met Asn His Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315


<210> SEQ ID NO 249
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 249

atgcaccatc atcatcatca tggcggtagc ggcagcatca aagagcagac cgagatgacc      60

ccgtacctgc aactggaccg taaccaatgg gcggcgctgc gtgatagtaa cccgatgacc     120

ctgagcgagg acgaaatcgc gcgtctgaag ggtattaacg aagatctgag cctggaggaa     180

gtggcggaag tctacctgcc gctgagccgt ctgctgaaca tttatattag cagcaacctg     240

cgtcgtcagg cgcagctgga acagtttctg ggtaccaatg gccagcgtat cccgtatatc     300

attagcattg cgggtagcgt ggcggttggc aaaagcacct ttgcgcgtgt gctgcaggcg     360

ctgctgagcc gttggccgga gcatcgtcgt gttgaacata tcaccaccga cggcttcctg     420

cacccgaacc aagtgctgaa ggagcgtggt ctgatgggga aaaagggttt cccggaaagc     480

tacgatatgc accgtctgat gaaatttgtt aaagacctga agagcggtgt gccgaacgtt     540

accgcgccgg tgtacagcca cctgatctat gatgttattc cggacggcga taaaaccgtg     600

gttcagccgg acatcctgat tctggagggt ctgaacgtgc tgcaaagcgg catggactat     660

ccgcacgatc cgcaccacgt gtttgttagc gacttcgtgg attttagcat ctacgttgac     720

gcgccggagg atctgctgca gacctggtac attaaccgtt tcctgaaact gcgtgagggt     780

gcgttcaccg acccggatag ctactttcac gggtatgcga aactgaccaa ggaagaggcg     840

atcaaaaccg cgatgaccat ttggaaggag atgaaccatg tgaacctgaa gcaaaacatt     900

ctgccgaccc gtgaacgtgc gagcctgatt ctgaccaaaa gcgcaaacca catcgtggag     960

gaagttcgtc tgcgtaag                                                   978


<210> SEQ ID NO 250
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 250

Met His His His His His His Gly Gly Ser Gly Ser Ile Lys Glu Gln
1               5                   10                  15

Thr Glu Met Thr Pro Tyr Leu Gln Leu Asp Arg Asn Gln Trp Ala Ala
            20                  25                  30

Leu Arg Asp Ser Asn Pro Met Thr Leu Ser Glu Asp Glu Ile Ala Arg
        35                  40                  45

Leu Lys Gly Ile Asn Glu Asp Leu Ser Leu Glu Glu Val Ala Glu Val
    50                  55                  60

Tyr Leu Pro Leu Ser Arg Leu Leu Asn Ile Tyr Ile Ser Ser Asn Leu
65                  70                  75                  80
```

Arg Arg Gln Ala Gln Leu Glu Gln Phe Leu Gly Thr Asn Gly Gln Arg
85 90 95

Ile Pro Tyr Ile Ile Ser Ile Ala Gly Ser Val Ala Val Gly Lys Ser
100 105 110

Thr Phe Ala Arg Val Leu Gln Ala Leu Leu Ser Arg Trp Pro Glu His
115 120 125

Arg Arg Val Glu His Ile Thr Thr Asp Gly Phe Leu His Pro Asn Gln
130 135 140

Val Leu Lys Glu Arg Gly Leu Met Gly Lys Lys Gly Phe Pro Glu Ser
145 150 155 160

Tyr Asp Met His Arg Leu Met Lys Phe Val Lys Asp Leu Lys Ser Gly
165 170 175

Val Pro Asn Val Thr Ala Pro Val Tyr Ser His Leu Ile Tyr Asp Val
180 185 190

Ile Pro Asp Gly Asp Lys Thr Val Val Gln Pro Asp Ile Leu Ile Leu
195 200 205

Glu Gly Leu Asn Val Leu Gln Ser Gly Met Asp Tyr Pro His Asp Pro
210 215 220

His His Val Phe Val Ser Asp Phe Val Asp Phe Ser Ile Tyr Val Asp
225 230 235 240

Ala Pro Glu Asp Leu Leu Gln Thr Trp Tyr Ile Asn Arg Phe Leu Lys
245 250 255

Leu Arg Glu Gly Ala Phe Thr Asp Pro Asp Ser Tyr Phe His Gly Tyr
260 265 270

Ala Lys Leu Thr Lys Glu Glu Ala Ile Lys Thr Ala Met Thr Ile Trp
275 280 285

Lys Glu Met Asn His Val Asn Leu Lys Gln Asn Ile Leu Pro Thr Arg
290 295 300

Glu Arg Ala Ser Leu Ile Leu Thr Lys Ser Ala Asn His Ile Val Glu
305 310 315 320

Glu Val Arg Leu Arg Lys
325

<210> SEQ ID NO 251
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 251
atgcaccatc atcatcatca tggcggtagc ggcagcatca aagagcagac cgagatgacc 60
ccgtacctgc aactggaccg taaccaatgg gcggcgctgc gtgatagtaa cccgatgacc 120
ctgagcgagg acgaaatcgc gcgtctgaag ggtattaacg aagatctgag cctggaggaa 180
gtggcggaag tctacctgcc gctgagccgt ctgctgaact tctatattag cagcaacctg 240
cgtcgtcagg cgcagctgga acagtttctg ggtaccaatg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600

```
gttcagccgg acatcctgat tctggagggt ctgaacgtgc tgcaaagcgg catggactat    660

ccgcacgatc cgcaccacgt gtttgttagc gacttcgtgg attttagcat ctacgttgac    720

gcgccggagg atctgctgca gacctggtac attaaccgtt tcctgaaact gcgtgagggt    780

gcgttcaccg acccggatag ctactttcac gggtatgcga aactgaccaa ggaagaggcg    840

atcaaaaccg cgatgaccat ttggaaggag atgaacagcg tgaacctgaa gcaaaacatt    900

ctgccgaccc gtgaacgtgc gagcctgatt ctgaccaaaa gcgcaaacca catcgtggag    960

gaagttcgtc tgcgtaag                                                  978


<210> SEQ ID NO 252
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 252

Met His His His His His His Gly Gly Ser Gly Ser Ile Lys Glu Gln
1               5                   10                  15

Thr Glu Met Thr Pro Tyr Leu Gln Leu Asp Arg Asn Gln Trp Ala Ala
            20                  25                  30

Leu Arg Asp Ser Asn Pro Met Thr Leu Ser Glu Asp Glu Ile Ala Arg
        35                  40                  45

Leu Lys Gly Ile Asn Glu Asp Leu Ser Leu Glu Glu Val Ala Glu Val
    50                  55                  60

Tyr Leu Pro Leu Ser Arg Leu Leu Asn Phe Tyr Ile Ser Ser Asn Leu
65                  70                  75                  80

Arg Arg Gln Ala Gln Leu Glu Gln Phe Leu Gly Thr Asn Gly Gln Arg
                85                  90                  95

Ile Pro Tyr Ile Ile Ser Ile Ala Gly Ser Val Ala Val Gly Lys Ser
            100                 105                 110

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Leu Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn Ser Val Asn Leu Lys Gln Asn Ile Leu Pro Thr Arg
```

290 295 300

Glu Arg Ala Ser Leu Ile Leu Thr Lys Ser Ala Asn His Ile Val Glu
305 310 315 320

Glu Val Arg Leu Arg Lys
325

<210> SEQ ID NO 253
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 253
atgcaccatc atcatcatca tggcggtagc ggcagcatca aagagcagac cgagatgacc 60
ccgtaccatg cgctggaccg taaccaatgg gcggcgctgc gtgatagtaa cccgatgacc 120
ctgagcgagg acgaaatcgc gcgtctgaag ggtattaacg aagatctgag cctggaggaa 180
gtggcggaag tctacctgcc gctgagccgt ctgctgaact tctatattag cagcaacctg 240
cgtcgtcagg cgcagctgga acagtttctg ggtacccctg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600
gttcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaact gcgtgagggt 780
gcgttcaccg acccggatag ctactttcac gggtatgcga aactgaccaa ggaagaggcg 840
atcaaaaccg cgatgaccat ttggaaggag atgaaccatg tgaacctgaa gcaaaacatt 900
ctgccgaccc gtgaacgtgc gagcctgatt ctgaccaaaa gcgcaaacca catcgtggag 960
gaagttcgtc tgcgtaag 978

<210> SEQ ID NO 254
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 254

Met His His His His His His Gly Gly Ser Gly Ser Ile Lys Glu Gln
1 5 10 15

Thr Glu Met Thr Pro Tyr His Ala Leu Asp Arg Asn Gln Trp Ala Ala
20 25 30

Leu Arg Asp Ser Asn Pro Met Thr Leu Ser Glu Asp Glu Ile Ala Arg
35 40 45

Leu Lys Gly Ile Asn Glu Asp Leu Ser Leu Glu Glu Val Ala Glu Val
50 55 60

Tyr Leu Pro Leu Ser Arg Leu Leu Asn Phe Tyr Ile Ser Ser Asn Leu
65 70 75 80

Arg Arg Gln Ala Gln Leu Glu Gln Phe Leu Gly Thr Pro Gly Gln Arg
85 90 95

```
Ile Pro Tyr Ile Ile Ser Ile Ala Gly Ser Val Ala Val Gly Lys Ser
            100                 105                 110

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Leu Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn His Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
                325
```

<210> SEQ ID NO 255
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 255

```
atgcaccatc atcatcatca tggcggtagc ggcagcatca aagagcagac cgagatgacc     60

ccgtacctgc aactggaccg taaccaatgg gcggcgctgc gtgatagtaa cccgatgacc    120

ctgagcgagg acgaaatcgc gcgtctgaag ggtattaacg aagatctgag cctggaggaa    180

gtggcggaag tctacctgcc gctgagccgt ctgctgaaca tttatattag cagcaacctg    240

cgtcgtcagg cgcagctgga acagtttctg ggtaccaatg gccagcgtat cccgtatatc    300

attagcattg cgggtagcgt ggcggttggc aaaagcacct ttgcgcgtgt gctgcaggcg    360

ctgctgagcc gttggccgga gcatcgtcgt gttgaacata tcaccaccga cggcttcctg    420

cacccgaacc aagtgctgaa ggagcgtggt ctgatgggga aaaagggttt cccggaaagc    480

tacgatatgc accgtctgat gaaatttgtt aaagacctga agagcggtgt gccgaacgtt    540

accgcgccgg tgtacagcca cctgatctat gatgttattc cggacggcga taaaaccgtg    600

gttcagccgg acatcctgat tctggagggt ctgaacgtgc tgcaaagcgg catggactat    660

ccgcacgagc cgcaccacgt gtttgttagc gacttcgtgg attttagcat ctacgttgac    720
```

```
gcgccggagg atctgctgca gacctggtac attaaccgtt tcctgaaact gcgtgagggt    780

gcgttcaccg acccggatag ctactttcac gggtatgcga aactgaccaa ggaagaggcg    840

atcaaaaccg cgatgaccat ttggaaggag atgaaccacg tgaacctgaa gcaaaacatt    900

ctgccgaccc gtgaacgtgc gagcctgatt ctgaccaaaa gcgcaaacca catcgtggag    960

gaagttcgtc tgcgtaag                                                  978


<210> SEQ ID NO 256
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 256

Met His His His His His His Gly Gly Ser Gly Ser Ile Lys Glu Gln
1               5                   10                  15

Thr Glu Met Thr Pro Tyr Leu Gln Leu Asp Arg Asn Gln Trp Ala Ala
            20                  25                  30

Leu Arg Asp Ser Asn Pro Met Thr Leu Ser Glu Asp Glu Ile Ala Arg
        35                  40                  45

Leu Lys Gly Ile Asn Glu Asp Leu Ser Leu Glu Glu Val Ala Glu Val
    50                  55                  60

Tyr Leu Pro Leu Ser Arg Leu Leu Asn Ile Tyr Ile Ser Ser Asn Leu
65                  70                  75                  80

Arg Arg Gln Ala Gln Leu Glu Gln Phe Leu Gly Thr Asn Gly Gln Arg
                85                  90                  95

Ile Pro Tyr Ile Ile Ser Ile Ala Gly Ser Val Ala Val Gly Lys Ser
            100                 105                 110

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Glu Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Leu Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn His Val Asn Leu Lys Gln Asn Ile Leu Pro Thr Arg
    290                 295                 300

Glu Arg Ala Ser Leu Ile Leu Thr Lys Ser Ala Asn His Ile Val Glu
```

305 310 315 320

Glu Val Arg Leu Arg Lys
325

<210> SEQ ID NO 257
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 257
atgcaccatc atcatcatca tggcggtagc ggcagcatca aagagcagac cctgatgacc 60
ccgtacctgc agctggaccg taaccaatgg gcggcgctgc gtgatagtaa cccgatgacc 120
ctgagcgagg acgaaatcgc gcgtctgaag ggtattaacg aagatctgag cctggaggaa 180
gtggcggaag tctacctgcc gctgagccgt ctgctgaact tctatattag cagcaacctg 240
cgtcgtcagg cgcagctgga acagtttctg ggtaccaatg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaatgtt 540
accgcgccgg tgtacagcca cctgatctat gatgttattc cggacggcga taaaaccgtg 600
gtgcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaatt tcgtgagggt 780
gcgttcaccg acccggatag ctactttcac gggtatgcgc gtctgaccaa ggaagaggcg 840
atcaaaaccg cgatgagtat ttggaaggag atgaaccacg tgaacctgaa gcaaaacatt 900
ctgccgaccc gggaacgtgc gagcctgatt ctgaccaaaa gcgcaaacca catcgtggag 960
gaagttcgtc tgcgtaag 978

<210> SEQ ID NO 258
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 258

Met His His His His His His Gly Gly Ser Gly Ser Ile Lys Glu Gln
1 5 10 15

Thr Leu Met Thr Pro Tyr Leu Gln Leu Asp Arg Asn Gln Trp Ala Ala
20 25 30

Leu Arg Asp Ser Asn Pro Met Thr Leu Ser Glu Asp Glu Ile Ala Arg
35 40 45

Leu Lys Gly Ile Asn Glu Asp Leu Ser Leu Glu Glu Val Ala Glu Val
50 55 60

Tyr Leu Pro Leu Ser Arg Leu Leu Asn Phe Tyr Ile Ser Ser Asn Leu
65 70 75 80

Arg Arg Gln Ala Gln Leu Glu Gln Phe Leu Gly Thr Asn Gly Gln Arg
85 90 95

Ile Pro Tyr Ile Ile Ser Ile Ala Gly Ser Val Ala Val Gly Lys Ser
100 105 110

-continued

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Phe Arg Glu Gly Ala Phe Thr Asp Pro Asp Ser Tyr Phe His Gly Tyr
            260                 265                 270

Ala Arg Leu Thr Lys Glu Glu Ala Ile Lys Thr Ala Met Ser Ile Trp
        275                 280                 285

Lys Glu Met Asn His Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
                325

<210> SEQ ID NO 259
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 259
atgcaccatc atcatcatca tggcggtagc ggcagcatca aagagcagac cctgatgtcg 60
ccgtacctgc agctggaccg taaccaatgg gcggcgctgc gtgatagtaa cccgatgacc 120
ctgagcgagg acgaaatcgc gcgtctgaag ggtattaacg aagatctgag cctggaggaa 180
gtggcggaag tctacctgcc gctgagccgt ctgctgaact tctatattag cagcaacctg 240
cgtcgtcagg cgcagctgga acagtttctg ggtaccaatg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600
gttcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaatt tcgtgagggt 780

```
gcgttcaccg acccggatag ctactttcac gggtatgcga aactgaccaa ggaagaggcg    840

atcaaaaccg cgatgaccat ttggaaggag atgaaccacg tgaacctgaa gcaaaacatt    900

ctgccgaccc gtgaacgtgc gagcctgatt ctgaccaaaa gcgcaaacca catcgtggag    960

gaagttcgtc tgcgtaag                                                  978


<210> SEQ ID NO 260
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 260

Met His His His His His His Gly Gly Ser Gly Ser Ile Lys Glu Gln
1               5                   10                  15

Thr Leu Met Ser Pro Tyr Leu Gln Leu Asp Arg Asn Gln Trp Ala Ala
            20                  25                  30

Leu Arg Asp Ser Asn Pro Met Thr Leu Ser Glu Asp Glu Ile Ala Arg
        35                  40                  45

Leu Lys Gly Ile Asn Glu Asp Leu Ser Leu Glu Glu Val Ala Glu Val
    50                  55                  60

Tyr Leu Pro Leu Ser Arg Leu Leu Asn Phe Tyr Ile Ser Ser Asn Leu
65                  70                  75                  80

Arg Arg Gln Ala Gln Leu Glu Gln Phe Leu Gly Thr Asn Gly Gln Arg
                85                  90                  95

Ile Pro Tyr Ile Ile Ser Ile Ala Gly Ser Val Ala Val Gly Lys Ser
            100                 105                 110

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Phe Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn His Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
```

325

<210> SEQ ID NO 261
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 261
atgcaccatc atcatcatca tggcggtagc ggcagcatca aagagcagac ctggatgacc 60
ccgtacctgc agctggaccg taaccaatgg gcggcgctgc gtgatagtaa cccgatgacc 120
ctgagcgagg acgaaatcgc gcgtctgaag ggtattaacg aagatctgag cctggaggaa 180
gtggcggaag tctacctgcc gctgagccgt ctgctgaact tctatattag cagcaacctg 240
cgtcgtcagg cgcagctgga acagtttctg ggtaccaatg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600
gttcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaatt tcgtgagggt 780
gcgttcaccg acccggatag ctactttcac gggtatgcga aactgaccaa ggaagaggcg 840
atcaaaaccg cgatgaccat ttggaaggag atgaaccacg tgaacctgaa gcaaaacatt 900
ctgccgaccc gtgaacgtgc gagcctgatt ctgaccaaaa gcgcaaacca catcgtggag 960
gaagttcgtc tgcgtaag 978

<210> SEQ ID NO 262
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 262

Met His His His His His His Gly Gly Ser Gly Ser Ile Lys Glu Gln
1 5 10 15

Thr Trp Met Thr Pro Tyr Leu Gln Leu Asp Arg Asn Gln Trp Ala Ala
20 25 30

Leu Arg Asp Ser Asn Pro Met Thr Leu Ser Glu Asp Glu Ile Ala Arg
35 40 45

Leu Lys Gly Ile Asn Glu Asp Leu Ser Leu Glu Glu Val Ala Glu Val
50 55 60

Tyr Leu Pro Leu Ser Arg Leu Leu Asn Phe Tyr Ile Ser Ser Asn Leu
65 70 75 80

Arg Arg Gln Ala Gln Leu Glu Gln Phe Leu Gly Thr Asn Gly Gln Arg
85 90 95

Ile Pro Tyr Ile Ile Ser Ile Ala Gly Ser Val Ala Val Gly Lys Ser
100 105 110

Thr Phe Ala Arg Val Leu Gln Ala Leu Leu Ser Arg Trp Pro Glu His
115 120 125

```
Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Phe Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn His Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
                325
```

<210> SEQ ID NO 263
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 263

```
atgcaccatc atcatcatca tggcggtagc ggcagcatca aagagcagac cgagatgacc      60

ccgtacctgc aactggaccg taaccaatgg gcggcggtgc gtgatagtaa cccgatgacc     120

ctgagcgagg acgaaatcgc gcgtctgaag ggtattaacg aagatctgag cctggaggaa     180

gtggcggaag tctacctgcc gctgagccgt attctgaact tctatattag cagcaacctg     240

cgtcgtcagg cgcagctgga acagtttctg ggtaccaatg gccagcgtat cccgtatatc     300

attagcattg cgggtagcgt ggcggttggc aaaagcacct ttgcgcgtgt gctgcaggcg     360

ctgctgagcc gttggccgga gcatcgtcgt gttgaacata tcaccaccga cggcttcctg     420

cacccgaacc aagtgctgaa ggagcgtggt ctgatgggga aaaagggttt cccggaaagc     480

tacgatatgc accgtctgat gaaatttgtt aaagacctga agagcggtgt gccgaacgtt     540

accgcgccgg tgtacagcca cctgatctat gatgttattc cggacggcga taaaaccgtg     600

gttcagccgg acatcctgat tctggagggt ctgaacgtgc tgcaaagcgg catggactat     660

ccgcacgatc cgcaccacgt gtttgttagc gacttcgtgg attttagcat ctacgttgac     720

gcgccggagg atctgctgca gacctggtac attaaccgtt tcctgaaact gcgtgagggt     780

gcgttcaccg acccggatag ctactttcac gggtatgcga aactgaccaa ggaagaggcg     840

atcaaaaccg cgatgaccat ttggaaggag atgaacagcg tgaacctgaa gcaaaacatt     900
```

ctgccgaccc gtgaacgtgc gagcctgatt ctgaccaaag gtgcaaacca catcgtagag 960
gaagttcgtc tgcgtaag 978

<210> SEQ ID NO 264
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 264

Met His His His His His His Gly Gly Ser Gly Ser Ile Lys Glu Gln
1 5 10 15

Thr Glu Met Thr Pro Tyr Leu Gln Leu Asp Arg Asn Gln Trp Ala Ala
20 25 30

Val Arg Asp Ser Asn Pro Met Thr Leu Ser Glu Asp Glu Ile Ala Arg
35 40 45

Leu Lys Gly Ile Asn Glu Asp Leu Ser Leu Glu Glu Val Ala Glu Val
50 55 60

Tyr Leu Pro Leu Ser Arg Ile Leu Asn Phe Tyr Ile Ser Ser Asn Leu
65 70 75 80

Arg Arg Gln Ala Gln Leu Glu Gln Phe Leu Gly Thr Asn Gly Gln Arg
85 90 95

Ile Pro Tyr Ile Ile Ser Ile Ala Gly Ser Val Ala Val Gly Lys Ser
100 105 110

Thr Phe Ala Arg Val Leu Gln Ala Leu Leu Ser Arg Trp Pro Glu His
115 120 125

Arg Arg Val Glu His Ile Thr Thr Asp Gly Phe Leu His Pro Asn Gln
130 135 140

Val Leu Lys Glu Arg Gly Leu Met Gly Lys Lys Gly Phe Pro Glu Ser
145 150 155 160

Tyr Asp Met His Arg Leu Met Lys Phe Val Lys Asp Leu Lys Ser Gly
165 170 175

Val Pro Asn Val Thr Ala Pro Val Tyr Ser His Leu Ile Tyr Asp Val
180 185 190

Ile Pro Asp Gly Asp Lys Thr Val Val Gln Pro Asp Ile Leu Ile Leu
195 200 205

Glu Gly Leu Asn Val Leu Gln Ser Gly Met Asp Tyr Pro His Asp Pro
210 215 220

His His Val Phe Val Ser Asp Phe Val Asp Phe Ser Ile Tyr Val Asp
225 230 235 240

Ala Pro Glu Asp Leu Leu Gln Thr Trp Tyr Ile Asn Arg Phe Leu Lys
245 250 255

Leu Arg Glu Gly Ala Phe Thr Asp Pro Asp Ser Tyr Phe His Gly Tyr
260 265 270

Ala Lys Leu Thr Lys Glu Glu Ala Ile Lys Thr Ala Met Thr Ile Trp
275 280 285

Lys Glu Met Asn Ser Val Asn Leu Lys Gln Asn Ile Leu Pro Thr Arg
290 295 300

Glu Arg Ala Ser Leu Ile Leu Thr Lys Gly Ala Asn His Ile Val Glu
305 310 315 320

Glu Val Arg Leu Arg Lys
325

<210> SEQ ID NO 265
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 265
atgcaccatc atcatcatca tggcggtagc ggcagcatca aagagcagac cgagatgacc 60
cagtaccgtc aactggaccg taaccaatgg gcggcggtgc gtgatagtaa cccgatgacc 120
ctgagcgagg acgaaatcgc gcgtctgaag ggtattaacg aagatctgag cctggaggaa 180
gtggcggaag tctacctgcc gctgagccgt gttctgaact tctatattag cagcaacctg 240
cgtcgtcagg cgcagctgga acagtttctg ggtaccaatg gcgtgcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600
gttcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaact gcgtgagggt 780
gcgttcaccg acccggatag ctactttcac gggtatgcga aactgaccaa ggaagaggcg 840
atcaaaaccg cgatgaccat ttggaaggag atgaacagcg tgaacctgaa gcaaaacatt 900
ctgccgaccc gtgaacgtgc gagcctgatt ctgaccaaag gtgcaaacca catcgtggag 960
gaagttcgtc tgcgtaag 978

<210> SEQ ID NO 266
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 266

Met His His His His His His Gly Gly Ser Gly Ser Ile Lys Glu Gln
1 5 10 15

Thr Glu Met Thr Gln Tyr Arg Gln Leu Asp Arg Asn Gln Trp Ala Ala
20 25 30

Val Arg Asp Ser Asn Pro Met Thr Leu Ser Glu Asp Glu Ile Ala Arg
35 40 45

Leu Lys Gly Ile Asn Glu Asp Leu Ser Leu Glu Glu Val Ala Glu Val
50 55 60

Tyr Leu Pro Leu Ser Arg Val Leu Asn Phe Tyr Ile Ser Ser Asn Leu
65 70 75 80

Arg Arg Gln Ala Gln Leu Glu Gln Phe Leu Gly Thr Asn Gly Val Arg
85 90 95

Ile Pro Tyr Ile Ile Ser Ile Ala Gly Ser Val Ala Val Gly Lys Ser
100 105 110

Thr Phe Ala Arg Val Leu Gln Ala Leu Leu Ser Arg Trp Pro Glu His
115 120 125

Arg Arg Val Glu His Ile Thr Thr Asp Gly Phe Leu His Pro Asn Gln
130 135 140

Val Leu Lys Glu Arg Gly Leu Met Gly Lys Lys Gly Phe Pro Glu Ser
145 150 155 160

Tyr Asp Met His Arg Leu Met Lys Phe Val Lys Asp Leu Lys Ser Gly
165 170 175

Val Pro Asn Val Thr Ala Pro Val Tyr Ser His Leu Ile Tyr Asp Val
180 185 190

Ile Pro Asp Gly Asp Lys Thr Val Val Gln Pro Asp Ile Leu Ile Leu
195 200 205

Glu Gly Leu Asn Val Leu Gln Ser Gly Met Asp Tyr Pro His Asp Pro
210 215 220

His His Val Phe Val Ser Asp Phe Val Asp Phe Ser Ile Tyr Val Asp
225 230 235 240

Ala Pro Glu Asp Leu Leu Gln Thr Trp Tyr Ile Asn Arg Phe Leu Lys
245 250 255

Leu Arg Glu Gly Ala Phe Thr Asp Pro Asp Ser Tyr Phe His Gly Tyr
260 265 270

Ala Lys Leu Thr Lys Glu Glu Ala Ile Lys Thr Ala Met Thr Ile Trp
275 280 285

Lys Glu Met Asn Ser Val Asn Leu Lys Gln Asn Ile Leu Pro Thr Arg
290 295 300

Glu Arg Ala Ser Leu Ile Leu Thr Lys Gly Ala Asn His Ile Val Glu
305 310 315 320

Glu Val Arg Leu Arg Lys
325

<210> SEQ ID NO 267
<211> LENGTH: 978
<212> TYPE: DNA
<213> ORGANISM: Artificial Sequence
<220> FEATURE:
<223> OTHER INFORMATION: Pantothenate Kinase from Escherichia coli

<400> SEQUENCE: 267
atgcaccatc atcatcatca tggcggtagc ggcagcatca aagagcagac cgagatgacc 60
ccgtacctgc aactggaccg taaccaatgg gcggcggtgc gtgatagtaa cccgatgacc 120
ctgagcgagg acgaaatcgc gcgtctgaag ggtattaacg aagatctgag cctggaggaa 180
gtggcggaag tctacctgcc gctgagccgt gttctgaact tctatattag cagcaacctg 240
cgtcgtcagg cgcagctgga acagtttctg ggtaccaatg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600
gttcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaact gcgtgagggt 780
gcgttcaccg acccggatag ctactttcac gggtatgcga aactgaccaa ggaagaggcg 840
atcaaaaccg cgatgaccat ttggaaggag atgaacagcg tgaacctgaa gcaaaacatt 900
ctgccgaccc gtgaacgtgc gagcctgatt ctgaccaaaa gtgcaaacca catcgtggag 960
gaagttcgtc tgcgtaag 978

<210> SEQ ID NO 268
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 268

```
Met His His His His His His Gly Gly Ser Gly Ser Ile Lys Glu Gln
1               5                   10                  15

Thr Glu Met Thr Pro Tyr Leu Gln Leu Asp Arg Asn Gln Trp Ala Ala
            20                  25                  30

Val Arg Asp Ser Asn Pro Met Thr Leu Ser Glu Asp Glu Ile Ala Arg
        35                  40                  45

Leu Lys Gly Ile Asn Glu Asp Leu Ser Leu Glu Glu Val Ala Glu Val
    50                  55                  60

Tyr Leu Pro Leu Ser Arg Val Leu Asn Phe Tyr Ile Ser Ser Asn Leu
65                  70                  75                  80

Arg Arg Gln Ala Gln Leu Glu Gln Phe Leu Gly Thr Asn Gly Gln Arg
                85                  90                  95

Ile Pro Tyr Ile Ile Ser Ile Ala Gly Ser Val Ala Val Gly Lys Ser
            100                 105                 110

Thr Phe Ala Arg Val Leu Gln Ala Leu Leu Ser Arg Trp Pro Glu His
        115                 120                 125

Arg Arg Val Glu His Ile Thr Thr Asp Gly Phe Leu His Pro Asn Gln
    130                 135                 140

Val Leu Lys Glu Arg Gly Leu Met Gly Lys Lys Gly Phe Pro Glu Ser
145                 150                 155                 160

Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Leu Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn Ser Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
                325
```

<210> SEQ ID NO 269
<211> LENGTH: 978
<212> TYPE: DNA

<213> ORGANISM: Artificial Sequence
<220> FEATURE:
<223> OTHER INFORMATION: Pantothenate Kinase from Escherichia coli

<400> SEQUENCE: 269
atgcaccatc atcatcatca tggcggtagc ggcagcatca aagagcagac cgagatgacc 60
ccgtaccgtc aactggaccg taacacttgg gcggcgctgc gtgatagtaa cccgatgacc 120
ctgagcgagg acgaaatcgc gcgtctgaag ggtattaacg aagatctgag cctggaggaa 180
gtggcggaag tctacctgcc gctgagccgt attctgaact tctatattag cagcaacctg 240
cgtcgtcagg cgcagctgga acagtttctg ggtaccaatg gccagcgtat cccgtatatc 300
attagcattg cgggtagcgt ggcggttggc aaaagcacct ttgcgcgtgt gctgcaggcg 360
ctgctgagcc gttggccgga gcatcgtcgt gttgaacata tcaccaccga cggcttcctg 420
cacccgaacc aagtgctgaa ggagcgtggt ctgatgggga aaaagggttt cccggaaagc 480
tacgatatgc accgtctgat gaaatttgtt aaagacctga agagcggtgt gccgaacgtt 540
accgcgccgg tgtacagcca cctgatctat gatgttattc cggacggcga taaaaccgtg 600
gttcagccgg acatcctgat tctggagggt ctgaacgtgc tgcaaagcgg catggactat 660
ccgcacgatc cgcaccacgt gtttgttagc gacttcgtgg attttagcat ctacgttgac 720
gcgccggagg atctgctgca gacctggtac attaaccgtt tcctgaaact gcgtgagggt 780
gcgttcaccg acccggatag ctactttcac gggtatgcga aactgaccaa ggaagaggcg 840
atcaaaaccg cgatgaccat ttggaaggag atgaacagcg tgaacctgaa gcaaaacatt 900
ctgccgaccc gtgaacgtgc gagcctgatt ctgaccaaaa gtgcaaacca catcgtggag 960
gaagttcgtc tgcgtaag 978

<210> SEQ ID NO 270
<211> LENGTH: 326
<212> TYPE: PRT
<213> ORGANISM: Artificial Sequence
<220> FEATURE:
<223> OTHER INFORMATION: Pantothenate Kinase from Escherichia coli

<400> SEQUENCE: 270

Met His His His His His His Gly Gly Ser Gly Ser Ile Lys Glu Gln
1 5 10 15

Thr Glu Met Thr Pro Tyr Arg Gln Leu Asp Arg Asn Thr Trp Ala Ala
20 25 30

Leu Arg Asp Ser Asn Pro Met Thr Leu Ser Glu Asp Glu Ile Ala Arg
35 40 45

Leu Lys Gly Ile Asn Glu Asp Leu Ser Leu Glu Glu Val Ala Glu Val
50 55 60

Tyr Leu Pro Leu Ser Arg Ile Leu Asn Phe Tyr Ile Ser Ser Asn Leu
65 70 75 80

Arg Arg Gln Ala Gln Leu Glu Gln Phe Leu Gly Thr Asn Gly Gln Arg
85 90 95

Ile Pro Tyr Ile Ile Ser Ile Ala Gly Ser Val Ala Val Gly Lys Ser
100 105 110

Thr Phe Ala Arg Val Leu Gln Ala Leu Leu Ser Arg Trp Pro Glu His
115 120 125

Arg Arg Val Glu His Ile Thr Thr Asp Gly Phe Leu His Pro Asn Gln
130 135 140

Val Leu Lys Glu Arg Gly Leu Met Gly Lys Lys Gly Phe Pro Glu Ser
145 150 155 160

```
Tyr Asp Met His Arg Leu Met Lys Phe Val Lys Asp Leu Lys Ser Gly
                165                 170                 175

Val Pro Asn Val Thr Ala Pro Val Tyr Ser His Leu Ile Tyr Asp Val
            180                 185                 190

Ile Pro Asp Gly Asp Lys Thr Val Val Gln Pro Asp Ile Leu Ile Leu
        195                 200                 205

Glu Gly Leu Asn Val Leu Gln Ser Gly Met Asp Tyr Pro His Asp Pro
    210                 215                 220

His His Val Phe Val Ser Asp Phe Val Asp Phe Ser Ile Tyr Val Asp
225                 230                 235                 240

Ala Pro Glu Asp Leu Leu Gln Thr Trp Tyr Ile Asn Arg Phe Leu Lys
                245                 250                 255

Leu Arg Glu Gly Ala Phe Thr Asp Pro Asp Ser Tyr Phe His Gly Tyr
            260                 265                 270

Ala Lys Leu Thr Lys Glu Glu Ala Ile Lys Thr Ala Met Thr Ile Trp
        275                 280                 285

Lys Glu Met Asn Ser Val Asn Leu Lys Gln Asn Ile Leu Pro Thr Arg
    290                 295                 300

Glu Arg Ala Ser Leu Ile Leu Thr Lys Ser Ala Asn His Ile Val Glu
305                 310                 315                 320

Glu Val Arg Leu Arg Lys
                325


<210> SEQ ID NO 271
<211> LENGTH: 1239
<212> TYPE: DNA
<213> ORGANISM: Artificial Sequence
<220> FEATURE:
<223> OTHER INFORMATION: Variant of Acetate Kinase from Thermotoga
      maritima

<400> SEQUENCE: 271

atgggtagcc atcatcatca tcatcacggt agccgtgttc tggttattaa tagcggtagc     60

agcagcatta aatatcagct gattgaaatg gaaggtgaaa aagttctgtg taaaggtatt    120

gcagaacgta ttggtattga aggtagccgt ctggttcatc gtgttggtga tgaaaaacat    180

gttattgaac gtgaactgcc ggatcatgaa gaagcactga aactgattct gaataccctg    240

gttgatgaaa aactgggtgt tattaaagat ctgaaagaaa ttgacgcagt tggtcatcgt    300

gttgttcatg gtggtgaacg ttttaaagaa agcgttctgg ttgatgaaga agttctgaaa    360

gcaattgaag aagttagccc gctggcaccg ctgcataatc cggcaaatct gatgggtatt    420

aaagcagcaa tgaaactgct gccgggtgtt ccgaatgttg cagtttttga taccgcattt    480

catcagacca ttccgcagaa agcatatctg tatgcaattc cgtatgaata ttacgaaaaa    540

tacaaaattc gtcgctacgg ttttcatggt accagccatc gttatgttag caaacgtgca    600

gcagaaattc tgggtaaaaa actggaagaa ctgaaaatta tcacctgtca tattggtaat    660

ggtgcaagcg ttgcagcagt taaatatggt aaatgtgttg ataccagcat gggttttacc    720

ccgctggaag gtctggttat gggtacccgt agcggtgatc tggatccggc aattccgttt    780

tttattatgg aaaaagaggg tattagcccg caggaaatgt atgatattct gaataaaaaa    840

agcggcgttt atggtctgag caaaggtttt agcagcgata tgcgtgatat taaggaagca    900

gcactgaaag gtgatgaatg gtgtaaactg gttctggaaa tttatgatta ccgtattgca    960

aaatacatcg gtgcatacgc tgcagcaatg aatggtgttg atgcaattgt ttttaccgca   1020
```

ggtgttggtg aaaatagccc gattacccgt gaagatgttt gtagctatct ggaatttctg 1080
ggtgttaaac tggataaaca gaaaaatgaa gagaccattc gtggtaaaga aggtattatt 1140
agcaccccgg atagccgtgt taaagttctg gttgttccga ccaatgaaga actgatgatt 1200
gcacgtgata ccaaagaaat tgttgaaaaa atcggtcgt 1239

<210> SEQ ID NO 272
<211> LENGTH: 413
<212> TYPE: PRT
<213> ORGANISM: Artificial Sequence
<220> FEATURE:
<223> OTHER INFORMATION: Variant of Acetate Kinase from Thermotoga maritima

<400> SEQUENCE: 272

Met Gly Ser His His His His His His Gly Ser Arg Val Leu Val Ile
1 5 10 15

Asn Ser Gly Ser Ser Ser Ile Lys Tyr Gln Leu Ile Glu Met Glu Gly
20 25 30

Glu Lys Val Leu Cys Lys Gly Ile Ala Glu Arg Ile Gly Ile Glu Gly
35 40 45

Ser Arg Leu Val His Arg Val Gly Asp Glu Lys His Val Ile Glu Arg
50 55 60

Glu Leu Pro Asp His Glu Glu Ala Leu Lys Leu Ile Leu Asn Thr Leu
65 70 75 80

Val Asp Glu Lys Leu Gly Val Ile Lys Asp Leu Lys Glu Ile Asp Ala
85 90 95

Val Gly His Arg Val Val His Gly Gly Glu Arg Phe Lys Glu Ser Val
100 105 110

Leu Val Asp Glu Glu Val Leu Lys Ala Ile Glu Glu Val Ser Pro Leu
115 120 125

Ala Pro Leu His Asn Pro Ala Asn Leu Met Gly Ile Lys Ala Ala Met
130 135 140

Lys Leu Leu Pro Gly Val Pro Asn Val Ala Val Phe Asp Thr Ala Phe
145 150 155 160

His Gln Thr Ile Pro Gln Lys Ala Tyr Leu Tyr Ala Ile Pro Tyr Glu
165 170 175

Tyr Tyr Glu Lys Tyr Lys Ile Arg Arg Tyr Gly Phe His Gly Thr Ser
180 185 190

His Arg Tyr Val Ser Lys Arg Ala Ala Glu Ile Leu Gly Lys Lys Leu
195 200 205

Glu Glu Leu Lys Ile Ile Thr Cys His Ile Gly Asn Gly Ala Ser Val
210 215 220

Ala Ala Val Lys Tyr Gly Lys Cys Val Asp Thr Ser Met Gly Phe Thr
225 230 235 240

Pro Leu Glu Gly Leu Val Met Gly Thr Arg Ser Gly Asp Leu Asp Pro
245 250 255

Ala Ile Pro Phe Phe Ile Met Glu Lys Glu Gly Ile Ser Pro Gln Glu
260 265 270

Met Tyr Asp Ile Leu Asn Lys Lys Ser Gly Val Tyr Gly Leu Ser Lys
275 280 285

Gly Phe Ser Ser Asp Met Arg Asp Ile Lys Glu Ala Ala Leu Lys Gly
290 295 300

Asp Glu Trp Cys Lys Leu Val Leu Glu Ile Tyr Asp Tyr Arg Ile Ala
305 310 315 320

```
Lys Tyr Ile Gly Ala Tyr Ala Ala Ala Met Asn Gly Val Asp Ala Ile
                325                 330                 335

Val Phe Thr Ala Gly Val Gly Glu Asn Ser Pro Ile Thr Arg Glu Asp
            340                 345                 350

Val Cys Ser Tyr Leu Glu Phe Leu Gly Val Lys Leu Asp Lys Gln Lys
        355                 360                 365

Asn Glu Glu Thr Ile Arg Gly Lys Glu Gly Ile Ile Ser Thr Pro Asp
    370                 375                 380

Ser Arg Val Lys Val Leu Val Val Pro Thr Asn Glu Glu Leu Met Ile
385                 390                 395                 400

Ala Arg Asp Thr Lys Glu Ile Val Glu Lys Ile Gly Arg
                405                 410
```

<210> SEQ ID NO 273
<211> LENGTH: 1239
<212> TYPE: DNA
<213> ORGANISM: Artificial Sequence
<220> FEATURE:
<223> OTHER INFORMATION: Variant of Acetate Kinase from Thermotoga maritima

<400> SEQUENCE: 273

```
atgggtagcc atcatcatca tcatcacggt agccgtgttc tgaatatcaa tagcggtagc     60

agcagcatta aatatcagct gattgaaatg gaaggtgaaa aagttctgtg taaaggtatt    120

gcagaacgta ttggtattga aggtagccgt ctggttcatc gtgttggtga tgaaaaacat    180

gttattgaac gtgaactgcc ggatcatgaa gaagcactga aactgattct gaataccctg    240

gttgatgaaa aactgggtgt tattaaagat ctgaaagaaa ttgacgcagt tggtcatcgt    300

gttgttcatg gtggtgaacg ttttaaagaa agcgttctgg ttgatgaaga agttctgaaa    360

gcaattgaag aagttagccc gctggcaccg ctgcataatc cggcaaatct gatgggtatt    420

aaagcagcaa tgaaactgct gccgggtgtt ccgaatgttc aagtttttga taccgcattt    480

catcagacca ttccgcagaa agcatatctg tatgcaattc cgtatgaata ttacgaaaaa    540

tacaaaattc gtcgctacgg ttttcatggt atcagccatc gttatgttag caaacgtgca    600

gcagaaattc tgggtaaaaa actggaagaa ctgaaaatta tcacctgtca tattggtaat    660

ggtgcaagcg ttgcagcagt taaatatggt aaatgtgttg ataccagcat gggttttacc    720

ccgctggaag gtctggttat gggtacccgt agcggtgatc tggatccggc aattccgttt    780

tttattatgg aaaaagaggg tattagcccg caggaaatgt atgatattct gaataaaaaa    840

agcggcgttt atggtctgag caaaggtttt agcagcgata tgcgtgataa tctggaagca    900

gcactgaaag gtgatgaatg gtgtaaactg gttctggaaa tttatgatta ccgtattgca    960

aaatacatcg gtgcatacgc tgcagcaatg aatggtgttg atgcaattgt ttttaccgca   1020

ggtgttggtg aaaatagccc gatcacccgt gaagatgttt gtaagtatct ggaatttctg   1080

ggtgttaaac tggataaaca gaaaaatgaa gagaccattc gtggtaaaga aggtattatt   1140

agcaccccgg atagccgtgt taaagttctg gttgttccga ccaatgaaga actgatgatt   1200

gcacgtgata ccaaagaaat tgttgaaaaa atcggtcgt                          1239
```

<210> SEQ ID NO 274
<211> LENGTH: 413
<212> TYPE: PRT
<213> ORGANISM: Artificial Sequence
<220> FEATURE:
<223> OTHER INFORMATION: Variant of Acetate Kinase from Thermotoga maritima

<400> SEQUENCE: 274

```
Met Gly Ser His His His His His His Gly Ser Arg Val Leu Asn Ile
1               5                   10                  15

Asn Ser Gly Ser Ser Ser Ile Lys Tyr Gln Leu Ile Glu Met Glu Gly
            20                  25                  30

Glu Lys Val Leu Cys Lys Gly Ile Ala Glu Arg Ile Gly Ile Glu Gly
        35                  40                  45

Ser Arg Leu Val His Arg Val Gly Asp Glu Lys His Val Ile Glu Arg
    50                  55                  60

Glu Leu Pro Asp His Glu Glu Ala Leu Lys Leu Ile Leu Asn Thr Leu
65                  70                  75                  80

Val Asp Glu Lys Leu Gly Val Ile Lys Asp Leu Lys Glu Ile Asp Ala
                85                  90                  95

Val Gly His Arg Val Val His Gly Gly Glu Arg Phe Lys Glu Ser Val
            100                 105                 110

Leu Val Asp Glu Glu Val Leu Lys Ala Ile Glu Glu Val Ser Pro Leu
        115                 120                 125

Ala Pro Leu His Asn Pro Ala Asn Leu Met Gly Ile Lys Ala Ala Met
    130                 135                 140

Lys Leu Leu Pro Gly Val Pro Asn Val Gln Val Phe Asp Thr Ala Phe
145                 150                 155                 160

His Gln Thr Ile Pro Gln Lys Ala Tyr Leu Tyr Ala Ile Pro Tyr Glu
                165                 170                 175

Tyr Tyr Glu Lys Tyr Lys Ile Arg Arg Tyr Gly Phe His Gly Ile Ser
            180                 185                 190

His Arg Tyr Val Ser Lys Arg Ala Ala Glu Ile Leu Gly Lys Lys Leu
        195                 200                 205

Glu Glu Leu Lys Ile Ile Thr Cys His Ile Gly Asn Gly Ala Ser Val
    210                 215                 220

Ala Ala Val Lys Tyr Gly Lys Cys Val Asp Thr Ser Met Gly Phe Thr
225                 230                 235                 240

Pro Leu Glu Gly Leu Val Met Gly Thr Arg Ser Gly Asp Leu Asp Pro
                245                 250                 255

Ala Ile Pro Phe Phe Ile Met Glu Lys Glu Gly Ile Ser Pro Gln Glu
            260                 265                 270

Met Tyr Asp Ile Leu Asn Lys Lys Ser Gly Val Tyr Gly Leu Ser Lys
        275                 280                 285

Gly Phe Ser Ser Asp Met Arg Asp Asn Leu Glu Ala Ala Leu Lys Gly
    290                 295                 300

Asp Glu Trp Cys Lys Leu Val Leu Glu Ile Tyr Asp Tyr Arg Ile Ala
305                 310                 315                 320

Lys Tyr Ile Gly Ala Tyr Ala Ala Ala Met Asn Gly Val Asp Ala Ile
                325                 330                 335

Val Phe Thr Ala Gly Val Gly Glu Asn Ser Pro Ile Thr Arg Glu Asp
            340                 345                 350

Val Cys Lys Tyr Leu Glu Phe Leu Gly Val Lys Leu Asp Lys Gln Lys
        355                 360                 365

Asn Glu Glu Thr Ile Arg Gly Lys Glu Gly Ile Ile Ser Thr Pro Asp
    370                 375                 380

Ser Arg Val Lys Val Leu Val Val Pro Thr Asn Glu Glu Leu Met Ile
385                 390                 395                 400

Ala Arg Asp Thr Lys Glu Ile Val Glu Lys Ile Gly Arg
                405                 410
```

<210> SEQ ID NO 275
<211> LENGTH: 948
<212> TYPE: DNA
<213> ORGANISM: Artificial Sequence
<220> FEATURE:
<223> OTHER INFORMATION: Pantothenate Kinase from Escherichia coli

<400> SEQUENCE: 275

```
atgagcatca aagagcagac cgagatgacc ccgtacctgc aactggaccg taaccaatgg     60

gcggcgctgc gtgatagtaa cccgatgacc ctgagcgagg acgaaatcgc gcgtctgaag    120

ggtattaacg aagatctgag cctggaggaa gtggcggaag tctacctgcc gctgagccgt    180

ctgctgaact tctatattag cagcaacctg cgtcgtcagg cgcagctgga acagtttctg    240

ggtaccaatg gccagcgtat cccgtatatc attagcattg cgggtagcgt ggcggttggc    300

aaaagcacct ttgcgcgtgt gctgcaggcg ctgctgagcc gttggccgga gcatcgtcgt    360

gttgaacata tcaccaccga cggcttcctg cacccgaacc aagtgctgaa ggagcgtggt    420

ctgatgggga aaaagggttt cccggaaagc tacgatatgc accgtctgat gaaatttgtt    480

aaagacctga agagcggtgt gccgaacgtt accgcgccgg tgtacagcca cctgatctat    540

gatgttattc cggacggcga taaaaccgtg gttcagccgg acatcctgat tctggagggt    600

ctgaacgtgc tgcaaagcgg catggactat ccgcacgatc cgcaccacgt gtttgttagc    660

gacttcgtgg attttagcat ctacgttgac gcgccggagg atctgctgca gacctggtac    720

attaaccgtt tcctgaaact gcgtgagggt gcgttcaccg acccggatag ctactttcac    780

gggtatgcga aactgaccaa ggaagaggcg atcaaaaccg cgatgaccat ttggaaggag    840

atgaacagcg tgaacctgaa gcaaaacatt ctgccgaccc gtgaacgtgc gagcctgatt    900

ctgaccaaaa gcgcaaacca catcgtggag gaagttcgtc tgcgtaag                948
```

<210> SEQ ID NO 276
<211> LENGTH: 316
<212> TYPE: PRT
<213> ORGANISM: Artificial Sequence
<220> FEATURE:
<223> OTHER INFORMATION: Pantothenate Kinase from Escherichia coli

<400> SEQUENCE: 276

```
Met Ser Ile Lys Glu Gln Thr Glu Met Thr Pro Tyr Leu Gln Leu Asp
1               5                   10                  15

Arg Asn Gln Trp Ala Ala Leu Arg Asp Ser Asn Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Val Tyr Leu Pro Leu Ser Arg Leu Leu Asn Phe
    50                  55                  60

Tyr Ile Ser Ser Asn Leu Arg Arg Gln Ala Gln Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Phe Ala Arg Val Leu Gln Ala Leu Leu
            100                 105                 110

Ser Arg Trp Pro Glu His Arg Arg Val Glu His Ile Thr Thr Asp Gly
        115                 120                 125

Phe Leu His Pro Asn Gln Val Leu Lys Glu Arg Gly Leu Met Gly Lys
    130                 135                 140
```

-continued

```
Lys Gly Phe Pro Glu Ser Tyr Asp Met His Arg Leu Met Lys Phe Val
145                 150                 155                 160

Lys Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240

Ile Asn Arg Phe Leu Lys Leu Arg Glu Gly Ala Phe Thr Asp Pro Asp
                245                 250                 255

Ser Tyr Phe His Gly Tyr Ala Lys Leu Thr Lys Glu Glu Ala Ile Lys
            260                 265                 270

Thr Ala Met Thr Ile Trp Lys Glu Met Asn Ser Val Asn Leu Lys Gln
        275                 280                 285

Asn Ile Leu Pro Thr Arg Glu Arg Ala Ser Leu Ile Leu Thr Lys Ser
    290                 295                 300

Ala Asn His Ile Val Glu Glu Val Arg Leu Arg Lys
305                 310                 315
```